(12) United States Patent
Soper et al.

(10) Patent No.: US 8,242,248 B2
(45) Date of Patent: Aug. 14, 2012

(54) KITS FOR MULTIPARAMETRIC PHOSPHO ANALYSIS

(75) Inventors: David Soper, San Francisco, CA (US); David Rosen, Mountain View, CA (US); Ying-Wen Huang, Palo Alto, CA (US); Wendy Fantl, San Francisco, CA (US)

(73) Assignee: Nodality, Inc., South San Francisco, CA (US)

(*) Notice: Subject to any disclaimer, the term of this patent is extended or adjusted under 35 U.S.C. 154(b) by 181 days.

(21) Appl. No.: 12/730,170

(22) Filed: Mar. 23, 2010

(65) Prior Publication Data

US 2010/0240542 A1 Sep. 23, 2010

Related U.S. Application Data

(60) Provisional application No. 61/162,673, filed on Mar. 23, 2009, provisional application No. 61/245,000, filed on Sep. 23, 2009.

(51) Int. Cl.
*C07K 16/00* (2006.01)
(52) U.S. Cl. ..................................... 530/387.1
(58) Field of Classification Search .................. None
See application file for complete search history.

(56) References Cited

U.S. PATENT DOCUMENTS

| | | | |
|---|---|---|---|
| 4,568,649 A | 2/1986 | Bertoglio-Matte | |
| 4,816,567 A | 3/1989 | Cabilly et al. | |
| 5,225,539 A | 7/1993 | Winter | |
| 5,292,658 A | 3/1994 | Cormier et al. | |
| 5,418,155 A | 5/1995 | Cormier et al. | |
| 5,530,101 A | 6/1996 | Queen et al. | |
| 5,585,089 A | 12/1996 | Queen et al. | |
| 5,683,888 A | 11/1997 | Campbell | |
| 5,693,761 A | 12/1997 | Queen et al. | |
| 5,693,762 A | 12/1997 | Queen et al. | |
| 5,741,668 A | 4/1998 | Ward et al. | |
| 5,777,079 A | 7/1998 | Tsien et al. | |
| 5,804,387 A | 9/1998 | Cormack et al. | |
| 5,821,337 A | 10/1998 | Carter et al. | |
| 5,859,205 A | 1/1999 | Adair et al. | |
| 5,874,304 A | 2/1999 | Zolotukhin et al. | |
| 5,876,995 A | 3/1999 | Bryan | |
| 5,925,558 A | 7/1999 | Tsien et al. | |
| 5,968,738 A | 10/1999 | Anderson et al. | |
| 6,054,297 A | 4/2000 | Carter et al. | |
| 6,180,370 B1 | 1/2001 | Queen et al. | |
| 6,407,213 B1 | 6/2002 | Carter et al. | |
| 6,495,333 B1 | 12/2002 | Willmann et al. | |
| 6,733,743 B2 | 5/2004 | Jordan | |
| 7,381,535 B2 | 6/2008 | Perez et al. | |
| 7,393,656 B2 * | 7/2008 | Perez et al. | 435/7.21 |
| 7,563,584 B2 | 7/2009 | Perez et al. | |
| 7,695,924 B2 | 4/2010 | Perez et al. | |
| 7,695,926 B2 | 4/2010 | Perez et al. | |
| 2006/0046272 A1 | 3/2006 | Chow et al. | |
| 2007/0009923 A1 | 1/2007 | Nolan et al. | |
| 2007/0196869 A1 | 8/2007 | Perez et al. | |
| 2009/0081699 A1 | 3/2009 | Perez et al. | |
| 2009/0098594 A1 | 4/2009 | Fantl et al. | |
| 2009/0269773 A1 | 10/2009 | Fantl et al. | |
| 2009/0269800 A1 | 10/2009 | Covey et al. | |
| 2009/0291458 A1 | 11/2009 | Cohen et al. | |
| 2009/0307248 A1 | 12/2009 | Moser et al. | |
| 2010/0009364 A1 | 1/2010 | Fantl et al. | |
| 2010/0014741 A1 | 1/2010 | Banville et al. | |
| 2010/0030719 A1 | 2/2010 | Covey et al. | |
| 2010/0042351 A1 | 2/2010 | Covey et al. | |
| 2010/0086951 A1 | 4/2010 | Hedley et al. | |
| 2010/0099109 A1 | 4/2010 | Fantl et al. | |
| 2010/0105074 A1 | 4/2010 | Covey et al. | |
| 2010/0151472 A1 | 6/2010 | Nolan et al. | |
| 2010/0204973 A1 | 8/2010 | Parkinson et al. | |
| 2010/0209929 A1 | 8/2010 | Fantl et al. | |
| 2010/0215644 A1 | 8/2010 | Fantl et al. | |
| 2010/0233733 A1 | 9/2010 | Fantl | |
| 2010/0285594 A1 | 11/2010 | Purvis, Jr. | |
| 2010/0297676 A1 | 11/2010 | Fantl et al. | |
| 2011/0059861 A1 | 3/2011 | Nolan et al. | |
| 2011/0104717 A1 | 5/2011 | Fantl et al. | |
| 2011/0262468 A1 | 10/2011 | Fantl et al. | |
| 2011/0269154 A1 | 11/2011 | Fantl et al. | |

FOREIGN PATENT DOCUMENTS

| | | |
|---|---|---|
| WO | WO 92/15673 A1 | 9/1992 |
| WO | WO 95/07463 A1 | 3/1995 |
| WO | WO 98/14605 A1 | 4/1998 |
| WO | WO 98/26277 A2 | 6/1998 |
| WO | WO 98/26277 A3 | 6/1999 |
| WO | WO 99/49019 A2 | 9/1999 |
| WO | WO 99/49019 A3 | 9/1999 |
| WO | WO 03/067210 A2 | 8/2003 |
| WO | WO 03/067210 A3 | 12/2003 |
| WO | WO 2006/012507 A2 | 2/2006 |

(Continued)

OTHER PUBLICATIONS

Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.

(Continued)

*Primary Examiner* — Sean Aeder

(74) *Attorney, Agent, or Firm* — Wilson Sonsini Goodrich & Rosati

(57) ABSTRACT

As disclosed herein, the present invention provides for kits and a composition for diagnosis, prognosis, drug discovery, drug development, and patient stratification. The kits can comprise a plurality of binding elements for cell surface markers, and a plurality of binding elements for state-specific intracellular markers. The kits can further comprise a plurality of modulators directed for the particular cell function or signaling pathways. The kits can further include fixatives, permeabilizing agent, buffers, containers, instructions, and software for data analysis/compilation.

17 Claims, 2 Drawing Sheets

FOREIGN PATENT DOCUMENTS

| | | |
|---|---|---|
| WO | WO 2006/012507 A3 | 10/2006 |
| WO | WO 2009/025847 A2 | 2/2009 |
| WO | WO 2009/025847 A3 | 6/2009 |
| WO | WO 2010/006291 A1 | 1/2010 |
| WO | WO 2010/028277 A1 | 3/2010 |
| WO | WO 2010/045651 A1 | 4/2010 |
| WO | WO 2010/135608 A1 | 11/2010 |

OTHER PUBLICATIONS

Crans-Vargas, et al. CREB as a prognostic marker in acute leukemia. Abstract. Blood. 2001; 98(11), part 1, p. 316a.

European search report and search opinion dated Feb. 22, 2011 for Application No. 10180167.8.

Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.

Kornblau, et al. Dynamic single-cell network profiles in acute myelogenous leukemia are associated with patient response to standard induction therapy. Clin Cancer Res. Jul. 15, 2010;16(14):3721-33. (abstract).

Krutzik, et al. Analysis of protein phosphorylation and cellular signaling events by flow cytometry: techniques and clinical applications. Clinical Immunology. 2004; 110: 206-21.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].

Perez, et al. LFA-1 signaling through p44/42 is coupled to perforin degranulation in CD56+CD8+ natural killer cells. Blood. Aug. 15, 2004;104(4):1083-93.

Perez, et al. Simultaneous measurement of multiple active kinase states using polychromatic flow cytometry. Nat Biotechnol. 2002; 20: 155-62.

Rosen, et al. Functional characterization of FLT3 receptor signaling deregulation in acute myeloid leukemia by single cell network profiling (SCNP). PLoS One. Oct. 27, 2010;5(10):e13543.

Shankar, et al. CREB is amplified in AML blasts and is associated with an increased risk of relapse and decreased event-free survival. Abstract. Blood. 2004; 104(11), Part 1, p. 166A.

Shankar, et al. Role of cyclic AMP response element binding protein in human leukemias. Cancer. Nov. 1, 2005;104(9):1819-24.

Shankar, et al. The role of CREB as a proto-oncogene in hematopoiesis and in acute myeloid leukemia. Cancer Cell. Apr. 2005;7(4):351-62.

Spiekermann, et al. Overexpression and constitutive activation of FLT3 induces STAT5 activation in primary acute myeloid leukemia blast cells. Clinical Cancer Research. Jun. 2003; 9:2140-2150.

UK office action and search report dated Feb. 22, 2011 for GB Application No. 1017857.2.

Zheng, et al. Regulation of STAT3 and STAT5 in the differentiation of FLT3/ITD expressing 32Dc13 cells induced by G-CSF and CEP-701. Abstract 2935.Blood. 2002; 100(11) and 44th Annual Meeting of the American Society of Hematology. Philadelphia, PA, USA. Dec. 6-10, 2002.

Benekli, et al. Signal transducer and activator of transcription proteins in leukemias.Blood. Apr. 15, 2003;101(8):2940-54.

Birkenkamp, et al. Regulation of constitutive STAT5 phosphorylation in acute myeloid leukemia blasts. Leukemia. 2001; 15(12):1923-31.

Chow, et al. Constitutive phosphorylation of the S6 ribosomal protein via mTOR and ERK signaling in the peripheral blasts of acute leukemia patients. Experimental hematology. 2006; 34(9):1182-1190.

U.S. Appl. No. 13/384,181, filed Jan. 13, 2012, Cesano et al.
U.S. Appl. No. 61/079,537, filed Jul. 10, 2008, Santosh Putta.
U.S. Appl. No. 61/104,666, filed Oct. 10, 2008, Nolan, Gary.
U.S. Appl. No. 61/106,462, filed Oct. 17, 2008, Fantl, Wendy.
U.S. Appl. No. 61/108,803, filed Oct. 27, 2008, Covey, Todd.
U.S. Appl. No. 61/113,823, filed Nov. 12, 2008, Nolan et al.
U.S. Appl. No. 61/120,320, filed Dec. 5, 2008, Fantl et al.
U.S. Appl. No. 61/144,684, filed Jan. 14, 2009, Fantl et al.
U.S. Appl. No. 61/144,955, filed Jan. 15, 2009, Parkinson et al.
U.S. Appl. No. 61/146,276, filed Jan. 21, 2009, Parkinson et al.
U.S. Appl. No. 61/151,387, filed Feb. 10, 2009, Fantl et al.
U.S. Appl. No. 61/155,373, filed Feb. 25, 2009, Fantl, Wendy.
U.S. Appl. No. 61/156,754, filed Mar. 2, 2009, Fantl et al.
U.S. Appl. No. 61/157,900, filed Mar. 5, 2009, Fantl, Wendy.
U.S. Appl. No. 61/162,598, filed Feb. 23, 2009, Covey et al.
U.S. Appl. No. 61/162,673, filed Mar. 23, 2009, Soper et al.
U.S. Appl. No. 61/170,348, filed Apr. 17, 2008, Fantl et al.
U.S. Appl. No. 61/176,420, filed May 7, 2009, Purvis, Norman.
U.S. Appl. No. 61/177,935, filed May 13, 2009, Fantl et al.
U.S. Appl. No. 61/181,211, filed May 26, 2009, Covey et al.
U.S. Appl. No. 61/182,518, filed May 29, 2009, Fantl et al.
U.S. Appl. No. 61/182,638, filed May 29, 2009, Fantl et al.
U.S. Appl. No. 61/186,619, filed Jun. 12, 2009, Fantl et al.
U.S. Appl. No. 61/216,825, filed May 20, 2009, Fantl et al.
U.S. Appl. No. 61/218,718, filed Jun. 19, 2009, Fantl et al.
U.S. Appl. No. 61/226,878, filed Jul. 20, 2009, Fantl et al.

Bruggemann et al. Human Antibody Production in Transgenic Mice : Expression from 100 kb of the Huamn IgH Locus.Eur. J. Immunol. 1991. 21:1323-1326.

Carter et al. Humanization of an Anti-p185 Her2 Antibody for human Cancer Therapy. Proc Natl. Acad Sci USA. 1992. 89:4285-4289.

Chalfie et al. Green fluorescent protein as a marker for gene expression. Science. 1994. 263(5148):802-5.

Clark, Antibody Humanization: A Case of the Emperor's New Clothes? Immunol Today. 2000. 21(8):397-402.

Kitts. Cloning vector pEGFP-N1, complete sequence, enhanced green fluorescent protein (egfp) and neomycin phosphotransferase genes, complete cds. Clontech—Genbank Accession No. U55762. 1996. Genbank.

Griffiths et al. Strategies for selection of antibodies by Phage Display. Curr Opin Biotechnol. 1998. 9:102-108.

Hanahan D. et al. The Hallmarks of Cancer. Cell. 2000. 100(1):57-70.

Heim et al. Engineering green fluorescent protein for improved brightness, longer wavelengths and fluorescence resonance energy transfer. Curr Biol. 1996, 6(2):178-82.

Ichiki et al. Regulation of the expression of human C epsilon germline transcript. Identification of a novel IL-4 responsive element. J Immunol. 1993. 150(12):5408-17.

Irish et al. Mapping normal and cancer cell signaling networks: towards single-cell proteomics. Nature. 2006. 6:146-155.

Irish et al. FLt3 ligand Y591 duplication and Bcl-2 over expression are detected in acute myeloid leukemia cells with high levels of phosphorylated wild-type p53. Neoplasia. 2007. 109(6):2589-96.

Irish et al. Single cell profiling of potentiated phospho-protein networks in cancer cells, Cell. 2004. 118(2):217-18.

Jones et al. Replacing the complementarity-determining regions in a human antibody with those from a mouse. Nature. 1986. 321(6069):522-5.

Krutzik et al. High-content single-cell drug screening with phosphospecific flow cytometry. Nature Chemical Biology. 2007. 4:132-142.

Krutzik et al. Fluorescent cell barcoding in flow cytometry allows high-throughput drug screening and signaling profiling. Nature Methods. 2006. 3(5):361-68.

Krutzik et al. Characterization of the murine immunological signaling network with phosphospecific flow cytometry. J Immunol. 2005. 175(4):2366-73.

Krutzik et al. Coordinate analysis of murine immune cell surface markers and intracellular phosphoproteins by flow cytometry. J Immunol. 2005. 175(4):2357-65.

Krutzik et al. Intracellular phospho-protein staining techniques for flow cytometry: monitoring single cell signaling events. Cytometry A. 2003. 55(2):61-70.

Nolan et al. Fluorescence-activated cell analysis and sorting of viable mammalian cells based on beta-D-galactosidase activity after transduction of *Escherichia coli* lacZ. Proc Natl Acad Sci U S A. 1988. 85(8):2603-7.

O'Connor et al. Humanization of an antibody against human protein C and calcium-dependence involving framework residues. Protein Eng. 1998. 11(4):321-8.

Queen et al. A humanized antibody that binds to the interleukin 2 receptor. Proc Natl Acad Sci U S A. 1989. 86(24):10029-33.

Riechmann et al. Reshaping Human Antibodies for Therapy. Nature. 332:323-329, (1988).

Schulz et al. Single-cell phospho-protein analysis by flow cytometry. Curr Protoc Immunol. 2007. 78:8 8.17.1-20.

Stauber et al. Development and Applications of Enhanced Green Fluorescent Protein Mutants. Biotechniques. 1998. 24(3):462-471.

Stelzer et al.. Use of Multiparameter Flow Cytometry and Immunophenotyping for the Diagnosis and Classification of Acute Myeloid Leukemia John Wiley & Sons. 2000. Chapter 9, 215-246.

van Hest et al. Efficient Introduction of Alkene Functionality into Prteins in vivo. FEBS Lett. 1998. 428:(1-2) 68-70.

Verhoeyen et al. Reshaping Human Antibodies: Grafting an Antilysozyme Activity. Science. 1988. 239:1534-1536.

* cited by examiner

KITS FOR MULTIPARAMETRIC PHOSPHO ANALYSIS

CROSS-REFERENCE

This application claims the priority of U.S. Provisional App. Ser. No. 61/162,673, filed on Mar. 23, 2009 and U.S. Provisional App. Ser. 61/245,000, filed on Sep. 23, 3009 the disclosures of which are hereby incorporated by reference their entirety for all purposes.

BACKGROUND

Multiparametric analyses of cells provide an approach for the simultaneous determination of the activation states of a plurality of cellular components. The activation status of the plurality of cellular components can be measured after exposure of cells to extracellular modulators and in so doing allows the signaling capacity of signaling networks to be determined when compared to the activation status of those networks in the absence of such modulators. The induced activation status of a protein rather than the frequently measured basal phosphorylation state of a protein has been shown in several studies to be more informative, as it takes into account (and reveals) signaling deregulation that is the consequence of numerous cytogenetic, epigenetic and molecular changes characteristic of transformed cells. For example, multiparameter flow cytometry at the single cell level can measure the activation status of multiple intracellular signaling proteins and can assign activation states of these molecules to the varied cell sub-sets within complex primary cell populations.

However, usually multiparametric analyses of cells, e.g., multiparametric flow cytometry, require the use of multiple reagents at precise concentrations to produce robust and reproducible results. Since these data can be used as tools to inform clinical decisions, as well as therapeutic development, it would be beneficial to provide kits comprised of components relevant to a particular application with accompanying relevant usage information.

Protein phosphorylation is a critical post translational process in controlling many cell functions such as migration, apoptosis, proliferation and differentiation. Site specific phosphorylation of proteins can be detected, for example, by incubating cells with fluorochrome-conjugated phospho-specific antibodies using flow cytometry. However, only reagents whose parameters (including but not limited to, concentration, kinetics, fluorochrome to protein ratio) have been optimized can be used to generate robust and reproducible data that can be applied to a specific purpose. Kits comprising two or more reagents recognizing intracellular markers and/or extracellular markers along with an appropriate modulator or modulators to evoke a signaling response appropriate for the signal transduction pathway, specific cell type, disease state, or cellular function can save the end user from the tedious and often costly process of selecting, optimizing and standardizing reagents thereby providing the user with a more streamlined and cost-saving approach for profiling cellular networks in single cells.

It is therefore an objective of the present invention to provide kits that meet such demands.

SUMMARY OF THE INVENTION

The present invention involves the preparation of kits to be utilized in multi-parametric analyses (e.g. flow cytometry) on cell populations for the identification of the activation states of cellular signaling molecules (called nodes) in cells. Profiles of node states in cell populations are useful for diagnosis, prognosis, drug discovery, drug development, patient stratification (for example, who will and who will not respond to a drug) and other applications. Methods for determining cell populations and activation states have been disclosed in U.S. Pat. Nos. 7,381,535, 7,393,656, 7,563,584 and U.S. Ser. No. 61/120,320, which are hereby incorporated by reference in their entirety.

One embodiment of the present invention is a kit comprising a combination of binding element cell surface markers and state-specific intracellular markers. The kit can also comprise one or more modulators, therapeutic agents, fixatives, buffers, physical devices and software as described below.

In some embodiments, kits can be directed toward applications such as prediction of a response to a therapeutic agent, diagnosis and prognosis of various diseases or conditions, profiling signaling in specific cell types, analyzing the functional effects of genetic mutations, etc.

In some embodiments, kits can be prepared based on cell types of interest. For example, a kit can have a panel of antibodies that recognize extracellular markers specific to T cells, B cells, myeloid cells, stromal cells, neuronal cells or epithelial cells.

In some embodiments, the cell-type-specific kits can be supplemented with modulators for different signaling pathways. For example, the kit can include one or more cytokines and or growth factors that activate pathways including, but not limited to, JAK/STAT, PI3K/Akt, Ras/Raf/Erk, phosphatase signaling, metabolism, apoptosis, DNA damage response or transcriptional activation pathways. The kits can further comprise control cells, compounds and/or protocols.

In some embodiments, the invention involves kits for analyzing the effect of a compound on a cancer cell, comprising one or more binding elements that recognize particular surface markers expressed by cells in certain disease states. The kits can also comprise a compound used for treating a condition such as cancer. The kits can also comprise binding elements recognizing the activated state of signaling elements that can be activated in response to a compound, including but not limited to phosphorylated, acetylated, methylated or cleaved proteins.

In some other embodiments of the present invention, kits can additionally comprise consumable hardware, such as plates for holding the reagents or performing reactions, pipette tips, and software or files required to carry out the experiment. In some embodiments, the kit can further comprise a software package for data analysis of cell signaling profiles, which can include reference profiles for comparison with a test profile. The kit can also include software to manage or perform the experiment, including the use of the reagents and protocols for conducting appropriate reactions.

In some other embodiments, kits of the present invention enable the detection of activatable elements by sensitive cellular assay methods, such as immunohistochemistry and flow cytometry, which are suitable for clinical applications in detection, prognosis, and screening of cells and tissues from patients who have a disease involving aberrant signaling networks, for example leukemia.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

INCORPORATION BY REFERENCE

Figure 1:
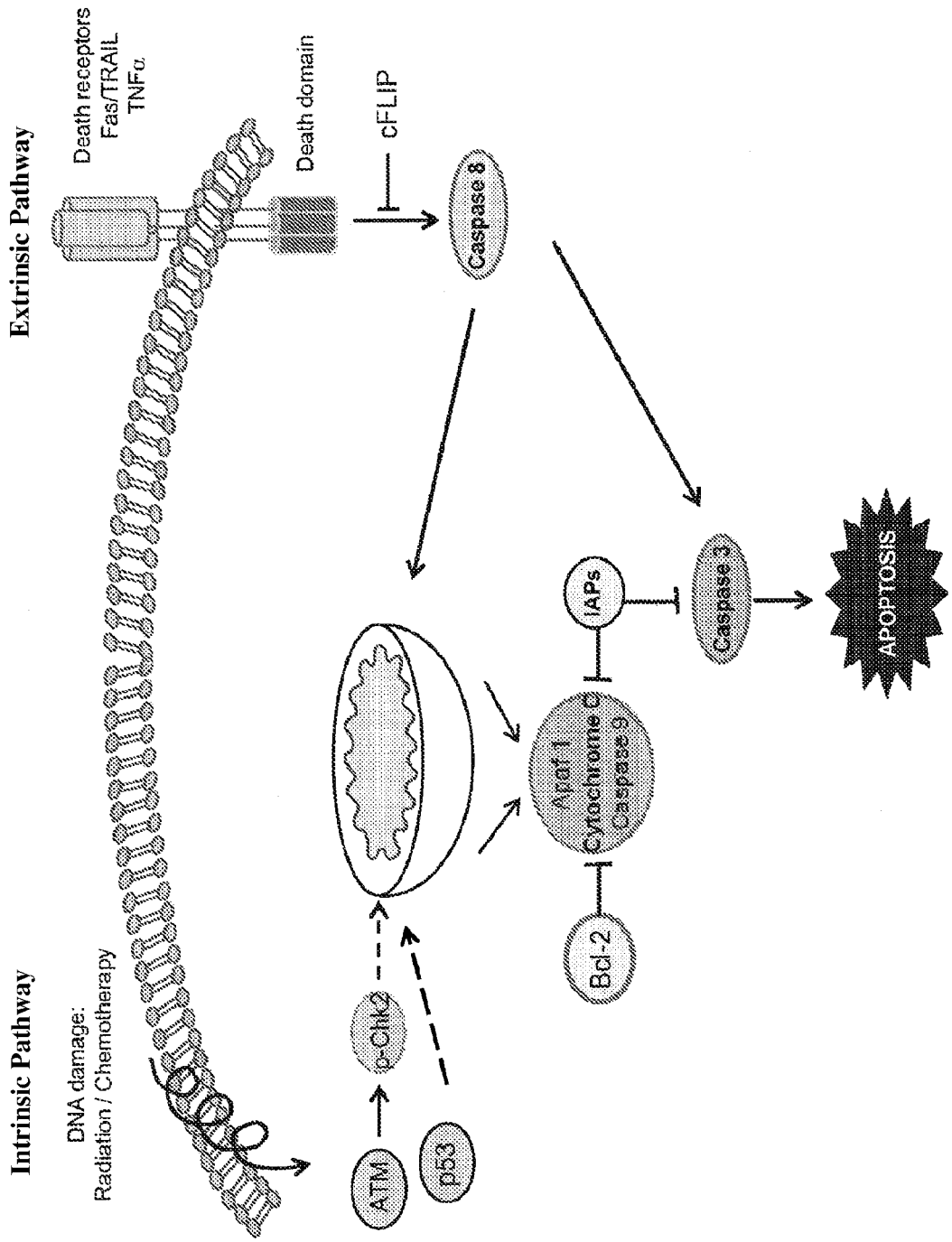
FIG. 1 illustrates some embodiments of apoptosis pathway kits, comprising various intracellular markers involved in intrinsic and extrinsic apoptosis pathways.
Figure 2:
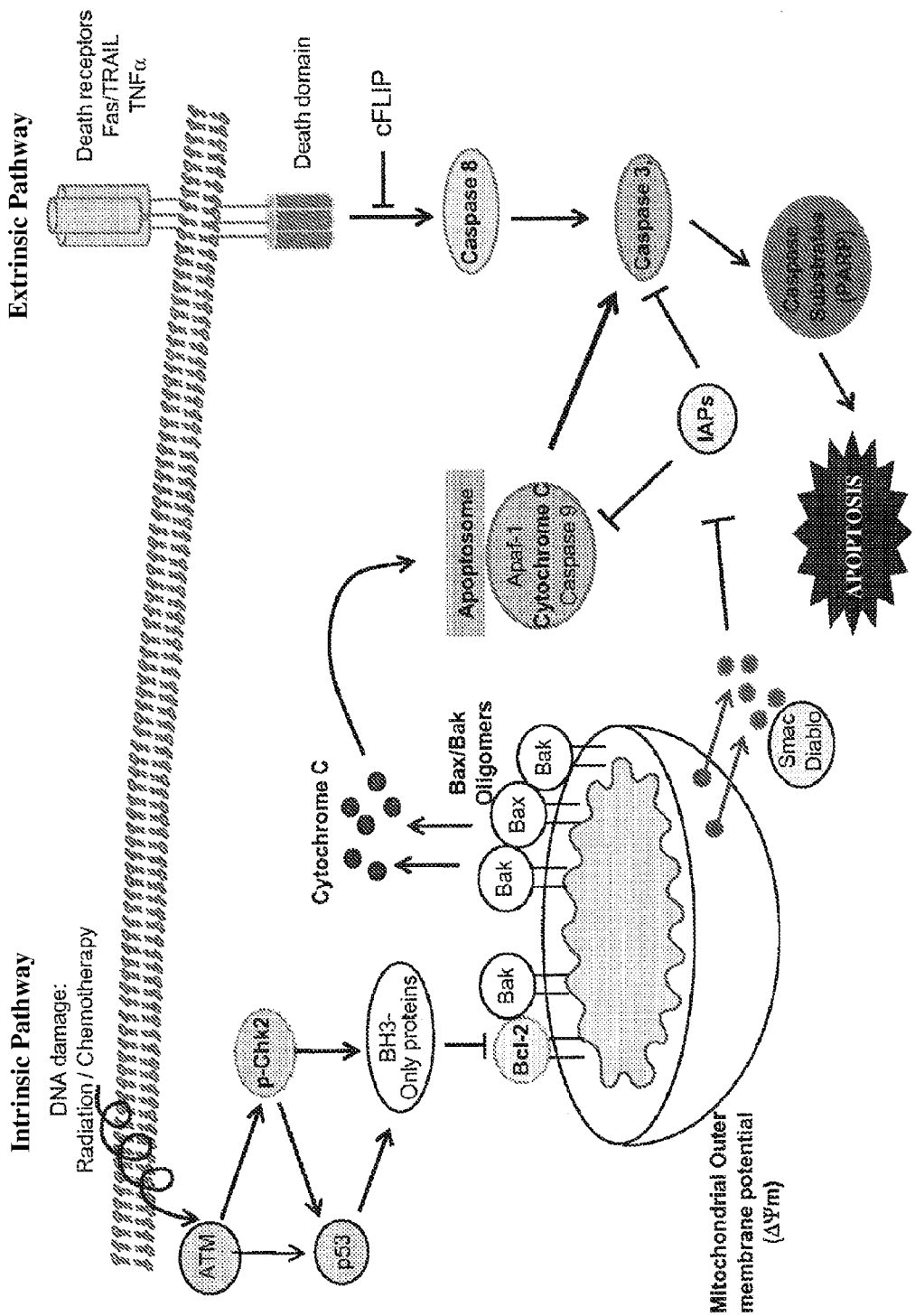
FIG. 2 illustrates some embodiments of apoptosis pathway kits, comprising various intracellular markers involved in intrinsic and extrinsic apoptosis pathways.

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention incorporates information disclosed in other applications and texts. The following patent and other publications are hereby incorporated by reference in their entireties: Haskell et al., Cancer Treatment, 5$^{th}$ Ed., W.B. Saunders Co. (2001); Alberts et al., Molecular Biology of the Cell, 4$^{th}$ Ed., Garland Science (2002); Vogelstein and Kinzler, The Genetic Basis of Human Cancer, 2d Ed., McGraw Hill (2002); Michael, Biochemical Pathways, John Wiley & Sons (1999); Weinberg, The Biology of Cancer (2007); Janeway et al., Immunobiology, 7$^{th}$ Ed., Garland Science (2008); Leroith & Bondy, Growth Factors and Cytokines in Health and Disease, Vols. 1A and 1B: A Multi Volume Treatise, (JAI Pr, 1996). Patents and applications that are also incorporated by reference in their entirety include U.S. Pat. Nos. 7,381,535; 7,393,656; 7,563,584 and U.S. patent Ser. Nos. 10/193,462; 11/655,785; 11/655,789; 11/655,821; 11/338,957; 12/432,720; 12/229,476; 12/432,239; 12/460,029; 12/471,158; 61/216,825; 61/162,673; 61/157,900; 61/151,387; 61/104,666; 61/226,878; 61/218,718; 61/182,518; 61/170,348; 61/144,684; 61/113,823; 61/181,211; 61/162,598; 61/108,803; 61/182,638; 61/177,935; 61/155,373; 12/293,081; 61/186,619; 61/156,754; 61/106,462; 61/176,420; 12/538,643; 12/501,274; 61/079,537; 12/501,295; 61/146,276; and 61/144,955. Some commercial reagents, protocols, software and instruments that are useful in some embodiments of the present invention are available at the Becton Dickinson Website http://www.bdbiosciences.com/features/products/, and the Beckman Coulter website, http://www.beckmancoulter.com/Default.asp?bhfv=7. Method of performing assays on multiparametric flow cytometry are described in e.g., Krutzik et al., High-content single-cell drug screening with phospho-specific flow cytometry, Nature Chemical Biology (2007) 4:132-142; Irish et al., FLt3 ligand Y591 duplication and Bcl-2 over expression are detected in acute myeloid leukemia cells with high levels of phosphorylated wild-type p53, Neoplasia (2007) 109(6):2589-96; Irish et al. Mapping normal and cancer cell signaling networks: towards single-cell proteomics, Nature (2006) 6:146-155; Irish et al., Single cell profiling of potentiated phospho-protein networks in cancer cells, Cell (2004) 118(2):217-18; Schulz, K. R. et al., Single-cell phospho-protein analysis by flow cytometry, Curr Protoc Immunol. (2007) 78:8 8.17.1-20; Krutzik, P. O. et al., Coordinate analysis of murine immune cell surface markers and intracellular phosphoproteins by flow cytometry, J Immunol. (2005) 175(4):2357-65; Krutzik, P. O. et al., Characterization of the murine immunological signaling network with phosphospecific flow cytometry, J Immunol. (2005) 175(4):2366-73; Stelzer et al., Use of Multiparameter Flow Cytometry and Immunophenotyping for the Diagnosis and Classification of Acute Myeloid Leukemia (John Wiley & Sons, 2000); Krutzik, P. O. et al., Intracellular phospho-protein staining techniques for flow cytometry: monitoring single cell signaling events, Cytometry A. (2003) 55(2):61-70; Hanahan D. et al., The Hallmarks of Cancer, Cell (2000) 100(1):57-70; Krutzik et al, High content single cell drug screening with phospho-specific flow cytometry, Nature Chemical Biology (2008) 4(2):132-42. Experimental and process protocols and other helpful information can be found at http:/proteomices.stanford.edu. The articles and other references cited below are also incorporated by reference in their entireties for all purposes.

The present invention relates to the processing of cells for analysis. More specifically, the present invention relates to kits comprising binding elements that can be used, e.g., in multi-parametric flow cytometry in order to determine the activation states of a plurality of proteins in single cells.

In one aspect, the present invention provides a kit comprising one or more binding elements for extracellular markers specifically targeted toward certain diseases, cell types and signaling pathways, which can be used, for example, to facilitate research. A kit of the invention can allow for analysis of relevant activatable elements in specific cell types that can provide the information necessary to make a diagnosis, prognosis, drug discovery, predict the response of disease to a therapeutic agent, and provide information relevant to drug development and patient stratification to a specific condition.

In another aspect, the present invention provides a kit comprising one or more binding elements that recognize one or more cell surface markers and one or more intracellular markers to enable rapid screening of the effects of modulators or therapeutic agents on evoked cell signaling.

In yet another aspect, the present invention provides a kit with one or more binding elements and one or more modulators to develop one or more network profiles, such as a network profile that can predict a response to a therapeutic agent or therapeutic regimen.

In some embodiments, the present invention relates to a kit and/or composition to be used in multiparametric flow cytometry on cell populations and activation states for diagnosis, prognosis, drug discovery, drug development, and patient stratification. A kit can comprise one or more binding elements for the cell surface marker of particular cell type or disease state. A kit can also comprise one or more binding elements that recognize intracellular markers of particular cellular pathway or function, modulators, labeling agent, fixatives, permeabilizing agents, etc. The kit generally can be used for determining the status of an activatable element. The kit might also be used for determining the status of a plurality of activatable elements.

A kit of the present invention can include components necessary to determine the activation state of a plurality of activatable elements from single cells, wherein each cell type is selected based on a target disease cellular state or other area of interest. For example, the target diseases can include, but are not limited to hematological diseases such as acute myeloid leukemia (AML), chronic lymphocytic leukemia (CLL), myelodysplastic syndrome (MDS), myeloproliferative neoplasm (MPN); the target states and pathways can include, but are not limited to intrinsic apoptosis pathway, extrinsic apoptosis pathway, DNA damage-induced apoptosis pathway, ABL and BCR/ABL function in CML (chronic myelogenous leukemia), phosphatase function, calcium signaling, Protein Kinase C (PKC) function.

In one embodiment, a kit can be used to monitor and predict disease outcome. In another embodiment, a kit can be used in drug screening to determine whether a drug can be useful for treating a particular disease. In some other embodiments, a kit can also be used in the analysis of drug transport and/or drug metabolism, inflammation, autophagy, metabolism, cell proliferation, cell cycle, cell survival, siRNA function, or other functional characteristic.

A kit can also provide a panel of reagents for the analysis of a targeted therapeutic agent. For example, it could be used to study the effect of aJAK2 inhibitor on JAK/STAT pathway activity; PI3K inhibitor on PI3K/Akt or Ras/Raf/Erk pathway activity; Mek inhibitor on Ras/Raf/Erk pathway activity; mTor inhibitor on the TSC/mTor pathway; IK-Kinase inhibitor on NFkB pathway activity; kinase inhibitor acting on a pathway utilizing a tyrosine kinase, including but not limited to, epidermal growth factor receptor, Fibroblast growth factor, and Src family kinase signaling and nucleoside analogues and alkylating agents on the DNA damage response and apoptosis pathways.

A kit can include a composition for the detection of the activation of an element in a cell. A suitable cell includes cell types implicated in a wide variety of disease conditions, even in non-diseased states. Suitable cell types include, but are not limited to, cancer cells of all types including cancer stem cells, cardiomyocytes, dendritic cells, endothelial cells, epithelial cells, lymphocytes (T cell and B cell), mast cells, eosinophils, basophils, neutrophils, natural killer cells, erythrocytes, hepatocytes, leukocytes including mononuclear leukocytes, stem cells such as hematopoietic, neural, skin, and monocyte stem cells. Particularly preferred are primary disease state cells, such as primary cancer cells including circulating tumor cells (CTCs).

One embodiment of the present invention is a kit for classifying cells of a myeloid disorder based on the biology of a cell or group of cells derived from a patient with a myeloid malignancy such as AML, MDS, or MPN.

In some embodiments, the kit of the present invention can be directed towards a particular cell type. Specific examples include, but are not limited to, lymphocytes, myeloid cells, such as mature monocytes (CD45+, CD33+, CD11b+), myeloblasts (CD45+, CD34+, CD11b−), lymphoid subsets, such as T cell, B cell, and nucleated red blood cells (nRBCs).

In some embodiments, a kit of the present invention can be geared towards a particular sample, such as peripheral blood and bone marrow. In some preferred embodiments, the cells used in the present invention are populations of leukemic myeloid cells taken from the bone marrow of a leukemic patient or nucleated red blood cells taken from the bone marrow of a leukemic patient.

The terms "patient" or "individual" as used herein includes humans as well as other mammals.

Cell Surface Markers

Cell surface markers are molecules characteristic of the plasma membrane of a cell or in some cases of a specific cell type. The term "extracellular marker" and "cell surface marker", and "cell surface antigen" and "phenotypic marker" as used herein, include antigens expressed in healthy and/or diseased cells and can be used interchangeably. In some embodiments, a kit of the present invention can comprise a combination of antibodies that recognize cell surface markers including but not limited to CD3, CD4, CD7, CD8, CD11b, CD11c, CD14, CD15, CD16, CD19, CD20, CD22, CD25, CD27, CD33, CD34, CD38, CD40, CD45, CD56, CD69, CD71, CD80, CD117, CD138, CD235a, CD235b, Ter119, GP-130, IgM, IgD, IgE, IgG, IgA, CCR5, CCR3, TLR2, TLR4, TLR9. CD3, also known as T3, is a member of the immunoglobulin (Ig) superfamily that plays a role in antigen recognition, signal transduction and T cell activation. It is found on all mature T lymphocytes, NK-T cells, and some thymocytes. CD4 is also a member of the Ig superfamily, which participates in cell-cell interactions, thymic differentiation, and signal transduction. It is primarily expressed on most thymocytes, a subset of T cell and monocytes/macrophages. CD7 is found on T cells, NK cells, thymocytes, hematopoietic progenitors and monocytes. CD7 is also expressed on ALL and some AML cells. CD11b is a member of the integrin family, primarily expressed on granulocytes, monocytes/macrophages, dendritic cells, NK cells, and subsets of T and B cells. CD14 is a GPI-linked membrane glycoprotein, also known as LPS receptor. It is expressed at high levels on macrophages, monocytes and at low level on granulocytes. CD33 is a sialoadhesion Ig superfamily member expressed on myeloid progenitors, monocytes, granulocytes, dendritic cells and mast cells. It is absent on normal platelets, lymphocytes, erythrocytes and hematopoietic stem cells. CD34 is a type I monomeric sialomucin-like glycophosphoprotein. It is selectively expressed on the majority of hematopoietic stem/progenitor cells, bone marrow stromal cells, capillary endothelial cells, embryonic fibroblasts, and some nervous tissues. It is commonly used marker for identifying human hematopoietic stem/progenitor cells. CD45 is commonly known as the leukocyte common antigen. It is a transmembrane tyrosine phosphatase expressed on all hematopoietic cells, except erythrocytes and platelets. It is a signaling molecule that regulates a variety of cellular processes including cell growth, differentiation, cell cycle, and oncogenic transformation. It plays a critical role in T and B cell antigen receptor-mediated activation. CD71 is a type II heterodimeric transmembrane glycoprotein also known as the transferring receptor. It is expressed on proliferating cells, reticulocytes, and erythroid precursors. CD71 plays a role in the control of cellular proliferation by facilitating the uptake of iron via ferrotransferrin binding and the recycling of apotransferrin to the cell surface. CD235a is also known as glycophorin A and CD235b is also known as glycophorin B, major sialoglycoproteins expressed on the red blood cell membrane and erythroid precursors. Mature, non-nucleated red blood cells are characteristically CD235a and/or CD235b positive, but CD45 and CD71 negative.

In some embodiments, a kit to be used for the analysis of myeloid cells in bone marrow can comprise antibodies that recognize 1, 2, 3, 4, 5, 6 or 7 of the following: CD7, CD11b, CD14, CD15, CD33, CD34, and/or CD45.

In some embodiments, a kit to be used for the analysis of nucleated red blood cells can comprise antibodies that recognize 1, 2, 3, 4, 5 or 6 of the following: CD7, CD14, Cd34, CD45, CD71, CD235a and/or CD235b.

State-specific Binding Elements for Intracellular Markers

In some embodiments, the kits of the invention are employed to monitor the status of an activatable element, such as a signaling protein, in a signaling pathway known in the art including those described herein. Exemplary types of signaling proteins within the scope of the present invention include, but are not limited to, kinases, kinase substrates (e.g. phosphorylated substrates), phosphatases, phosphatase substrates, binding proteins (such as 14-3-3), receptor ligands and receptors (cell surface receptor tyrosine kinases and nuclear receptors)). Kinases and protein binding domains, for example, have been well described. See, for example, Cell Signaling Technology, Inc., 2002 Catalogue "The Human Protein Kinases" and "Protein Interaction Domains" pgs. 254-279).

In some embodiments, a kit can comprise one or more of the state-specific binding elements specific for the activated element(s) of interest. Exemplary binding elements comprise binding elements specific for PI3-Kinase (p85, p110a, p110b, p110d), JAK1, JAK2, SOCs, Rae, Rho, Cdc42, Ras-GAP, Vav, Tiam, Sos, Dbl, Nck, Gab, PRK, SHP1, and SHP2, SHIP1, SHIP2, sSHIP, PTEN, Shc, Grb2, PDK1, SGK, Akt1, Akt2, Akt3, TSC1,2, Rheb, mTor, 4E-BP1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLC-γ1, PLC-γ2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, Histone H3, HATs, HDACs, PKR, Rb, Cyclin D, Cyclin E, Cyclin A, Cyclin B, p15, p16, p21, p14Arf, p27KIP, p21CIP, Cdk4, Cdk6, Cdk7, Cdk1, Cdk2, Cdk9, Cdc25, A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, XIAPs, Smac, Fodrin, Actin, Src, Lyn, Fyn, Lck, NIK, IκB, p65(RelA), IKKα, PKA, PKCα, PKCβ, PKCθ, PKCδ, CAMK, Elk, AFT, Myc, Egr-1, NFAT, ATF-2, Mdm2, p53, DNA-PK, Chk1, Chk2, ATM, ATR, beta-catenin, CrkL, GSK3α, GSK3β, FOXO, or glycolytic enzymes including but not limited to M2 pyruvate kinase.

In some preferred embodiments, kits of the present invention comprise one or more of the state-specific binding elements specific for the proteins selected from the group consisting of STAT 1, STAT3, STAT5, S6, Erk, Akt, ATM, ATR, Chk1, Chk2, 53BP1, PARP, H2AX, Caspase 3, Caspase 8, CRKL, Histone H3, Cyclin B1, Cyclin D1, Cyclin E, Cyclin A, p15, p16, p21, PLCδ2, p53, SLP-76, and CREB. Other binding elements disclosed in U.S. Pat. No. 7,393,656 are also incorporated here by reference.

Binding Element

In some embodiments of the invention, a kit of the invention can comprise one or more binding elements specific for activation states of activatable elements. The term "binding element" includes any molecule, e.g., peptide, nucleic acid, small organic molecule which is capable of detecting an activation state of an activatable element over another activation state of the activatable element.

In some embodiments, the binding element is a peptide, polypeptide, oligopeptide or a protein. The peptide, polypeptide, oligopeptide or protein can be made up of naturally occurring amino acids and peptide bonds, or synthetic peptidomimetic structures, or a combination of both. Thus "amino acid", or "peptide residue", as used herein include both naturally occurring and synthetic amino acids. For example, homo-phenylalanine, citrulline and noreleucine are considered amino acids for the purposes of the invention. The side chains may be in either the (R) or the (S) configuration. In some embodiments, the amino acids are in the D- or L-configuration. If non-naturally occurring side chains are used, non-amino acid substituents can be used, for example to prevent or retard in vivo degradation. Proteins including non-naturally occurring amino acids can be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

A kit of the present invention can be used to detect any particular activatable element in a sample that is antigenically detectable and antigenically distinguishable from other activatable elements which are present in the sample. For example, activation state-specific antibodies can be used in the present kits to identify distinct signaling cascades within a subset or subpopulation of cells within a complex population, and the ordering of protein activation (e.g., kinase activation) in potential signaling hierarchies. Hence, in some embodiments, the expression and phosphorylation of one or more polypeptides can be detected and quantified using a kit of the present invention. In some embodiments, the expression and phosphorylation of one or more polypeptides that are cellular components of a cellular pathway can be detected and quantified using methods of the present invention. As used herein, the term "activation state-specific antibody" or "activation state antibody" or grammatical equivalents thereof, refer to an antibody that specifically binds to a corresponding and specific antigen. Preferably, the corresponding and specific antigen is a specific form of an activatable element. Also preferably, the binding of the activation state-specific antibody is indicative of a specific activation state of a specific activatable element.

In some embodiments, the binding element is an antibody. In some embodiment, the binding element is an activation state-specific antibody.

The term "antibody" includes full length antibodies and antibody fragments, and may refer to a natural antibody from any organism, an engineered antibody, or an antibody generated recombinantly for experimental, therapeutic, or other purposes as further defined below. Examples of antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, partial antagonists, agonists, partial agonists or neutralizing antibodies.

The antibodies of the present invention may be nonhuman, chimeric, humanized, or fully human. For a description of the concepts of chimeric and humanized antibodies see Clark et al., 2000 and references cited therein (Clark, 2000, Immunol Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In some embodiments, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, Nature 321:522-525; Riechmann et al., 1988, Nature 332:323-329; Verhoeyen et al., 1988, Science, 239:1534-1536). Additional examples of humanized murine monoclonal antibodies are also known in the art, for example antibodies binding human protein C (O'Connor et al., 1998, Protein Eng 11:321-8), interleukin 2 receptor (Queen et al., 1989, Proc Natl Acad Sci, USA 86:10029-33), and human epidermal growth factor receptor 2 (Carter et al., 1992, Proc Natl. Acad Sci USA 89:4285-9). In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, Curr Opin Biotechnol 8:455-458) or human antibody libraries coupled with selection methods (Griffiths et al., 1998, Curr Opin Biotechnol 9:102-108).

Specifically included within the definition of "antibody" are aglycosylated antibodies. By "aglycosylated antibody" as used herein is meant an antibody that lacks carbohydrate attached at position 297 of the Fc region, wherein numbering is according to the EU system as in Kabat. The aglycosylated antibody may be a deglycosylated antibody, which is an antibody for which the Fc carbohydrate has been removed, for example chemically or enzymatically. Alternatively, the aglycosylated antibody may be a nonglycosylated or unglycosylated antibody, that is an antibody that was expressed without Fc carbohydrate, for example by mutation of one or residues that encode the glycosylation pattern or by expression in an organism that does not attach carbohydrates to proteins, for example bacteria.

Activation state specific antibodies can be used to detect kinase activity, however additional means for determining kinase activation are provided by the present invention. For example, substrates that are specifically recognized by protein kinases and phosphorylated thereby are known. Antibodies that specifically bind to such phosphorylated substrates but do not bind to such non-phosphorylated substrates (phospho-substrate antibodies) may be used to determine the presence of activated kinase in a sample.

In a further embodiment, a kit of the invention can include a multiplicity of activation state antibodies that have been immobilized to determine an element activation profile. Antibodies can be non-diffusibly bound to an insoluble support having isolated sample-receiving areas (e.g. a microtiter plate, an array, etc.). The insoluble supports can be made of any composition to which the compositions can be bound, readily separated from soluble material, and otherwise compatible with the overall method of screening. The surface of such supports can be solid or porous and of any convenient shape. Examples of suitable insoluble supports include microtiter plates, arrays, membranes, and beads. These are typically made of glass, plastic (e.g., polystyrene), polysaccharides, nylon or nitrocellulose, or Teflon™, or other known suitable material. Microtiter plates and arrays are convenient because a large number of assays can be carried out simultaneously, using small amounts of reagents and samples. In some cases magnetic beads and the like can be included.

The particular manner of binding of the composition is not crucial so long as it is compatible with the reagents and overall kits of the invention, maintains the activity of the composition and is nondiffusable. Methods of binding include the use of antibodies (which do not sterically block either the ligand binding site or activation sequence when the protein is bound to the support), direct binding to "sticky" or ionic supports, chemical crosslinking, the synthesis of the antibody on the surface, etc. Following binding of the antibody, excess unbound material is removed by washing. The sample receiving areas can then be blocked through incubation with bovine serum albumin (BSA), casein or other innocuous protein or other moiety.

The antigenicity of an activated isoform of an activatable element can be distinguishable from the antigenicity of a non-activated isoform of an activatable element or from the antigenicity of an isoform of a different activation state. In some embodiments, an activated isoform of an element possesses an epitope that is absent in a non-activated isoform of an element, or vice versa. In some embodiments, this difference is due to covalent addition of moieties to an element, such as phosphate moieties, or due to a structural change in an element, as through protein cleavage, or due to an otherwise induced conformational change in an element which causes the element to present the same sequence in an antigenically distinguishable way. In some embodiments, such a conformational change causes an activated isoform of an element to present at least one epitope that is not present in a non-activated isoform, or to not present at least one epitope that is presented by a non-activated isoform of the element. In some embodiments, the epitopes for the distinguishing antibodies are centered around the active site of the element, although as is known in the art, conformational changes in one area of an element can cause alterations in different areas of the element as well.

Modulators

In some embodiments, the invention is directed to kits to be used for determining the activation level of one or more activatable elements in a cell upon treatment with one or more modulators. The activation of an activatable element in the cell upon treatment with one or more modulators can reveal operative pathways in a condition that can then be used, e.g., as an indicator to predict course of the condition, identify risk group, predict an increased risk of developing secondary complications, choose a therapy for an individual, predict response to a therapy for an individual, determine the efficacy of a therapy in an individual, and determine the clinical outcome for an individual.

A modulator, such as a stimulant or inhibitor, is an element that when added to a biological sample may cause a reaction in the sample, such as altering cellular components such as proteins, lipids, or nucleic acids, which can affect protein signaling networks or gene expression. For a more complete list, see the patents and applications referred to above. Modulators include chemical and biological entities, and physical or environmental stimuli. Modulators can act extracellularly or intracellularly. Chemical and biological modulators include growth factors, mitogens, cytokines, drugs, immune modulators, ions, neurotransmitters, adhesion molecules, hormones, small molecules, inorganic compounds, polynucleotides (e.g., siRNA or RNAi), antibodies, natural compounds, lectins, lactones, chemotherapeutic agents, biological response modifiers, carbohydrate, proteases and free radicals. Modulators include complex and undefined biologic compositions that may comprise cellular or botanical extracts, cellular or glandular secretions, physiologic fluids such as serum, amniotic fluid, or venom. Physical and environmental stimuli include electromagnetic, ultraviolet, infrared or particulate radiation, redox potential and pH, the presence or absences of nutrients, changes in temperature, changes in oxygen partial pressure, changes in ion concentrations and the application of oxidative stress. Modulators can be endogenous or exogenous and may produce different effects depending on the concentration and duration of exposure to the single cells or whether they are used in combination or sequentially with other modulators. Modulators can act directly on the activatable elements or indirectly through the interaction with one or more intermediary biomolecule.

Indirect modulation includes alterations of gene expression wherein the expressed gene product is the activatable element or is a modulator of the activatable element.

In some embodiments the modulator is selected from the group consisting of growth factors, mitogens, cytokines, adhesion molecules, drugs, hormones, small molecules, polynucleotides, antibodies, natural compounds, lactones, chemotherapeutic agents, immune modulators, carbohydrates, proteases, ions, reactive oxygen species, peptides, and protein fragments, either alone or in the context of cells, cells themselves, viruses, and biological and non-biological complexes (e.g. beads, plates, viral envelopes, antigen presentation molecules such as major histocompatibility complex). In some embodiments, the modulator is a physical stimuli such as heat, cold, UV radiation, and radiation.

In some embodiments, the modulator is an activator. In some embodiments the modulator is an inhibitor. In some embodiments, cells are exposed to one or more modulator.

In some embodiments, the inhibitor is an inhibitor of a cellular factor or a plurality of factors that participates in a cellular pathway (e.g. signaling cascade) in the cell. In some embodiments, the inhibitor is a phosphatase inhibitor. Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenylarsine oxide, Pyrrolidine Dithiocarbamate, and Aluminium fluoride. In some embodiments, the phosphatase inhibitor is $H_2O_2$.

Examples of modulators include but are not limited to IL-3, IL-27, IL-6, IL-10, IFN-α, IFN-γ, G-CSF, GM-CSF, EPO, TPO, FLT3L, SCF, SDF-1α, IGF, TRAIL, FASL, TNF, TNFα, Ara-C, Daunorubicin, Etoposide, Staurosporine, Imatinib and salts thereof (marketed as Gleevec), Gemtuzumab (such as Gemtuzumab ozogamicin, marketed as Mylotarg), Azacitidine (marketed as Vidaza), Decitabine (marketed as Dacogen), Vorinostat (marketed as Zolinza), and Thapsigargin, $H_2O_2$, and PMA.

Detection Elements

In some embodiments, the kits further comprise one or more detection elements, e.g., fluorescent molecules (fluorophores), that can be conjugated to the binding elements that will be used to analyze nodes by technologies including but not limited to flow cytometry. Fluorophores bound to antibody or other binding element can be activated by a laser and re-emit light of a different wavelength. The amount of light detected from the fluorophores is related to the number of binding element targets associated with the cell passing through the beam. Any specific set of detection elements, e.g. fluorescently tagged antibodies, in any embodiment can depend on the types of cells to be studied and the presence of the activatable element within those cells. Several detection elements, e.g. fluorophore-conjugated antibodies, can be used simultaneously, so measurements made as one cell passes through the laser beam consist of scattered light intensities as well as light intensities from each of the fluorophores.

Thus, the characterization of a single cell can consist of a set of measured light intensities that may be represented as a coordinate position in a multi-dimensional space. Considering only the light from the fluorophores, there is one coordinate axis corresponding to each of the detection elements, e.g. fluorescently tagged antibodies. The number of coordinate axes (the dimension of the space) is the number of fluorophores used. Modern flow cytometers can measure several colors associated with different fluorophores and thousands of cells per second. Thus, the data from one subject can be described by a collection of measurements related to the number of antigens for each of (typically) many thousands of individual cells. See Krutzik et al., High-content single-cell drug screening with phosphospecific flow cytometry. Nature Chemical Biology, Vol. 4 No. 2, Pgs. 132-42, February 2008. Such methods may optionally include the use of barcoding to increase throughput and reduce consumable consumption. See Krutzik, P. and Nolan, G., Fluorescent cell barcoding in flow cytometry allows high-throughput drug screening and signaling profiling. Nature Methods, Vol. 3 No. 5, Pgs. 361-68, May 2006.

Typically detection elements have fluorescent properties either alone or in combination with a secondary element that can be detected. Detection elements can also report through enzymatic activity, such as peroxidase activity, instead of fluorescence.

Suitable fluorescent detection elements include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263(5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12):5408-5417 (1993)), (β-galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558). All of the above-cited references are expressly incorporated herein by reference.

In some embodiments, detection elements for use in the present invention include: Alexa-Fluor dyes (an exemplary list including Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, and Alexa Fluor® 750), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantization of fluorescent probe conjugation may be assessed to determine degree of labeling and protocols including dye spectral properties are also well known in the art. In some embodiments the fluorescent label is conjugated to an aminodextran linker which is conjugated to a binding element. Additional labels listed in and are availabel through the on-line and hard copy catalogues of BD Biosciences, Beckman Coulter, AnaSpec, Invitrogen, Cell Signaling Technology, Millipore, eBioscience, Caltag, Santa Cruz Biotech, Abcam and Sigma, the contents of which are incorporated herein by reference.

Detection

The kits of the invention can provide binding elements useful for detection protocols that can be carried out by a person, such as a technician in the laboratory. Alternatively, the detection of the binding elements can be carried out using automated systems. In either case, the detection of binding elements for use according to the kits of this invention can be performed according to standard techniques and protocols well-established in the art.

One or more binding elements can be detected and/or quantified by any method that detect and/or quantitates the presence of the activatable element of interest. Such methods can include radioimmunoassay (RIA) or enzyme linked immunoabsorbance assay (ELISA), immunohistochemistry, immunofluorescent histochemistry with or without confocal microscopy, reversed phase assays, homogeneous enzyme immunoassays, and related non-enzymatic techniques, Western blots, whole cell staining, immunoelectronmicroscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Flow cytometry methods are useful for measuring intracellular parameters.

A kit of the present invention can comprise binding elements that can be analyzed by flow cytometry.

When using fluorescent detection elements in a kit of the present invention, different types of fluorescent monitoring systems, e.g., Cytometric measurement device systems, can be used to detect the binding elements. In some embodiments, a kit of the invention can be used in flow cytometric systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

In some embodiments, fluorescence of the binding elements of a kit can be measured using a fluorimeter. Other methods of detecting fluorescence can also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy.

In some embodiments, the binding elements of a kit described herein can be detected using Inductively Coupled Plasma Mass Spectrometer (ICP-MS). (Tanner et al. Spectrochimica Acta Part B: Atomic Spectroscopy, 2007 March; 62(3): 188-195.).

In some embodiments, a kit of the instant invention can be used in conjunction with an "In-Cell Western Assay." In some embodiments, the detecting can be by high pressure liquid chromatography (HPLC), for example, reverse phase HPLC, and in a further aspect, the detecting can be by mass spectrometry.

Iteratively Selecting Binding Elements, Protocols, Detection Elements and Modulators In some embodiments, the binding elements, protocols, detection elements and modulators in a kit are iteratively evaluated and selected to produce data that distinguishes the different activation states of one or more activation elements. In these embodiments, activation state data can be produced by quantifying the relative amount of the detection element associated with a binding element. The activation state data can then be analyzed to identify performance metrics that characterize the "goodness" of the activation state data. Performance metrics can include but are not limited to: a degree of separation between activation state data associated with activation states, uniformity of the activation state data associated with a same activation state, a degree of association between activation state data and a known characteristic of a cell population. Characteristics of a cell population can include but are not limited to: a cell type/sub-type of the population, a disease state of the cell population, a prognosis of the cell population, a therapeutic response of the cell population and a genotype of the cell population.

In some embodiments, the binding elements, reagents, detection elements and/or modulators are titrated over a set of increasing concentrations to produce different sets of activation state data. The activation state data is then analyzed to determine an optimal concentration of the binding elements, reagents, detection elements and/or modulators. In some embodiments, various combinations of binding elements, reagents, detection elements and modulators used to generate activation state data are evaluated.

According to the specific embodiment, different types of computational analyses can be performed to generate performance metrics based on the activation state data for the binding elements, reagents, detection elements and/or modulators. These computational analyses can be performed using program code executed by a computer comprising a memory and a processor. In most embodiments, the computer can be communicatively coupled with a machine that performs quantification of the detectable element such as a flow cytometer and/or a mass spectrometer. In some embodiments, the activation state data can be pre-processed to generate state metrics that compare the activation state data associated to control data (e.g. data derived from cells that are untreated with a modulator)

In some embodiments, the activation state data can be analyzed to characterize probability density data associated with different activation states. In some embodiments, the activation state data can be gated to identify discrete activation states associated with individual cells and the gated data can be analyzed to identify a degree of separation between the activation states and the degree of uniformity of the activation state data within a same activation states. Suitable methods of gating are outlined in U.S. patent application Ser. No. 12/501, 295, the entirety of which is incorporated herein, for all purposes. In some embodiments, histograms can be used to identify the separation between the activation states in the activation state data. Other methods for analyzing probability density data associated with different activation states include binning algorithms. Suitable binning algorithms are outlined in U.S. Publication No. 2009/0307248, the entirety of which is incorporated herein, for all purposes.

In some embodiments, the activation state data can be associated with a characteristic of a cell population and the statistical strength of the association evaluated. Different methods of evaluating the statistical strength of the association include receiver operator curves (ROC curves), correlation analysis, hazard models and classification algorithms. In some instances, the activation state data represents two activation states used to discriminate between two different cell populations. In these instances, the accuracy and sensitivity of the discrimination between the different cell populations can be also evaluated. According to the embodiments, the activation state data that is associated with the characteristic of the cell population can be based on small number of samples (e.g. a proof-of-principle experiment) or a very large number of samples (e.g. hundreds, thousands, millions of samples). In instances where a large number of samples are used, the activation state data can be derived from patient samples and associated with characteristics based on clinical data such as diagnosis, prognosis, genotype and therapeutic response.

Signaling Pathways

In some embodiments, a kit of the invention can be employed to monitor the status of an activatable element in a signaling pathway (activatable element is defined in U.S. Pat. No. 7,393,656 B2, which is hereby incorporated by reference). Signaling pathways and their members have been described extensively. See Hunter, T., Cell (2000) 100: 113-27. The activatable elements monitored include, but are not limited to, elements and regulators of the following signaling pathways: JAK/STAT, PI3K/Akt, PKC, MAP Kinase signaling (Erk, JNK and p38), Ras/Raf, Src, Notch, Hedgehog, WNT signaling pathways. Signaling pathways can be measured in the contest of chemokine signaling (including, for example SDF-1/CXCL12-CXCR4 signaling), DNA damage response, cell cycle regulation, intrinsic apoptosis, and extrinsic apoptosis. Signaling pathways may be measured in response to receptor signaling such as BCR (B cell Receptor), death receptors such as the TNFR family receptors (including, but not limited to, TNFR, TNRF2, CD30, CD40, BAFF-R, TACI, and BCMA), Toll-like Receptor (TLR), and c-KIT/Stem Cell Factor (SCF)/SCF-R (SCF-Receptor).

a. Janus Kinase (JAK)/Signal Transducers and Activators of Transcription (STAT) Pathway:

The JAK/STAT pathway mediates signaling in response to a wide variety of extracellular inputs, including numerous cytokines (See Alberts, et al, IV.15: Signaling through Enzyme-Linked Cell-Surface Receptors). Janus Kinases (JAK) are a membrane-bound receptor tyrosine kinase, and Signal Transducers and Activators of Transcriptions (STATs) are a class of transcription factor that transduce the JAK signal from the cytoplasm directly to the nucleus. Ligand binding to JAK results in receptor dimerization and activation through autophosphorylation of tyrosine residues. Activated JAK subsequently recruits STAT through its SH2 domain and activates it by phosphorylating conserved tyrosine residues, mediating the formation of STAT homodimers. STAT homodimers then translocate to the nucleus, where they act as transcriptional regulators by binding to specific DNA sequences.

There are four known JAK family members in mammals: JAK1, JAK2, JAK3 and TYK2. JAK1, JAK2 and TYK2 are expressed ubiquitously, but JAK3 is only expressed in hematopoietic cells. The JAK2V617F point mutation within the JAK2 JH2 domain, along with several mutations in exon 12 of JAK2 produce constitutive kinase activity, and are associated with myeloid malignancies (Levine, R. L. and Gilliland, D. G., Myeloproliferative disorders, Blood (2008) 112: 2190-98.). Several gain-of-function mutations in JAK3 are associated with acute megakaryoblastic myeloid leukemia (Constantinescu S. N., et al. Mining for JAK-STAT mutations in cancer. Trends Biochem Sci. (2008) 33:122-131.

There are seven members of the STAT family (STAT1, STAT2, STAT3, STAT4, STAT5a, STAT5b and STAT6) in mammals. The STAT family of proteins, especially STAT3 and STAT5, are emerging as important players in several cancers. (Yu 2004—STATs in cancer. (2008) pp. 9). Of particular relevance to AML, the STATs have been shown to be critical for myeloid differentiation and survival, as well as for long-term maintenance of normal and leukemic stem cells. (Schepers et al. STAT5 is required for long-term maintenance of normal and leukemic human stem/progenitor cells. Blood (2007) vol. 110 (8) pp. 2880-2888). STAT signaling is activated by several cytokine receptors, which are differentially expressed depending on the cell type and the stage of differentiation. Intrinsic or receptor-associated tyrosine kinases, including but not limited to JAKs, phosphorylate STAT proteins, which induces the formation of STAT homodimers. The activated STAT dimer is able to enter the cell nucleus and activate the transcription of target genes, many of which are involved in the regulation of apoptosis and cell cycle progression. Apart from promoting proliferation and survival, some growth factor receptors and signaling intermediates have been shown to play specific and important roles in myeloid differentiation. For example, G-CSFR- or TPO-induced Ras-activation promotes myeloid or megakaryocytic differentiation in the respective progenitor cells by the activation of c/EBPα (frequently inactivated in myeloid leukemia) and GATA-1, respectively. (Steffen, B. et al. Critical Reviews in *Oncology/Hematology*. 2005, vol. 56, p. 195-221).

The STAT family of proteins has been implicated in a number of cancers, and STAT3 and STAT5 have been shown to have strong oncogenic potential. (Yu, H. and Jove, R. STATs in cancer. Nat. Rev. Cancer (2008) 4: 97-105). Of particular relevance to AML, the STATs have been shown to be critical for myeloid differentiation and survival, as well as for long-term maintenance of normal and leukemic stem cells. (Schepers et al. STAT5 is required for long-term maintenance of normal and leukemic human stem/progenitor cells. Blood (2007) vol. 110 (8) pp. 2880-2888). In contrast to STAT3 and STAT5, STAT1 negatively regulates cell proliferation and angiogenesis and thereby inhibits tumor formation. Consistent with its function as a tumor suppressor, expression of STAT1 and its downstream targets is reduced in a variety of human tumors (Rawlings, J., The JAK/STAT signaling pathway, J Cell Sci. (2004) 117:1281-83, hereby fully incorporated by reference in its entirety for all purposes). Furthermore, a recent study of Primary mediastinal B-cell lymphoma (PMBL) found that 20 out of 55 (36%) PMBL patients exhibited mutations in the DNA binding domain of STAT6 (Ritz, O., et al. Recurrent mutations of the STAT6 DNA binding domain in primary mediastinal B-cell lymphoma. Blood (2009). doi:10.1182/blood-2009-03-209759).

In some embodiments, a kit of the invention can be directed to measure the JAK/STAT pathway. A kit of the invention can allow for the measurement of relevant members of the pathway such that relevant information is obtained, e.g. for the diagnosis, prognosis, patient stratification and/or selection of treatment for a condition. For instance, discovery of Janus kinase JAK2 (V617F) mutation in patients with myeloproliferative neoplasms was a major milestone in understanding the biology of those disorders. There is high incidence of this mutation in patients with myeloproliferative neoplasms: almost all patients with polycythemia vera contain the mutation and about 50% of patients with essential thrombocythemia and primary myelofibrosis have the mutation, making the development of JAK2 tyrosine kinase inhibitors a desired therapeutic goal. In some embodiments, the invention provides kits that profile p-Stat 5 and/or p-Erk in response to IL-2 or GM-CSF in myeloid and/or T cells. These kits can be used for example to determine inhibitor's profile for drug development and/or treatment selection. Without intending to be limited to any theory, pStat-5 is activated in both T-cells and monocytes upon stimulation with IL-2 and GM-C SF respectively, however different JAK family members are activated upstream of pStat-5. GM-CSF induced p-Stat-5 is mediated though JAK2, while IL-2 induced pStat-5 is mediated through JAK3. pERK could serve as a positive control for GM-C SF stimulation. This kit would allow for the measurement of JAK2 vs JAK3 specific inhibition and provide information on the potency and selectivity of the inhibitor tested. These kits can also be used in disease characterization. For instance, MPN cells from bone marrow and/or peripheral blood could be tested for their basal and induced levels of pSTAT-5 as a readout of constitutive or induced activity of JAK2.

b. Phosphatidylinositol 3-kinase (PI3K) Pathway:

PI3Ks are activated by a wide range of cell surface receptors (including receptor tyrosine kinases and G protein coupled receptors) to generate the lipid second messengers phosphatidylinositol 3,4,5-trisphosphate (PIP3) and phosphatidylinositol 3,4-biphosphate (PIP2). Examples of receptor tyrosine kinases include, but are not limited to IGF-1R, EGFR, HER2, JAK, c-Kit, VEGF-R, and PDGF-R. These lipid second messengers regulate a diverse array of cellular processes such as cell survival, growth, membrane trafficking glucose homeostasis, metabolism and cell motility. The binding of PIP2, PIP3, and other phosphatidylinositols to target proteins is mediated through the pleckstrin homology (PH) domain present in these target proteins. A key downstream effector of PI3K signaling that is often implicated in cancer is Akt, a serine/threonine kinase. Akt is activated when it is recruited to the membrane by an activated phosphatidylinositol. Once at the plasma membrane, Akt is phopshorylated at T308 by PDK1 and at S473 by PDK2s to become fully activated. Aid regulates a number of substrates through phosphorylation. Akt substrates include FOXO transcription factors, Bad, GSK-3β, I-κB, mTOR, and MDM-2, molecules known to mediate cell survival, cell proliferation, membrane trafficking, glucose homeostasis, metabolism and cell motility. Cancer-associated mutations in the PI3K pathway cause aberrant signaling, resulting in increased cell survival and growth. Classes of oncogenic mutations in the PI3K pathway include gain-of-function mutations in growth factor receptors, the PIK3CA locus (encoding the p110α subunit of PI3K), or Akt, loss-of-function mutations in the lipid phosphatase and tensin homolog deleted on chromosome ten (PTEN), or mutations that impair the tuberous sclerosis complex (TSC1/2). See Engelman, J. A. Targeting PI3K signalling in cancer: opportunities, challenges and limitations. Nature Reviews Cancer (2009) 9:550-62; Garcia-Echeverria, C. & Sellers, W. R. Oncogene (2008) 27:5511-26; Yuan, T. L. & Cantley, L. C. PI3K pathway alterations in cancer: variations on a theme. Oncogene (2008) 27: 5497-5510; and Shaw, R. Ras, PI(3)K and mTOR signaling controls tumor cell growth, Nature (2006) 441:424-30, which are hereby fully incorporated by reference.

c. Protein Kinase C (PKC) Signaling:

The PKC family of serine/threonine kinases mediates signaling pathways following activation of receptor tyrosine kinases, G-protein coupled receptors and cytoplasmic tyrosine kinases. Activation of PKC family members is associated with cell proliferation, differentiation, survival, immune function, invasion, migration and angiogenesis. Disruption of PKC signaling has been implicated in tumorigenesis and drug resistance. PKC isoforms have distinct and overlapping roles in cellular functions. PKC was originally identified as a phospholipid and calcium-dependent protein kinase. The mammalian PKC superfamily consists of 13 different isoforms that are divided into four subgroups on the basis of their structural differences and related cofactor requirements cPKC (classical PKC) isoforms ($\alpha, \beta I, \beta II$ and $\gamma$), which respond both to Ca2+ and DAG (diacylglycerol), nPKC (novel PKC) isoforms ($\delta, \epsilon, \theta$ and $\eta$), which are insensitive to Ca2+, but dependent on DAG, atypical PKCs (aPKCs, $\iota/\lambda, \zeta$), which are responsive to neither co-factor, but may be activated by other lipids and through protein-protein interactions, and the related PKN (protein kinase N) family (e.g. PKN1, PKN2 and PKN3), members of which are subject to regulation by small GTPases. Consistent with their different biological functions, PKC isoforms differ in their structure, tissue distribution, subcellular localization, mode of activation and substrate specificity.

Maximal activation of PKC kinase function requires two steps (Griner, E. M., and Kazanietz, M. G. Protein kinase C and other diacylglycerol effectors in cancer. Nat Rev Cancer (2007) 7: 281-94). First, phosphoinositide-dependent kinase 1 (PDK-1) performs a priming phosphorylation of PKC in the cytoplasm. Second, the membrane-bound phospholipid DAG, a product of phosphoinositide hydrolysis (for example, hydrolysis of PIP2 to form IP3), recruits primed PKC to the plasma membrane, where it mediates PKC activation and the release of an inhibitory substrate (a pseudo-substrate) to which the inactive enzyme was bound. Activated PKC then phosphorylates targets such as kinases and integrins. Phosphorylation of PKC targets regulates downstream signaling pathways, many of which have been implicated in cancer, including pathways that regulate cellular growth, motility, cell cycle progression, and apoptosis (Griner, E. M., Kazanietz, M. G. Nat Rev Cancer (2007) 7: 281-294). The downstream events following PKC activation are poorly understood, although the MEK-ERK (mitogen activated protein kinase kinase-extracellular signal-regulated kinase) pathway is thought to have an important role. There is also evidence to support the involvement of PKC in the PI3K-Akt pathway. PKC isoforms probably form part of the multi-protein complexes that facilitate cellular signal transduction. Many reports describe dysregulation of PKC family members in cancer cells. For example, alterations in PKCε have been detected in thyroid cancer, and have been correlated with aggressive, metastatic breast cancer and PKCι was shown to be associated with poor outcome in ovarian cancer. (Knauf J. A., et al. Isozyme-Specific Abnormalities of PKC in Thyroid Cancer: Evidence for Post-Transcriptional Changes in PKC Epsilon. *The Journal of Clinical Endocrinology & Metabolism.* 87(5): 2150-2159; Zhang L et al. Cancer Res. (2006) 66(9):4627-4635.

d. Mitogen Activated Protein (MAP) Kinase Pathways:

MAP kinase (MAPK) signaling cascades function in a multitude of cellular processes, including subcellular localization of proteins, gene regulation, growth, proliferation, differentiation, and cell cycle entry, and regulation of development (Lawrence et al., Cell Research (2008) 18: 436-442). Aberrant or inappropriate functioning of MAPKs has been observed in diseases ranging from cancer to inflammatory disease to obesity and diabetes. MAPKs are activated by protein kinase cascades consisting of three or more protein kinases in series: MAPK kinase kinases (MAP3Ks) activate MAPK kinases (MAP2Ks) by dual phosphorylation on S/T residues; MAP2Ks then activate MAPKs by dual phosphorylation on Y and T residues; MAPKs then phosphorylate target substrates on select S/T residues typically followed by P. In the ERK1/2 cascade the MAP3K is usually a member of the Raf family. Many diverse MAP3Ks reside upstream of the p38 and the c-Jun N-terminal kinase/stress-activated protein kinase (JNK/SAPK) MAPK groups, which have generally been associated with responses to cellular stress. Downstream of the activating stimuli, the kinase cascades may themselves be stimulated by combinations of small G proteins, MAP4Ks, scaffolds, or oligomerization of the MAP3K in a pathway. In the ERK1/2 pathway, Ras family members usually bind to Raf proteins leading to their activation as well as to the subsequent activation of other downstream members of the pathway.

e. Ras/RAF/MEK/ERK Pathway:

Classic activation of the RAS/Raf/MAPK cascade occurs following ligand binding to a receptor tyrosine kinase at the cell surface, but a vast array of other receptors have the ability to activate the cascade as well, such as integrins, serpentine receptors, heterotrimeric G-proteins, and cytokine receptors. Although conceptually linear, considerable cross talk occurs between the Ras/Raf/MAPK/Erk kinase (MEK)/Erk MAPK pathway and other MAPK pathways as well as many other signaling cascades. The pivotal role of the Ras/Raf/MEK/Erk MAPK pathway in multiple cellular functions underlies the importance of the cascade in oncogenesis and growth of transformed cells. As such, the MAPK pathway has been a focus of intense investigation for therapeutic targeting. Many receptor tyrosine kinases are capable of initiating MAPK signaling. They do so after activating phosphorylations within their cytoplasmic domains provide docking sites for src-homolgy 2 (SH2) domain-containing signaling molecules. Of these, adaptor proteins such as Grb2 recruit guanine nucleotide exchange factors such as SOS-1 or CDC25 to the cell membrane. The guanine nucleotide exchange factor is now capable of interacting with Ras proteins at the cell membrane to promote a conformational change and the exchange of GDP for GTP bound to Ras. Multiple Ras isoforms have been described, including K-Ras, N-Ras, and H-Ras. Termination of Ras activation occurs upon hydrolysis of RasGTP to RasGDP. Ras proteins have intrinsically low GTPase activity. Thus, the GTPase activity is stimulated by GTPase-activating proteins such as NF-1 GTPase-activating proteinlneurofibromin and p120 GTPase activating protein thereby preventing prolonged Ras stimulated signaling. Ras activation is the first step in activation of the MAPK cascade. Following Ras activation, Raf (A-Raf, B-Raf, or Raf-1) is recruited to the cell membrane through binding to Ras and activated in a complex process involving phosphorylation and multiple cofactors that is not completely understood. Raf proteins directly activate MEK1 and MEK2 via phosphorylation of multiple serine residues. MEK1 and MEK2 are themselves tyrosine and threonine/serine dual-specificity kinases that subsequently phosphorylate threonine and tyrosine residues in Erk1 and Erk2 resulting in activation. Although MEK1/2 has no known targets besides Erk proteins, Erk has multiple targets including Elk-1, c-Ets1, c-Ets2, p90RSK1, MNK1, MNK2, and TOB. The cellular functions of Erk are diverse and include regulation of cell proliferation, survival, mitosis, and migration. McCubrey, J., Roles of the Raf/MEK/ERK pathway in cell growth, malignant transformation and drug resistance, Biochimica et Biophysica Acta. (2007)1773: 1263-1284, hereby fully incorporated by reference in its entirety for all purposes, Friday and Adjei Clinical Cancer Research (2008) 14:342-346.

f. p38 MAPK Pathway:

p38 MAPKs respond to a wide range of extracellular cues, particularly cellular stressors such as UV radiation, osmotic shock, hypoxia, pro-inflammatory cytokines and less often growth factors (Raman et al. Differential regulation and properties of MAPKs. Oncogene (2007) 26: 3100-12) There are four p38 family members ($\alpha$, $\beta$, $\gamma$ and $\delta$). While p38 MAPKs share about 40% sequence identity with other MAPKs, they share only about 60% identity among themselves, suggesting highly diverse functions. Responding to osmotic shock is likely to be among the ancestral functions of this pathway, because yeast p38 activates both short and long-term homeostatic mechanisms to osmotic stress. p38 is activated via dual phosphorylation on the TGY motif within its activation loop by its upstream protein kinases MEK3 and -6 (MEK3/6). MEK3/6 are activated by numerous MAP3Ks including MEKK1-4, TAOs, TAK and ASK. p38 MAPK is a highly promising MAPK therapeutic target for rheumatoid arthritis as p38 MAPK isoforms have been implicated in the regulation of many of the processes central to disease pathogenesis, such as migration and accumulation of leucocytes, production of cytokines and pro-inflammatory mediators, and angiogenesis. Further, the p38 MAPK pathway plays a role in cancer, heart and neurodegenerative diseases and may serve as promising therapeutic target for these diseases. Cuenda, A. p38 MAP-Kinases pathway regulation, function, and role in human diseases. Biochimica et Biophysica Acta. (2007) 1773: 1358-1375; Thalhamer et al., Rheumatology (2008) 47:409-414; Roux, P. ERK and p38 MAPK-Activated Protein Kinases: a Family of Protein Kinases with Diverse Biological Functions, Microbiology and Molecular Biology Reviews, June 2004, 320-344; hereby fully incorporated by reference in its entirety for all purposes.

In some embodiments, the kits of the invention are directed to measure the p38 MAPK pathway. The kits of the invention allow for the measurement of relevant members of the pathway such that relevant information is obtained, e.g. for the diagnosis, prognosis, patient stratification and/or selection of treatment for a condition. For instance, rheumatoid arthritis (RA) is an inflammatory autoimmune disease affecting 1% of the western world population. The initial events causes the proliferation of synovial fibroblast and further release of inflammatory molecules that eventually will cause joint destruction. The chronic inflammation of the joints is mainly a result of activated T-cell, macrophages and B-cells where cytokine induction of enzymes like matrix metalloproteinases play a destructive role. Several MAPK p38 inhibitors have been shown to block the production of interleukin-1 (IL-1), tumor-necrosis factor-$\alpha$ (TNF-$\alpha$) and other pro-inflammatory cytokines. MAPK p38 plays an important role in the signaling pathway that regulates inflammation. Inhibiting the activity of p38 by pyridinyl imidazole (SB 203580) blocks pro-inflammatory cytokine production in animal models for arthritis.

In some embodiments, the invention provides kits for the measurements of p-p38, p-MK2, and p-ERK in response to TNF and/or LPS in myeloid cells. In some embodiments these kits are used to measure an inhibitor profile, e.g., for drug development or selection of treatment. Without intending to be limited to any theory, p-ERK, p-p38 and its downstream substrate p-MK2 are activated when cells are stimulated with TNFa. This kit would allow for the measurement of these kinases after treatment of the cells with small molecule kinase inhibitors. This kit would be able to measure if the compound inhibits the phosphorylation of p38 (p-p38 signal goes down) in CD14+ monocytes. The kit could also measure if a compound inhibits the activity of p-p38 (p-MK2 signal goes down) while p38 phosphorylation is maintained. This kit would provide information on the potency and selectivity of the inhibitors tested.

DNA Damage Response and Apoptosis

In some embodiments, the invention provides a kit to measure DNA damage and/or apoptosis in one or more cell populations. The response to DNA damage is a protective measure taken by cells to prevent or delay genetic instability and tumorigenesis. It allows cells to undergo cell cycle arrest and gives them an opportunity to either: repair the broken DNA and resume passage through the cell cycle or, if the breakage is irreparable, trigger senescence or an apoptotic program leading to cell death (Wade Harper et al., Molecular Cell, (2007) 28 p739-745, Bartek J et al., Oncogene (2007)26 p7773-9).

Several protein complexes are positioned at strategic points within the DNA damage response pathway and act as sensors, transducers or effectors of DNA damage. Depending on the nature of DNA damage for example; double stranded breaks, single strand breaks, single base alterations due to alkylation, oxidation etc, there is an assembly of specific DNA damage sensor protein complexes in which activated ataxia telangiectasia mutated (ATM) and ATM- and Rad3 related (ATR) kinases phosphorylate and subsequently activate the checkpoint kinases Chk1 and Chk2. Both of these DNA-signal transducer kinases amplify the damage response by phosphorylating a multitude of substrates. Both checkpoint kinases have overlapping and distinct roles in orchestrating the cell's response to DNA damage.

Maximal kinase activation of Chk2 involves phosphorylation and homo-dimerization with ATM-mediated phosphorylation of T68 on Chk2 as a preliminary event. This in turn activates the DNA repair. As mentioned above, in order for DNA repair to proceed, there must be a delay in the cell cycle. Chk2 seems to have a role at the G1/S and G2/M junctures and may have overlapping functions with Chk1. There are multiple ways in which Chk1 and Chk2 mediate cell cycle suspension. In one mechanism Chk2 phosphorylates the CDC25A and CDC25C phosphatases resulting in their removal from the nucleus either by proteosomal degradation or by sequestration in the cytoplasm by 14-3-3. These phosphatases are no longer able to act on their nuclear CDK substrates. If DNA repair is successful cell cycle progression is resumed (Antoni et al., Nature reviews cancer (2007)7, p925-936).

When DNA repair is no longer possible the cell undergoes apoptosis with participation from Chk2 in p53 independent and dependent pathways. Chk2 substrates that operate in a p53-independent manner include the E2F1 transcription factor, the tumor suppressor promyelocytic leukemia (PML) and the polo-like kinases 1 and 3 (PLK1 and PLK3). E2F1 drives the expression of a number of apoptotic genes including Caspases 3, 7, 8 and 9 as well as the pro-apoptotic Bcl-2 related proteins (Bim, Noxa, PUMA).

In its response to DNA damage, the p53 activates the transcription of a program of genes that regulate DNA repair, cell cycle arrest, senescence and apoptosis. The overall functions of p53 are to preserve fidelity in DNA replication such that when cell division occurs tumorigenic potential can be avoided. In such a role, p53 is described as "The Guardian of the Genome (Riley et al., Nature Reviews Molecular Cell Biology (2008) 9 p402-412). The diverse alarm signals that impinge on p53 result in a rapid increase in its levels through a variety of post translational modifications. Worthy of mention is the phosphorylation of amino acid residues within the amino terminal portion of p53 such that p53 is no longer under the regulation of Mdm2. The responsible kinases are ATM, Chk1 and Chk2. The subsequent stabilization of p53 permits it to transcriptionally regulate multiple pro-apoptotic members of the Bcl-2 family, including Bax, Bid, Puma, and Noxa (Discussion below).

The series of events that are mediated by p53 to promote apoptosis including DNA damage, anoxia and imbalances in growth-promoting signals are sometimes termed the 'intrinsic apoptotic" program since the signals triggering it originate within the cell. An alternate route of activating the apoptotic pathway can occur from the outside of the cell mediated by the binding of ligands to transmembrane death receptors. This extrinsic or receptor mediated apoptotic program acting through their receptor death domains eventually converges on the intrinsic, mitochondrial apoptotic pathway as discussed below (Sprick et al., Biochim Biophys Acta. (2004) 1644: 125-32).

Key regulators of apoptosis are proteins of the Bcl-2 family. The founding member, the Bcl-2 proto-oncogene was first identified at the chromosomal breakpoint of (14:18) bearing human follicular B cell lymphoma. Unexpectedly, expression of Bcl-2 was proved to block rather than promote cell death following multiple pathological and physiological stimuli (Danial and Korsemeyer, Cell (2204) 116, p205-219). The Bcl-2 family has at least 20 members which are key regulators of apoptosis, functioning to control mitochondrial permeability as well as the release of proteins important in the apoptotic program. The ratio of anti- to pro-apoptotic molecules such as Bcl-2/Bax constitutes a rheostat that sets the threshold of susceptibility to apoptosis for the intrinsic pathway, which utilizes organelles such as the mitochondrion to amplify death signals. The family can be divided into 3 subclasses based on structure and impact on apoptosis. Family members of subclass 1 including Bcl-2, Bel-$X_L$ and Mcl-1 are characterized by the presence of 4 Bcl-2 homology domains (BH1, BH2, BH3 and BH4) and are anti-apoptotic. The structure of the second subclass members is marked for containing 3 BH domains and family members such as Bax and Bak possess pro-apoptotic activities. The third subclass, termed the BH3-only proteins include Noxa, Puma, Bid, Bad and Bim. They function to promote apoptosis either by activating the pro-apoptotic members of group 2 or by inhibiting the anti-apoptotic members of subclass 1 (Er et al., Biochimica et Biophysica Act (2006) 1757, p1301-1311, Fernandez-Luna Cellular Signaling (2008) Advance Publication Online).

The role of mitochondria in the apoptotic process was clarified as involving an apoptotic stimulus resulting in depolarization of the outer mitochondrial membrane leading to a leak of cytochrome C into the cytoplasm. Association of Cytoplasmic cytochrome C molecules with adaptor apoptotic protease activating factor (APAF) forms a structure called the apoptosome which can activate enzymatically latent pro-caspase 9 into a cleaved activated form. Caspase 9 is one member of a family of cysteine aspartyl-specific proteases; genes encoding 11 of these proteases have been mapped in the human genome. Activated caspase 9, classified as an intiator caspase, then cleaves procaspase 3 which cleaves more downstream procaspases, classified as executioner caspases, resulting in an amplification cascade that promotes cleavage of death substrates including poly(ADP-ribose) polymerase 1 (PARP). The cleavage of PARP produces 2 fragments both of which have a role in apoptosis (Soldani and Scovassi Apoptosis (2002) 7, p321). A further level of apoptotic regulation is provided by smac/Diablo, a mitochondrial protein that inactivates a group of anti-apoptotic proteins termed inhibitors of apoptosis (XIAPs) (Huang et al., Cancer Cell (2004) 5:1-2). XIAPs operate to block caspase activity in 2 ways; they bind directly to and inhibit caspase activity and in certain cases they can mark caspases for ubiquitination and degradation.

Members of the caspase gene family (cysteine proteases with aspartate specificity) play significant roles in both inflammation and apoptosis. Caspases exhibit catalytic and substrate recognition motifs that have been highly conserved. These characteristic amino acid sequences allow caspases to interact with both positive and negative regulators of their activity. The substrate preferences or specificities of individual caspases have been exploited for the development of peptides that successfully compete for caspase binding. In addition to their distinctive aspartate cleavage sites at the P1 position, the catalytic domains of the caspases require at least four amino acids to the left of the cleavage site with P4 as the prominent specificity-determining residue. WEHD, VDVAD, and DEVD are examples of peptides that preferentially bind caspase-1, caspase-2 and caspase-3, respectively. It is possible to generate reversible or irreversible inhibitors of caspase activation by coupling caspase-specific peptides to certain aldehyde, nitrile or ketone compounds. These caspase inhibitors can successfully inhibit the induction of apoptosis in various tumor cell lines as well as normal cells. Fluoromethyl ketone (FMK)-derivatized peptides act as effective irreversible inhibitors with no added cytotoxic effects. Inhibitors synthesized with a benzyloxycarbonyl group (also known as BOC or Z) at the N-terminus and O-methyl side chains exhibit enhanced cellular permeability thus facilitating their use in both in vitro cell culture as well as in vivo animal studies. Benzyloxycarbonyl-Val-Ala-Asp (OMe) fluoromethylketone (ZVAD) is a caspase inhibitor. See Misaghi, et al., z-VAD-fmk inhibits peptide:N-glycanase and may result in ER stress Cell Death and Differentiation (2006) 13:163-165.

The balance of pro- and anti-apoptotic proteins is tightly regulated under normal physiological conditions. Tipping of this balance either way results in disease. An oncogenic outcome results from the inability of tumor cells to undergo apoptosis and this can be caused by over-expression of anti-apoptotic proteins or reduced expression or activity of pro-apoptotic protein.

In some embodiments, apoptosis kits of the present invention may comprise one or more binding elements and one or more modulators that slow or stop the growth of cells and/or induce apoptosis of cells to measure one or more activatable elements in cells in response to the modulators. In some embodiments, the activatable element is selected from the group consisting of PARP+, cleaved Caspase 8, cleaved Caspase 3, H2AX, and the modulator that slows or stops the growth of cells and/or induces apoptosis of cells is selected from the group consisting of Etoposide, Gemtuzumab (such as Gemtuzumab ozogamicin, marketed as Mylotarg), Daunorubicin, and Ara-C.

In some embodiments, DNA damage kits of the present invention may comprise one or more binding elements to determine the status of an activatable element within a DNA damage pathway in response to a modulator that slows or stops the growth of cells and/or induces apoptosis of cells is determined. In some embodiments, the kit further comprises a modulator that slows or stops the growth of cells and/or induces apoptosis. In some embodiments, the activatable element within a DNA damage pathway is selected from the group consisting of Chk1, Chk2, ATM, and ATR and the modulator that slows or stops the growth of cells and/or induces apoptosis of cells is selected from the group consisting of Staurosporine, Etoposide, Gemtuzumab (such as Gemtuzumab ozogamicin, marketed as Mylotarg), Daunorubicin, and Ara-C.

In some embodiments, the kits of the invention provides for interrogation of the apoptotic machinery. In some embodiments, the kits of the invention provides for interrogation of the apoptotic machinery with Etoposide with or without ZVAD, an inhibitor of caspases. Etoposide phosphate (brand names: Eposin, Etopophos, Vepesid, VP-16) is an inhibitor of the enzyme topoisomerase II and a semisynthetic derivative of podophyllotoxin, a substance extracted from the mandrake root Podophyllum peltatum. Possessing potent antineoplastic properties, etoposide binds to and inhibits topoisomerase II and its function in ligating cleaved DNA molecules, resulting in the accumulation of single- or double-strand DNA breaks, the inhibition of DNA replication and transcription, and apoptotic cell death. Etoposide acts primarily in the G2 and S phases of the cell cycle. See the NCI Drug Dictionary at http://www.cancer.gov/Templates/drugdictionary.aspx?CdrID=39207.

Apoptosis is a tightly regulated and at the same time highly efficient cell death program which requires the interplay of a multitude of factors. The components of the apoptotic signalling network are genetically encoded and are generally expressed and assembled in nucleated cells ready to be activated by a death-inducing stimulus. Apoptosis can be triggered by various stimuli from outside or inside the cell, e.g. by ligand binding to cell surface receptors, by DNA damage due to defects in DNA repair mechanisms, treatment with cytotoxic drugs or irradiation, by a lack of survival signals, aberrant cell cycle signaling or arrest, or by developmental death signals. Death signals of diverse origins nevertheless appear to eventually activate common cell death machinery leading to the characteristic features of apoptotic cell death.

The apoptosis pathway involves a series of positive and negative regulators of proteases called caspases, which cleave substrates, such as poly-ADP-ribose-polymerase (PARP), actin, fodrin, and lamin. Apoptosis is accompanied by the endonuclease-mediated intranucleosomal degradation of chromosomal DNA. A number of death receptors have been identified. Death receptors are cell surface receptors that transmit apoptotic signals initiated by death ligands. The death receptors sense signals that tell the cell that it is in an uncompromising environment and needs to die (extrinsic pathway). These receptors can activate the death caspases within seconds of ligand binding and induce apoptosis within hours. Death receptors belong to the tumor necrosis factor receptor gene superfamily and have typical cystine-rich extracellular domains and an additional cytoplasmic sequence termed the death domain. The best characterized death receptors are CD95 (also called Fas or Apo1) and TNF receptor TNFR1 (also called p55 or CD120a).

Signaling by cytokines may also affect apoptosis. Progenitors with impaired signal transduction, thus constituting a refractory target cell, could undergo accelerated apoptosis analogous to withdrawal of obligate survival factors. Alternatively, the apoptotic pathway itself may be dysregulated with direct activation of the Fas pathway. As MDS evolves to AML the acceleration of apoptosis declines and AML is characterized by increasing progenitor survival. For more detailed information on apoptosis mechanism and pathways, see Kufe, D. W. et al., Cancer Medicine, 6$^{th}$ Ed. (BC Decker, 2003).

a. BCR/ABL Function; CML Monitoring

Chronic myeloid leukemia (CML) is a hematopoietic disorder characterized by the presence of a reciprocal translocation involving the long arms of chromosome 9 and 22. The resultant BCR/ABL fusion gene encodes a constitutively activated tyrosine kinase, which phosphorylates a broad range of substrates, resulting in increased cell growth and impaired apoptosis. See Sattler M. et al., Semin Hematol. (2003) 40:4-10. Imatinib mesylate (Gleevec) is a targeted tyrosine kinase inhibitor for use in CML therapy. Imatinib mesylate binds to the ATP-binding site in the kinase domain of the BCR/ABL tyrosine kinase, thus preventing ATP binding and activation of the kinase. See Wadleigh M. et al., Blood (2005) 105:22-30.

CT10 regulator of kinase like adaptor protein (CrkL) is a known BCR-ABL kinase downstream target and has been widely used as a surrogate marker for physiological BCR-ABL tyrosine kinase activity. See Hamilton A, Elrick L, Myssina S, et al. Leukemia (2006) 20:1035-1039. Phosphorylation of the CrkL is used as a measure of BCR-ABL activity to assess drug uptake and physiological drug function. As a result, BCR-ABL inhibition can be monitored by performing peripheral blood flow cytometry for phosphorylation of CrkL. (Singer C F, et al. Oncol Rep 2006; 15:353-359.)

In some embodiments, the invention may comprise a kit to measure the effects of drug treatment and BCR/ABL function in CML patients. For example, the kit may include one or more therapeutic agent such as Imatinib and salts thereof (marketed as Gleevec) or Dasatinib, and binding element for the detection of p-CrkL.

Protein Phosphatase Function:

Protein phosphatases mediate the dephosphorylation of a wide range of targets. Mutations in protein phosphatases have been implicated in disease, including cancer. For example, in healthy cells the tumor suppressor PTEN is a phosphatase that negatively regulates PI3K signaling by desphosproylating phosphatidylinositides, which function as second messengers in this pathway (See Salmena, L. et al. Tenets of PTEN tumor suppression. Cell 133: 403-14, 2008). However, an estimated 30-80% of cancers contain mutations that reduce or eliminate PTEN function. A loss of PTEN function results in an accumulation of phosphatidylinositides, which promote the phosphorylation of downstream substrates that promote cell growth and survival, for example AKT and SGK3 (See Vasudevan, K. M., et al. AKT-independent signaling downstream of oncogenic PIK3CA mutations in human cancer. Cancer Cell 16: 21-32, 2009; Yuan and Cantley, PI3K pathway alterations in cancer: variations on a theme. Oncogene 27: 5497-5510, 2008). Because of the importance of PTEN and the PI3K pathway in cancer, there are a number of therapeutics in development that target this pathway (See Faivre, S., et al. Current development of mTOR inhibitors as anticancer agents. Nature Reviews Drug Discovery 5, 671-688, 2006). Monitoring the activity of PTEN and other phosphatases can be important in identifying the mechanisms of oncogenesis in cancer cells, selecting therapeutics that target these mechanisms, and measuring the efficacy of proposed therapeutics.

One of the earliest events that occur after engagement of myeloid receptors is the phosphorylation of cellular proteins on serine, threonine, and tyrosine residues 8, 9, 10. The overall level of phosphorylated tyrosine residues is regulated by the competing activities of protein tyrosine kinases (PTKs) and protein tyrosine phosphatases (PTPs). Decreases in the activity of tyrosine phosphatases may also contribute to an increase in cellular tyrosine phosphorylation following stimulation.

SHP-1 (PTPN6) is a non-receptor protein tyrosine phosphatase that is expressed primarily in hematopoietic cells. The enzyme is composed of two SH2 domains, a tyrosine phosphatase catalytic domain and a carboxy-terminal regulatory domain (Yi, T. L. et al. (1992) Mol Cell Biol 12, 836-46). SHP-1 removes phosphates from target proteins to down regulate several tyrosine kinase regulated pathways. In hematopoietic cells, the N-terminal SH2 domain of SHP-1 binds to tyrosine phosphorylated erythropoietin receptors (EpoR) to negatively regulate hematopoietic growth (Yi, T. et al. (1995) Blood 85, 87-95). Following ligand binding in myeloid cells, SHP-1 associates with IL-3R β chain and down regulates IL-3-induced tyrosine phosphorylation and cell proliferation (Yi, T. et al. (1993) Mol Cell Biol 13, 7577-86). Because SHP-1 downregulates signalling pathways emanating from receptor tyrosine kinases, cytokine receptors, multi-chain recognition receptors and integrins, it is considered a potential tumor suppressor (Wu, C. et al. (2003) Gene 306, 1-12, Bhattacharya, R. et al. (2008) J Mol Signal 3, 8).

SHP-2 (PTPN11) is a ubiquitously expressed, non-receptor protein tyrosine phosphatase (PTP). It participates in signaling events downstream of receptors for growth factors, cytokines, hormones, antigens and extracellular matrices in the control of cell growth, differentiation, migration and death (Qu, C. K. (2000) Cell Res 10, 279-88). Activation of SHP-2 and its association with Gab1 is critical for sustained Erk activation downstream of several growth factor receptors and cytokines (Maroun, C. R. et al. (2000) Mol Cell Biol 20, 8513-25.).

In some embodiments, the invention provides methods for measuring the activity of phosphatases. Accumulation of phosphate groups on direct and indirect phosphatase targets, for example Akt, PLCδ2, and SLP76, decreases in proportion to phosphatase activity. Thus, levels of phosphorylated substrates, for example, p-Akt, p-PLCδ2, and p-SLP76 can serve as measurements of phosphatase activity. In one embodiment, a population of cells is contacted with the modulator $H_2O_2$, which functions as a pan-phosphatase inhibitor, while another population from the same sample is untreated. Each population is contacted with a binding element, for example, fluorophore-conjugated antibodies, and levels of phosphorylated substrates are measured in single cells, for example by flow cytometry. Increased levels of phosphorylated substrates in the treated group would indicate phosphatase activity. In another embodiment, two different populations of cells are each treated with $H_2O_2$, levels of phosphorylated substrates are measured in single cells using the methods above, and relative phosphatase activity in each population in compared based on levels of phosphorylated substrates.

In some embodiments, the invention provides methods for measuring the activity of phosphatases. Accumulation of phosphate groups on direct and indirect phosphatase targets, for example Akt, PLCδ2, and SLP76, decreases in proportion to phosphatase activity. Thus, levels of phosphorylated substrates, for example, p-Akt, p-PLCδ2, and p-SLP76 can serve as measurements of phosphatase activity. In one embodiment, the invention includes a kit to contact a population of cells with the modulator $H_2O_2$, which functions as a pan-phosphatase inhibitor, while another population from the same sample is untreated. The kit also includes one or more binding elements, for example, fluorophore-conjugated antibodies, to contact each population and measure the levels of phosphorylated substrates, for example by flow cytometry. Increased levels of phosphorylated substrates in the treated group would indicate phosphatase activity. In another embodiment, a kit of the invention can be used to treat two different populations of cells with $H_2O_2$, to measure the levels of phosphorylated substrates and/or relative phosphatase activity in each population using the methods above, and to make comparisons based on levels of phosphorylated substrates.

Calcium Signaling:

Ca$^{2+}$ can have multiple roles in cell survival and growth. Ligand-receptor binding can result in the activation of second messenger membrane-bound phosphoinositides such as P1(4,5)P2, the hydrolysis of which produces the soluble molecule inositol triphosphate (1P3). 1P3 triggers Ca$^{2+}$ release from intracellular vesicles into the cytoplasm. The subsequent spike in Ca$^{2+}$ levels can indirectly regulate enzyme activity via calcium binding proteins e.g. calcium/calmodulin-dependent kinases II and IV in neurons, calcineurin in lymphocytes (Berridge, M. J. et al. Nat. Rev. Mol. Cell. Biol. (2000) 1:11-21). Ca$^{2+}$ can also directly regulate gene expression, for example, c-fos (Carrion, A. M. et al. (1999) Nature 398:80-84). Thapsigargin is an inhibitor of the Ca$^{2+}$-ATPase responsible for sequestering calcium in intracellular vesicles. See Lenormand, P. et al. Cell Growth Differ (1990) 1:627-635. Thapsigargin treatment leads to both increased calcium release and calcium influx across the plasma membrane. Rodland K. D. et al., Molecular Endocrinology (1997) 11:281-91. In some embodiments, the invention may comprise a kit to measure calcium levels in one or more population of cells. In some embodiments, the invention may comprise a kit to measure the effects of drug treatment in calcium levels patients.

Chemokine Function:

Chemokines are a family of small cytokines that mediate a variety of responses in healthy cells, including cell mobilization and chemotaxis (Baggelioni, M, et al. Human Chemokines: An update. Ann. Rev. Immun. (1997) 15: 675-705). Tumor cells also secrete and respond to chemokines, which often synergize with other cytokines to promote cell growth and survival (Raman, D., et al. Role of chemokines in tumor growth. Cancer letters (2007) 256: 137-65).

There are four major families of chemokines, based on the positioning of two conserved N terminal cystine residues: CXC, CC, CX3C, and C. The CXC family is subdivided into ELR+ and ELR− subfamilies, depending on whether a Glu-Leu-Arg motif precedes the CXC sequence (Raman, D., et al. Cancer letters (2007) 256: 137-165). Chemokine receptors are seven-transmembrane G protein coupled receptors. Chemokine binding to these receptors results in activation of heterotrimeric G proteins, which activate downstream targets. For example, in leukocyte migration, chemokine-receptor binding results in the activation of PI3K, leading to the production of PIP3, and the subsequent activation of Rho and Rac family GTPases, which mediate cytoskeletal rearrangements and subsequent cell mobility (Rot, A. and von Andrian, U. H. Chemokines in Innate and Adaptive Host Defense: Basic Chemokines Grammar for Immune Cells. Ann. Rev. Immun. (2004) 22:891-928). Through the activation of multiple signaling pathways, chemokines induce a wide range of cellular responses, including leukocyte movement, activation and accumulation of inflammatory cells, and cell growth and survival.

The chemokine Stromal cell-Derived Factor (SDF)-1/CXCL12 is expressed constitutively in a number of tissues including liver, lung, lymph nodes, adrenal glands, and bone marrow (Raman, D., et al. Cancer letters (2007) 256:137-65). In healthy cells, including those of the hematopoietic lineage, SDF-1 mediates cell mobilization and chemotaxis through the chemokine 4 receptor (CXCR4) (Broxmeyer, H. E. Curr. Opin. Hemat. (2008) 15:49-58). SDF-1 also signals through the chemokine 7 receptor (CXCR7) to promote cell growth and survival (Burns, J. M. et al. A novel chemokine receptor for SDF-1 and 1-TAC involved in cell survival, cell adhesion, and tumor development. J. Exp. Med. (2006) 203:2201-13). CXCR7 is highly expressed in some tumor cell lines, and treating animal tumor models with a CXCR7 inhibitor impairs tumor growth (Burns, J. M. et al. J. Exp. Med. (2006) 203:2201-13). By signaling through both CXCR7 and CXCR4 on tumor cells, SDF-1 can potentially simultaneously enhance both tumor cell growth and migration (Raman, D., et al. Cancer letters (2007) 256:137-165).

In some embodiments, the invention can comprise a kit for monitoring the effects of chemokine signaling. For example, the kit can include SDF-1α to induce signaling on an SDF-1 axis, and binding elements to detect activated target downstream of SDF-1, for example p-Akt, p-Erk, and pS6. The kit can be used, for example, to identify profiles of SDF-1 cancer cells, or to measure the effects of an inhibitor compound on SDF-1 signaling.

Cell Cycle

The cell cycle, or cell-division cycle, is the series of events that take place in a cell leading to its division and duplication (replication). The cell cycle consists of five distinct phases: G0 phase, G1 phase, S phase (synthesis), G2 phase (collectively known as interphase) and M phase (mitosis). M phase is itself composed of two tightly coupled processes: mitosis, in which the cell's chromosomes are divided between the two daughter cells, and cytokinesis, in which the cell's cytoplasm divides forming distinct cells. Activation of each phase is dependent on the proper progression and completion of the previous one. Cells that have temporarily or reversibly stopped dividing are said to have entered a state of quiescence called G0 phase.

Regulation of the cell cycle involves processes crucial to the survival of a cell, including the detection and repair of genetic damage as well as the prevention of uncontrolled cell division. The molecular events that control the cell cycle are ordered and directional; that is, each process occurs in a sequential fashion and it is impossible to "reverse" the cycle.

Two key classes of regulatory molecules, cyclins and cyclin-dependent kinases (CDKs), determine a cell's progress through the cell cycle. Many of the genes encoding cyclins and CDKs are conserved among all eukaryotes, but in general more complex organisms have more elaborate cell cycle control systems that incorporate more individual components. Many of the relevant genes were first identified by studying yeast, especially *Saccharomyces cerevisiae* genetic nomenclature in yeast dubs many these genes cdc (for "cell division cycle") followed by an identifying number, e.g., cdc25.

Cyclins form the regulatory subunits and CDKs the catalytic subunits of an activated heterodimer; cyclins have no catalytic activity and CDKs are inactive in the absence of a partner cyclin. When activated by a bound cyclin, CDKs perform a common biochemical reaction called phosphorylation that activates or inactivates target proteins to orchestrate coordinated entry into the next phase of the cell cycle. Different cyclin-CDK combinations determine the downstream proteins targeted. CDKs are constitutively expressed in cells whereas cyclins are synthesized at specific stages of the cell cycle, in response to various molecular signals.

Upon receiving a pro-mitotic extracellular signal, G1 cyclin-CDK complexes become active to prepare the cell for S phase, promoting the expression of transcription factors that in turn promote the expression of S cyclins and of enzymes required for DNA replication. The G1 cyclin-CDK complexes also promote the degradation of molecules that function as S phase inhibitors by targeting them for ubiquitination. Once a protein has been ubiquitinated, it is targeted for proteolytic degradation by the proteasome. Active S cyclin-CDK complexes phosphorylate proteins that make up the pre-replication complexes assembled during G1 phase on DNA replication origins. The phosphorylation serves two purposes: to activate each already-assembled pre-replication complex, and to prevent new complexes from forming. This ensures that every portion of the cell's genome will be replicated once and only once. The reason for prevention of gaps in replication is fairly clear, because daughter cells that are missing all or part of crucial genes will die. However, for reasons related to gene copy number effects, possession of extra copies of certain genes would also prove deleterious to the daughter cells.

Mitotic cyclin-CDK complexes, which are synthesized but inactivated during S and G2 phases, promote the initiation of mitosis by stimulating downstream proteins involved in chromosome condensation and mitotic spindle assembly. A critical complex activated during this process is an ubiquitin ligase known as the anaphase-promoting complex (APC), which promotes degradation of structural proteins associated with the chromosomal kinetochore. APC also targets the mitotic cyclins for degradation, ensuring that telophase and cytokinesis can proceed. Interphase: Interphase generally lasts at least 12 to 24 hours in mammalian tissue. During this period, the cell is constantly synthesizing RNA, producing protein and growing in size. By studying molecular events in cells, scientists have determined that interphase can be divided into 4 steps: Gap 0 (G0), Gap 1 (G1), S (synthesis) phase, Gap 2 (G2).

Cyclin D is the first cyclin produced in the cell cycle, in response to extracellular signals (e.g. growth factors). Cyclin D binds to existing CDK4, forming the active cyclin D-CDK4 complex. Cyclin D-CDK4 complex in turn phosphorylates the retinoblastoma susceptibility protein (Rb). The hyperphosphorylated Rb dissociates from the E2F/DP1/Rb complex (which was bound to the E2F responsive genes, effectively "blocking" them from transcription), activating E2F. Activation of E2F results in transcription of various genes like cyclin E, cyclin A, DNA polymerase, thymidine kinase, etc. Cyclin E thus produced binds to CDK2, forming the cyclin E-CDK2 complex, which pushes the cell from G1 to S phase (G1/S transition). Cyclin B along with cdc2 (cdc2-fission yeasts (CDK1-mammalia)) forms the cyclin B-cdc2 complex, which initiates the G2/M transition. Cyclin B-cdc2 complex activation causes breakdown of nuclear envelope and initiation of prophase, and subsequently, its deactivation causes the cell to exit mitosis.

Two families of genes, the Cip/Kip family and the INK4a/ARF (Inhibitor of Kinase 4/Alternative Reading Frame) prevent the progression of the cell cycle. Because these genes are instrumental in prevention of tumor formation, they are known as tumor suppressors.

The Cip/Kip family includes the genes p21, p27 and p57. They halt cell cycle in G1 phase, by binding to, and inactivating, cyclin-CDK complexes. p21 is a p53 response gene (which, in turn, is triggered by DNA damage, e.g. due to radiation). p27 is activated by Transforming Growth Factor β (TGF β), a growth inhibitor.

The INK4a/ARF family includes p16INK4a, which binds to CDK4 and arrests the cell cycle in G1 phase, and p14arf which prevents p53 degradation.

Cell cycle checkpoints are used by the cell to monitor and regulate the progress of the cell cycle. Checkpoints prevent cell cycle progression at specific points, allowing verification of necessary phase processes and repair of DNA damage. The cell cannot proceed to the next phase until checkpoint requirements have been met.

Several checkpoints are designed to ensure that damaged or incomplete DNA is not passed on to daughter cells. Two main checkpoints exist: the G1/S checkpoint and the G2/M checkpoint. G1/S transition is a rate-limiting step in the cell cycle and is also known as restriction point. An alternative model of the cell cycle response to DNA damage has also been proposed, known as the postreplication checkpoint. p53 plays an important role in triggering the control mechanisms at both G1/S and G2/M checkpoints.

DAPI (4',6-Diamidino-2-phenylindole) is a blue fluorescent probe that fluoresces brightly when it is selectively bound to the minor groove of double stranded DNA where its fluorescence is approximately 20-fold greater than in the non-bound state. DAPI has an excitation maximum at 345 nm and an emission maximum at 455 nm. Cells stained with DAPI emit fluorescence in direct proportion to their DNA content. An exponentially growing population of cells will have a DNA content distribution containing an initial peak of G0/G1 cells, a valley of S Phase cells, and a second peak containing G2/M cells. Cells in the G2/M Phase have twice the DNA content as cells in the G0/G1 Phase. DAPI offers a rapid method for measuring the DNA content of cells and provides a convenient research tool to monitor cell cycle status and regulation.

In some embodiments, a kit of the present invention comprises one or more binding elements to measure one or more activatable elements within a cell cycle pathway in response to a modulator that slows or stops the growth of cells and/or induces apoptosis of cells. In some embodiments, a kit can further comprise the modulator that slows or stops the growth of cells and/or induces apoptosis of cells. In some embodiments, the activatable element is selected from the group consisting of, Cdk1, Cyclin B1, Histone H3, Cyclin D1, p15, p16, and p21. In some embodiments, the modulator that slows or arrests cell cycle progression, and/or induces apoptosis of cells is selected from the group consisting of Staurosporine, Etoposide, Gemtuzumab (such as Gemtuzumab ozogamicin, marketed as Mylotarg), Daunorubicin, Ara-C, Azacitidine (marketed as Vidaza), Decitabine (marketed as Dacogen), and Vorinostat (marketed as Zolinza).

Kits

In some embodiments, the present invention provides a kit comprising binding elements specifically targeted toward certain diseases, cell types and signaling pathways. A kit can comprise one or more binding elements for one or more intracellular marker to measure the effects of modulators or therapeutic agents on evoked cell signaling. A kit can further comprise the modulators and/or the therapeutic agents. A kit of the invention can allow for the analysis of intracellular markers in response to modulators or therapeutic agents in specific diseases, cell types and signaling pathways. This provides relevant information that can then be used in the diagnosis, prognosis, drug discovery, drug development or patient stratification in a specific condition.

In some embodiments, the present invention provides a kit with binding elements and one or more modulators to develop patient drug response signatures for signaling response to a drug or potential therapeutics. Such signatures can be useful for predicting patient response to a therapeutic regimen.

In some embodiments, a kit of the invention can be used in multiparametric flow cytometry on cell populations and activation states for diagnosis, prognosis, drug discovery, drug development, and patient stratification.

Table 1 illustrates some combinations of reagents to be included into the kits in some embodiments of the present invention. It should be noted that the table herein is mere for exemplary purpose and does not intend to limit the scope of usage of the present invention. The Target Cell Type column shall refer to both the cell of interest and the source where it is obtained. The Extracellular Marker column shall refer to binding elements to the specific surface markers listed. The Intracellular Marker and Readouts column shall refer to the binding elements specific to the state-specific intracellular markers listed in the column or the dyes listed which bind to intracellular molecules to produce a readout. Kits for other diseases can be assembled with surface and intracellular markers as shown above with the appropriate stains.

In some embodiments, a kit of the invention can include at least two to at least three modulators; and least one to at least three binding elements specific for an intracellular element listed in either one of the combinations of Table 1. In some embodiments, a kit can comprise at least one to at least four modulators; and at least two to at least five binding elements that are specific to intracellular markers listed in either one of the combinations of Table 1. In some embodiments, a kit can comprise at least four to at least six, or at least six to at least eight modulators. In some embodiments, a kit can comprise at least four to at least six, or at least six to at least eight binding elements.

More specifically, kits used for myeloid cells can comprise one or more binding elements specific for the extracellular markers CD11b, CD34, CD45, CD33, CD14, or CD7. Kits used for nucleated red blood cells can comprise one or more binding elements specific for the extracellular markers CD34, CD45, CD71, CD235a, CD235b, CD14, or CD7. Depending on the need of the customer, a kit can further comprise state-specific binding element for an intracellular markers targeted at particular signaling pathways. A kit can further comprise one or more modulators for specific target applications.

For example, if end users want to analyze the JAK/STAT pathway of a leukemia patient's myeloid cell, they have the option to purchase a customized kit having one or more binding elements specific for the cell surface markers CD11b, CD34, CD45, CD33, CD14, or CD7; one or more binding elements specific to the intracellular markers p-STAT1, p-STAT3, or p-STAT5. Alternatively, the customized kit might also include one or more of the modulators that can be IL-27, IL-6, IL-10, IFNa, IFNg, G-CSF, GM-CSF, TPO, or IL-3. In some embodiments, the binding elements are antibodies.

TABLE 1

Exemplary Composition of Kits

| Target Cell Type | Target Pathway | Modulator | Intracellular Markers and Readouts |
|---|---|---|---|
| | Extracellular Markers | | |
| Myeloid Bone Marrow/leukemia | CD11b<br>CD34<br>CD45<br>CD33<br>CD14<br>CD7 | JAK/STAT | IL-27, IL-6, IL-10, IFNa, IFNg, IL-3, G-CSF, GM-CSF, TPO | p-STAT1<br>p-STAT3<br>p-STAT5 |
| Myeloid Bone Marrow/Leukemia | CD11b<br>CD34<br>CD45<br>CD33<br>CD14<br>CD7 | PI3K/Ras-Raf-MAPK | FLT3L<br>SCF<br>IGF-1<br>M-CSF | p-TSC2<br>p-mTor<br>p-AMPK<br>p-S6<br>p-Erk<br>p-Akt<br>p-70S6K<br>p-38<br>p-JNK<br>p-4EBP1 |
| Myeloid Bone Marrow/Leukemia | CD11b<br>CD34<br>CD45<br>CD33<br>CD14<br>CD7 | Apoptosis, DNA Damage | Etoposide<br>Ara-C<br>Daunorubicin<br>Gemtuzumab (such as Gemtuzumab ozogamicin, marketed as Mylotarg)<br>Staurosporine<br>Azacitidine (marketed as Vidaza)<br>Decitabine (marketed as Dacogen)<br>Clofarabine<br>Vorinostat (marketed as Zolinza)<br>Idarubicin<br>Mitoxantrone | Cleaved PARP<br>cytochrome C<br>p-ATM<br>p-ATR<br>p-CHK1<br>p-CHK2<br>p-H2AX<br>p-p53<br>p-Mdm2<br>Cleaved Caspase3<br>Cleaved Caspase 8<br>Survivin<br>XIAP<br>Mcl-1<br>Bcl-2 |
| Myeloid Bone Marrow/Leukemia | CD11b<br>CD34<br>CD45<br>CD33<br>CD14<br>CD7 | Apoptosis, DNA Damage | Etoposide<br>Ara-C<br>Daunorubicin<br>Gemtuzumab (such as Gemtuzumab ozogamicin, | Annexin-V or Yo-Pro<br>Propidium Iodiode<br>Amine Aqua<br>DRAQ5<br>Scatter properties<br>XIAP |

TABLE 1-continued

Exemplary Composition of Kits

| Target Cell Type | Target | Target Pathway | Modulator | Intracellular Markers and Readouts |
|---|---|---|---|---|
| | | | marketed as Mylotarg) Staurosporine Azacitidine (marketed as Vidaza) Decitabine (marketed as Dacogen) Clofarabine Vorinostat (marketed as Zolinza) Idarubicin Mitoxantrone | Survivin Bcl-2 |
| Myeloid Bone Marrow/Leukemia | CD11b CD34 CD45 CD33 CD14 CD7 | Death Receptor Induced Apoptosis | Staurosporine TNFα TRAIL FASL | Annexin-V or Yo-Pro Propidium Iodiode Amine Aqua DRAQ5 Scatter properties |
| Myeloid Bone Marrow/Leukemia | CD11b CD34 CD45 CD33 CD14 CD7 | Death Receptor Induced Apoptosis | Staurosporine TNFα TRAIL FASL | Cleaved PARP Cleaved Caspase 8 Cleaved Caspase 3 Cytochrome C XIAP Survivin Bcl-2 Mcl-1 |
| Myeloid Bone Marrow/Leukemia | CD11b CD34 CD45 CD33 CD14 CD7 | Chemokine Receptors | SDF-1a | p-Akt p-Erk pS6 |
| Myeloid Bone Marrow/Leukemia | CD11b CD34 CD45 CD33 CD14 CD7 | ABL function BCR/ABL function CML monitoring | Imatinib and salts thereof (marketed as Gleevec) | p-CRKL p-Akt p-Erk p-S6 p-Stat1 p-Stat5 |
| Myeloid Bone Marrow/Leukemia | CD11b CD34 CD45 CD33 CD14 CD7 | Phosphatase | Hydrogen Peroxide Sodium pervandate Phenylarsine oxide | p-Akt p-PLCδ2 p-SLP-76 Stat 1, 3, 5 |
| Myeloid Bone Marrow/Leukemia | CD11b CD34 CD45 CD33 CD14 CD7 | Calcium Signaling, PKC | Thapsigargin, PMA | p-S6 p-Erk p-CREB |
| Myeloid Bone Marrow/Leukemia | CD11b CD34 CD45 CD33 CD14 CD7 | Cell Cycle G1/S | Staurosporine Etoposide Ara-C Daunorubicin Gemtuzumab (such as Gemtuzumab ozogamicin, marketed as Mylotarg) Vorinostat (marketed as Zolinza) Azacitidine (marketed as Vidaza) Decitabine (marketed as Dacogen) | CDK4 CDK6 CDK7 Cyclin D1 Cyclin D2 Cyclin D3 Cyclin E Cyclin A NPM (pT199) pRb pE2F |
| Myeloid Bone Marrow/Leukemia | CD11b CD34 | Tumor Suppressors | Staurosporine Etoposide | p15 p16 |

TABLE 1-continued

Exemplary Composition of Kits

| Target Cell Type | Target Pathway | | Modulator | Intracellular Markers and Readouts |
|---|---|---|---|---|
| | CD45 | | Ara-C | p19 |
| | CD33 | | Daunorubicin | p21 |
| | CD14 | | Gemtuzumab | p27 |
| | CD7 | | (such as | p14ARF |
| | | | Gemtuzumab | |
| | | | ozogamicin, | |
| | | | marketed as | |
| | | | Mylotarg) | |
| | | | Vorinostat | |
| | | | (marketed as | |
| | | | Zolinza) | |
| | | | Azacitidine | |
| | | | (marketed as | |
| | | | Vidaza) | |
| | | | Decitabine | |
| | | | (marketed as | |
| | | | Dacogen) | |
| Myeloid Bone Marrow/leukemia | CD11b | Cell Cycle | Staurosporine | DAPI |
| | CD34 | | Etoposide | p-Cdk1 |
| | CD45 | | Ara-C | Cyclin B1 |
| | CD33 | | Daunorubicin | p-Histone H3 |
| | CD14 | | Gemtuzumab | Cyclin D1 |
| | CD7 | | (such as | p15 |
| | | | Gemtuzumab | p16 |
| | | | ozogamicin, | p21 |
| | | | marketed as | |
| | | | Mylotarg) | |
| | | | Azacitidine | |
| | | | (marketed as | |
| | | | Vidaza) | |
| | | | Decitabine | |
| | | | (marketed as | |
| | | | Dacogen) | |
| | | | Vorinostat | |
| | | | (marketed as | |
| | | | Zolinza) | |
| | | | Clofarabine | |
| Myeloid Bone Marrow/leukemia | CD11b | Cell Cycle G2/M | Staurosporine | CDK1 |
| | CD34 | | Nocodozole | Cyclin B1 |
| | CD45 | | Etoposide | CDC25c |
| | CD33 | | Ara-C | Histone H3 |
| | CD14 | | Daunorubicin | Aurora A |
| | CD7 | | Gemtuzumab | Aurora B |
| | | | (such as | NPM |
| | | | Gemtuzumab | Polo like kinases |
| | | | ozogamicin, | Wee 1 |
| | | | marketed as | Myt 1 |
| | | | Mylotarg) | |
| | | | Azacitidine | |
| | | | (marketed as | |
| | | | Vidaza) | |
| | | | Decitabine | |
| | | | (marketed as | |
| | | | Dacogen) | |
| | | | Vorinostat | |
| | | | (marketed as | |
| | | | Zolinza) | |
| Nucleated Red Blood Cells/Bone Marrow | CD34 | JAK/STAT | EPO, TPO, G-CSF, IFN-γ, IL-3, | p-STAT1 |
| | CD45 | | | p-STAT3 |
| | CD71 | | | p-STAT5 |
| | CD235a, | | | |
| | CD235b | | | |
| | CD14 | | | |
| | CD7 | | | |
| Myeloid Bone Marrow/leukemia | CD11b | DNA Methyl transferase (DNMT) Tumor suppressors silenced by DNMTs | Azacitidine (marketed as Vidaza) Decitabine (marketed as Dacogen) | DNMT1 |
| | CD34 | | | DNMT3a |
| | CD45 | | | DNMT3b |
| | CD33 | | | |
| | CD14 | | | |
| | CD7 | | | |
| Nucleated Red Blood Cells/Bone Marrow | CD34 | PI3K/Akt Ras/Raf/Erk PLCg | FLT3L SCF | p-TSC2 |
| | CD45 | | | p-mTor |
| | CD71 | | | p-AMPK |

TABLE 1-continued

Exemplary Composition of Kits

| Target Cell Type | Target | Target Pathway | Modulator | Intracellular Markers and Readouts |
|---|---|---|---|---|
| | CD235a, CD235b CD14 CD7 | | | p-S6 p-Erk p-Akt p-4EP-1 p-PLCg p-38 p-JNK |
| Nucleated Red Blood Cell/Bone Marrow | CD34 CD45 CD71 CD235a, CD235b CD14 CD7 | Death Receptor Induced Apoptosis | Azacitidine (marketed as Vidaza) Decitabine (marketed as Dacogen) Vorinostat (marketed as Zolinza) Lenalidomide EPO EPO + G-CSF | Cleaved PARP p-CHK1 p-CHK2 p-H2AX Cytochrome C Cleaved Caspase 3 Cleaved Caspase 8 p-ATM p-ATR p-p53 Mdm-2 p19 |
| Nucleated Red Blood Cells/Bone Marrow | CD34 CD45 CD71 CD235a, CD235b CD14 CD7 | Death Receptor Induced Apoptosis | TNF-α TRAIL FASL | Cleaved PARP Cytochrome C Cleaved Caspase 8 Cleaved Caspase 3 |
| Nucleated Red Blood Cells/Bone Marrow | CD34 CD45 CD71 CD235a, CD235b CD14 CD7 | Phosphatase | Hydrogen Peroxide Sodium pervanadate Phenlyarsine oxide | p-S6 p-Erk p-Akt p-Stat 1, 3, 5 |
| Nucleated Red Blood Cells/Bone Marrow | CD34 CD45 CD71 CD235a, CD235b CD14 CD7 | Calcium Signaling, PKC | PMA | p-S6 p-Erk PLC-g |
| Nucleated Red Blood Cells/Bone Marrow | CD34 CD45 CD71 CD235a, CD235b CD14 CD7 | Cell Cycle | Staurosporine Etoposide Ara-C Daunorubicin Gemtuzumab (such as Gemtuzumab ozogamicin, marketed as Mylotarg) Azacitidine (marketed as Vidaza) Decitabine (marketed as Dacogen) Vorinostat (marketed as Zolinza) EPO EPO + G-CSF | DAPI p-Cdk1 Cyclin B1 p-Histone H3 Cyclin D1 p15 p16 p21 |
| Megakaryocytes and their progenitors/ Platelets | CD41 CD42b CD61 CD110 (TPO-R, thrombopoietin-receptor) | Differentiation | TPO (thrombopoietin) | p-STAT 3, 5, p-Akt p-Erk |
| T Cells Bone Marrow/ Blood/Lymph Nodes/Spleen/Thymus | CD8+ T cells: CD3 CD45RA CD45RO CD4+ T cells: | (T Cell receptor (TCR) signaling | αCD3/αCD28 αCD3/αCD137 αCD3/αCD44 αCD3/αCD134 | p-ZAP70 p-Lck p-65/RelA p-Erk, p-Akt, |

TABLE 1-continued

Exemplary Composition of Kits

| Target Cell Type | Target Pathway | Modulator | Intracellular Markers and Readouts |
|---|---|---|---|
| T Cells<br>Bone Marrow/<br>Blood/Lymph<br>Nodes/Spleen/Thymus | CD3<br>CD45RA<br>CD45RO<br>CD8+ T cells<br>CD3<br>CD45RA<br>CD45RO<br>CD4+ T cells<br>CD3<br>CD45RA<br>CD45RO | Jak/Stat | Iak/, IL-6, IL-12,<br>IL-2, IL-23, IFNα,<br>IFNγ | p-S6<br>p-PLCγ1<br>p38<br>p-Stat1, 2, 3, 4, 5, 6<br>p38 |
| T Cells<br>Bone Marrow/<br>Blood/Lymph<br>Nodes/Spleen/Thymus | CD8+ T cells<br>CD3<br>CD45RA<br>CD45RO<br>CD4+ T cells<br>CD3<br>CD45RA<br>CD45RO<br>Transcription<br>Factor | TGF-β | TGF-β | p-Akt<br>p-Erk<br>p-S6<br>p-mTor<br>p-38<br>SMADS |
| T Cells<br>Bone Marrow/<br>Blood/Lymph<br>Nodes/Spleen/<br>Thymus | TH1<br>T-bet<br>TH2<br>GATA1<br>GATA3<br>TH17<br>RORγt<br>Treg<br>FOXP3<br>pv 1 | JAK/STAT<br>TGF-β<br>(T Cell receptor<br>(TCR) signaling | IL-6, IL-12, IL-2,<br>IL-23, IFNα,<br>IFN-γ, TGF-β<br>αCD3/αCD28<br>αCD3/αCD137<br>αCD3/αCD44<br>αCD3/αCD134 | p-Stat 1, 2, 3, 4, 5, 6<br>p38<br>p-Akt<br>p-Erk<br>p-JNK<br>p-S6<br>p-mTor<br>p-38<br>SMADS<br>p-ZAP70<br>p-Lck<br>p-65/RelA<br>p-Erk,<br>p-Akt,<br>p-S6<br>p-PLCγ1 |

In some embodiments, myeloid cell kits directed to the JAK/STAT signaling pathway can comprise at least one binding element specific for a cell surface marker CD11b, CD34, CD45, CD33, CD14, or CD7; and at least one binding element specific for an intracellular marker p-STAT1, p-STAT3, or p-STAT5. A kit can optionally comprise at least one modulator IL-3, IL-27, IL-6, IL-10, IFNα, IFNγ, G-CSF, GM-CSF, or TPO. In some embodiments, myeloid cell kits directed to the JAK/STAT signaling pathway comprise a cell surface marker CD11b, CD34, CD45, CD33, CD14, or CD7; binding elements specific for p-STAT1, p-STAT3, and p-STAT5; and at least two of the following modulators: IL-3, IL-27, IL-6, IL-10, IFNα, IFNγ, G-CSF, GM-CSF, or TPO. In some embodiments, the binding elements are antibodies.

In some embodiments, myeloid cell kits directed to PI3K/Raf-Ras-MAPK pathway can comprise at least one binding element specific for a cell surface marker CD11b, CD34, CD45, CD33, CD14, or CD7; and at least one binding element specific for an intracellular marker p-TSC2, p-mTor, p-AMPK, p-S6, p-Erk, p-Akt, or p-4EP-1. The kits can optionally comprise at least one modulator FLT3L, SCF, or IGF-1. In some embodiments, a myeloid cell kit directed to PI3K/Raf-Ras-MAPK pathway comprise at least one binding element specific for a cell surface marker CD11b, CD34, CD45, CD33, CD14, or CD7; at least three binding elements specific for the intracellular markers p-TSC2, p-mTor, p-AMPK, p-S6, p-Erk, p-Akt, or p-4EP-1; and least two of the following modulators: FLT3L, SCF, or IGF-1. In some embodiments, the binding elements are antibodies.

In some embodiments, myeloid cell kits directed to the intrinsic apoptosis and DNA damage-induced apoptosis pathways can comprise at least one binding element specific for a cell surface marker CD11b, CD34, CD45, CD33, CD14, or CD7; at least one binding element specific for an intracellular marker cleaved Cleaved PARP, cytochrome C, p-ATM, p-ATR, p-CHK1, p-CHK2, p-H2AX, p-p53, Cleaved Caspase 3 or Cleaved Caspase 8. The kits can optionally comprise at least one modulator Etoposide, Ara-C, Daunorubicin, Gemtuzumab (such as Gemtuzumab ozogamicin, marketed as Mylotarg), or Staurosporin. In some embodiments, myeloid cell kits directed to the intrinsic apoptosis and DNA damage-induced apoptosis pathways comprise at least one binding element specific for a cell surface marker CD11b, CD34, CD45, CD33, CD14, or CD7; at least three binding elements specific for the intracellular markers cleaved Cleaved PARP, cytochrome C, p-ATM, p-ATR, p-CHK1, p-CHK2, p-H2AX, p-p53, Cleaved Caspase 3 or Cleaved Caspase 8; and at least two of the following modulators: Etoposide, Ara-C, Daunorubicin, Gemtuzumab (such as Gemtuzumab ozogamicin, marketed as Mylotarg), or Staurosporin. The kits can also optionally comprise at least one dye of Annexin-V, Yo-Pro, propidium iodide (PI), Amine Aqua, DRAQ5, or XIAP. In some embodiments, the binding elements are antibodies.

In some embodiments, myeloid cell kits directed to the extrinsic apoptosis and DNA damage-induced apoptosis pathways can comprise at least one binding element selected specific for a cell surface marker CD11b, CD34, CD45, CD33, CD14, or CD7; at least one binding element specific for an intracellular marker cleaved PARP, cleaved Caspase 8, cleaved Caspase 3, cytochrome C, XIAP or Survivin. The kits can optionally comprise at least one modulator Staurosporine, TNF, TNFα, TRAIL, or FASL. In some embodiments, myeloid cell kits directed to the extrinsic apoptosis and DNA damage-induced apoptosis pathways comprise at least one binding element selected specific for a cell surface marker CD11b, CD34, CD45, CD33, CD14, or CD7; at least three binding elements specific for the intracellular pathways cleaved PARP, cleaved Caspase 8, cleaved Caspase 3, cytochrome C, XIAP or Survivin; and at least two modulators Staurosporine, TNF, TNFα, TRAIL, or FASL. The kits can also optionally comprise at least one dye Annexin-V, Yo-Pro, propidium iodide (PI), Amine Aqua, DRAQ5, or XIAP. In some embodiments, the binding elements are antibodies.

In some embodiments, myeloid cell kits directed to measure chemokine signaling can comprise at least one binding element specific for a cell surface marker of CD11b, CD34, CD45, CD33, CD14, or CD7; at least one binding element specific for an intracellular marker of p-Akt, p-Erk, or p-S6. The kits can optionally comprise SDF-1α as a modulator. In some embodiments, myeloid cell kits directed to measure chemokine signaling comprise at least one binding element specific for a cell surface marker CD11b, CD34, CD45, CD33, CD14, or CD7; binding elements specific for p-Akt, p-Erk, and p-S6; and SDF-1α as a modulator. In some embodiments, the binding elements are antibodies.

In some embodiments, myeloid cell kits directed to measure ABL function or BCR/ABL function for chronic myelogenous leukemia (CML) monitoring may comprise at least one binding element specific for a cell surface marker CD11b, CD34, CD45, CD33, CD14, or CD7; and at least three binding elements specific the for the intracellular markers p-CRKL, p-Akt, p-Erk, p-S6, p-Stat1 or p-Stat5. The kits can optionally comprise a therapeutic agent Imatinib and salts thereof (marketed as Gleevec). In some embodiments, the binding elements are antibodies.

In some embodiments, myeloid cell kits directed to phosphatase function can comprise at least one binding element specific for a cell surface marker CD11b, CD34, CD45, CD33, CD14, or CD7; at least one binding element specific for an intracellular marker p-Akt, p-PLCδ2, p-SLP-76, Stat 1, Stat 3, or Stat 5. The kits can optionally comprise hydrogen peroxide, sodium pervandate or phenylarsine oxide as a modulator. In some embodiments, myeloid cell kits directed to phosphatase function comprise at least one binding element specific for a cell surface marker CD11b, CD34, CD45, CD33, CD14, or CD7; at least three binding elements specific for the intracellular markers p-Akt, p-PLCδ2, p-SLP-76, Stat 1, Stat 3, or Stat 5; and sodium pervandate or phenylarsine oxide as a modulator. In some embodiments, the binding elements are antibodies.

In some embodiments, myeloid cell kits directed to measure calcium signaling pathway and PKC function can comprise at least one binding element specific for a cell surface marker CD11b, CD34, CD45, CD33, CD14, or CD7; at least one binding element specific for an intracellular marker p-S6, p-Erk, or p-CREB. The kits can optionally comprise at least one modulator of Thapsigargin or phorbol myristate acetate (PMA). In some embodiments, the binding elements are antibodies.

In some embodiments, myeloid cell kits directed to measure cell cycle G1/S can comprise at least one binding element specific for a cell surface marker CD11b, CD34, CD45, CD33, CD14, or CD7; at least one binding element specific for an intracellular marker CDk4, CDK6, Cyclin D1, Cyclin E, Cyclin A, NPM (pT199), Rb or E2F. The kits can optionally comprise at least one modulator of Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, myeloid cell kits directed to measure cell cycle G1/S comprise at least one binding element specific for a cell surface marker CD11b, CD34, CD45, CD33, CD14, or CD7; at least three binding elements specific for an intracellular marker CDk4, CDK6, Cyclin D1, Cyclin E, Cyclin A, NPM (pT199), Rb or E2F; and at least two of the following modulators: Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, the binding elements are antibodies.

In some embodiments, myeloid cell kits directed to measure tumor suppressors can comprise at least one binding element specific for a cell surface marker CD11b, CD34, CD45, CD33, CD14, or CD7; at least one binding element specific for an intracellular marker p15, p16, p21 or p27. The kits can optionally comprise at least one modulator of Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, myeloid cell kits directed to measure tumor suppressors comprise at least one binding element specific for a cell surface marker CD11b, CD34, CD45, CD33, CD14, or CD7; at least three binding elements specific for an intracellular marker p15, p16, p21 or p27; and at least two of the following modulators: Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, the binding elements are antibodies.

In some embodiments, myeloid cell kits directed to measure cell cycle can comprise at least one binding element specific for a cell surface marker CD11b, CD34, CD45, CD33, CD14, or CD7; at least one binding element specific for an intracellular marker DAPI, p-Cdk1, Cyclin B1, Cyclin D1, p-Histone H3, p15, p16, or p21. The kits can optionally comprise at least one modulator of Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, myeloid cell kits directed to measure cell cycle comprise at least one binding element specific for a cell surface marker CD11b, CD34, CD45, CD33, CD14, or CD7; at least three binding elements specific for an intracellular marker DAPI, p-Cdk1, Cyclin B1, Cyclin D1, p-Histone H3, p15, p16, or p21; and at least two of the following modulators: Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, the binding elements are antibodies.

In some embodiments, myeloid cell kits directed to measure cell cycle G2/M can comprise at least one binding element specific for a cell surface marker CD11b, CD34, CD45, CD33, CD14, o CD7; at least one binding element specific for an intracellular marker p-Cdk1, Cyclin B1, CDC25c1, p-Histone H3, Aurora A, Aurora B, NPM, Polo like kinases, Wee 1 or Myt 1. The kits can optionally comprise at least one modulator of Staurosporine, Nocodozole, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, myeloid cell kits directed to measure cell cycle G2/M comprise at least one binding element specific for a cell surface marker CD11b, CD34, CD45, CD33, CD14, or CD7; at least three binding elements specific for an intracellular marker p-Cdk1, Cyclin B1, CDC25c1, p-Histone H3, Aurora A, Aurora B, NPM, Polo like kinases, Wee 1 or Myt 1; and at least two of the following modulators: Staurosporine, Nocodozole, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), or Vorinostat (marketed as Zolinza). In some embodiments, the binding elements are antibodies.

In some embodiments, myeloid cell kits directed to measure DNMT function and/or tumor suppressors silenced by DNMTs can comprise at least one binding element specific for a cell surface marker CD11b, CD34, CD45, CD33, CD14, or CD7; at least one binding element specific for an intracellular marker DNMT1, DNMT3a or DNMT3b. The kits can optionally comprise at least one modulator of Azacitidine (marketed as Vidaza), or Decitabine (marketed as Dacogen). In some embodiments, the binding elements are antibodies.

In some embodiments, nucleated red blood cell (nRBC) kits directed to the JAK/STAT signaling pathway can comprise at least one binding element specific for a cell surface marker CD7, CD14, CD34, CD45, CD71, CD235a, or CD235b; and at least one binding element specific for an intracellular marker p-STAT1, p-STAT3, or p-STAT5. The kits can optionally comprise at least one modulator of EPO, TPO, G-CSF, IFN-γ, or IL-3. In some embodiments, nucleated red blood cell (nRBC) kits directed to the JAK/STAT signaling pathway comprise at least one binding element specific for a cell surface marker CD7, CD14, CD34, CD45, CD71, CD235a, or CD235b; binding elements specific for p-STAT1, p-STAT3, and p-STAT5; and at least two of the following modulators: EPO, TPO, G-CSF, IFN-γ, or IL-3. In some embodiments, the binding elements are antibodies.

In some embodiments, nRBC kits directed to PI3K/Akt, Raf/Ras/Erk and or PLCg pathways comprise at least one binding element specific for a cell surface marker CD7, CD14, CD34, CD45, CD71, CD235a, or CD235b; and at least one binding element specific for an intracellular marker p-TSC2, p-mTor, p-AMPK, p-S6, p-Erk, p-Akt, p-4EP-1 or p-PLCg. The kits can optionally comprise at least one modulator of FLT3L or SCF. In some embodiments, the nRBC kits directed to PI3K/Akt, Raf/Ras/Erk and or PLCg pathways comprise at least three binding elements specific for the intracellular markers p-TSC2, p-mTor, p-AMPK, p-S6, p-Erk, p-Akt, p-4EP-1 or p-PLCg. In some embodiments, the binding elements are antibodies.

In some embodiments, nRBC kits directed to measure intrinsic apoptosis pathway and DNA damage induced apoptosis pathway can comprise at least one binding element specific for a cell surface marker CD7, CD14, CD34, CD45, CD71, CD235a, or CD235b; and at least one binding element specific for an intracellular marker PARP, p-CHK1, p-CHK2, p-H2AX, Cytochrome C, cleaved Caspase 3, cleaved Caspase 8, p-ATM, p-ATR, or p-p53. The kits can optionally comprise at least one therapeutic agent of Azacitidine (marketed as Vidaza), Decitabine (marketed as Dacogen), Vorinostat (marketed as Zolinza), Lenalidomide, EPO or EPO plus G-CSF. In some embodiments, nRBC kits directed to measure intrinsic apoptosis pathway and DNA damage induced apoptosis pathway comprise at least one binding element specific for a cell surface marker CD7, CD14, CD34, CD45, CD71, CD235a, or CD235b; at least three binding elements specific for intracellular markers cleaved PARP, p-CHK1, p-CHK2, p-H2AX, Cytochrome C, cleaved Caspase 3, cleaved Caspase 8, p-ATM, p-ATR, or p-p53; and at least two therapeutic agents of Azacitidine (marketed as Vidaza), Decitabine (marketed as Dacogen), Vorinostat (marketed as Zolinza), Lenalidomide, EPO and EPO plus G-CSF. In some embodiments, the binding elements are antibodies.

In some embodiments, nRBC kits directed to measure extrinsic apoptosis and induced apoptosis pathways can comprise at least one binding element specific for a cell surface marker CD7, CD14, CD34, CD45, CD71, CD235a, or CD235b; and at least one binding element specific for an intracellular marker cleaved PARP, Cytochrome C, cleaved Caspase 3 or cleaved Caspase 8. The kit can optionally comprise at least one modulator of TNF-α, TRAIL, or FASL. In some embodiments, nRBC kits directed to measure extrinsic apoptosis and induced apoptosis pathways comprise at least one binding element specific for a cell surface marker CD7, CD14, CD34, CD45, CD71, CD235a, or CD235b; at least three binding elements specific for the intracellular markers cleaved PARP, Cytochrome C, cleaved Caspase 3 or cleaved Caspase 8; and at least two of the following modulators: TNF-α, TRAIL, or FASL. In some embodiments, the binding elements are antibodies.

In some embodiments, nRBC kits directed to measure phosphatase function may comprise at least one binding element specific for a cell surface marker CD7, CD14, CD34, CD45, CD71, CD235a, or CD235b; and at least one binding element specific for an intracellular marker p-S6, p-Erk, p-Akt, p-Stat 1, p-Stat 3 or p-Stat 5. The kit can optionally comprise hydrogen peroxide, sodium pervanadate or phenylarsine oxide as a modulator. In some embodiments, nRBC kits directed to measure phosphatase function can comprise at least one binding element specific for a cell surface marker CD7, CD14, CD34, CD45, CD71, CD235a, or CD235b; at least three binding elements specific for an intracellular marker p-S6, p-Erk, p-Akt, p-Stat 1, p-Stat 3 or p-Stat 5; and hydrogen peroxide, sodium pervanadate or phenylarsine oxide as a modulator. In some embodiments, the binding elements are antibodies.

In some embodiments, nRBC kits directed to calcium signaling and PKC function can comprise at least one binding element specific for a cell surface marker CD7, CD14, CD34, CD45, CD71, CD235a, or CD235b; and at least one binding element specific for an intracellular marker p-S6, p-Erk, p-Akt, p-STAT1, p-STAT3, or p-STAT5. The kit can optionally comprise PMA as a modulator. In some embodiments, the nRBC kits directed to calcium signaling and PKC function comprise at least three binding elements specific for the intracellular markers p-S6, p-Erk, p-Akt, p-STAT1, p-STAT3, or p-STAT5; and PMA. In some embodiments, the binding elements are antibodies.

In some embodiments, nRBC kits directed to measure cell cycle may comprise at least one binding element specific for a cell surface marker CD7, CD14, CD34, CD45, CD71, CD235a, or CD235b; and at least one binding element specific for an intracellular marker DAPI, p-Cdk1, Cyclin B1, Cyclin D1, p-Histone H3, p15, p16, or p21. The kit can optionally comprise at least one modulator of Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), Vorinostat (marketed as Zolinza), EPO or EPO plus G-CSF. In some embodiments, nRBC kits directed to measure cell cycle comprise at least one binding element specific for a cell surface marker CD7, CD14, CD34, CD45, CD71, CD235a, or CD235b; at least three binding elements specific for an intracellular marker DAPI, p-Cdk1, Cyclin B1, Cyclin D1, p-Histone H3, p15, p16, or p21; and at least two of the following modulators: Staurosporine, Etoposide, Ara-C, Daunorubicin, Gemtuzumab (such as Gemtuzumab ozogamicin, marketed as Mylotarg), Azacitidine (marketed as Vidaza), Decitabine (marketed as Dacogen), Vorinostat (marketed as Zolinza), EPO or EPO plus G-CSF. In some embodiments, the binding elements are antibodies.

In some embodiments, T cell kits directed to measure T cell receptor signaling can comprise at least one binding element specific for a cell surface marker CD7, CD3, CD45RA, or CD45RO; and at least one binding element specific for an intracellular marker p-ZAP70, p-Lck, p-65/RelA, p-Erk, p-Akt, p-S6 or p-PLCγ1. The kit can optionally comprise one binding element specific for a cell surface marker specific for CD8 T cells or CD4 T cells such as one binding element specific for CD8 or CD4. The kit can optionally comprise one binding element specific for a cell surface marker specific for TH1 such as T-bet; a binding element specific for a cell surface marker specific for TH2 such as GATA3; binding element specific for a cell surface marker specific for TH17 such as RORγt; and/or a binding element specific for a cell surface marker specific for Treg such as FOXP3. The kit can optionally comprise at least one modulator of αCD3/αCD28, αCD3/αCD137, αCD3/αCD44 or αCD3/αCD134. In some embodiments, T cells kits directed to measure T cell receptor signaling comprise at least one binding element specific for a cell surface marker CD3, CD45RA, or CD45RO; at least three binding elements specific for an intracellular marker p-ZAP70, p-Lck, p-65/RelA, p-Erk, p-Akt, p-S6 or p-PLCγ1; and at least two of the following modulators: CD3/αCD28, αCD3/αCD137, αCD3/αCD44 or αCD3/αCD134. In some embodiments, the binding elements are antibodies.

In some embodiments, T cell kits directed to measure Jak/Stat signaling pathway can comprise at least one binding element specific for a cell surface marker CD7, CD3, CD45RA, or CD45RO; and at least one binding element specific for an intracellular marker p-Stat1, p-Stat 2, p-Stat 3, p-Stat 4, p-Stat 5, p-Stat 6 or p38. The kit can optionally comprise one binding element specific for a cell surface marker specific for CD8 T cells or CD4 T cells such as one binding element specific for CD8 or CD4. The kit can optionally comprise one binding element specific for a cell surface marker specific for TH1 such as T-bet; a binding element specific for a cell surface marker specific for TH2 such as GATA3; binding element specific for a cell surface marker specific for TH17 such as RORγt; and/or a binding element specific for a cell surface marker specific for Treg such as FOXP3. The kit can optionally comprise at least one modulator of IL-6, IL-12, IL-2, IL-23, IFNα, IFNγ. In some embodiments, T cells kits directed to measure Jak/Stat signaling pathway comprise at least one binding element specific for a cell surface marker CD3, CD45RA, or CD45RO; at least three binding elements specific for an intracellular marker p-Stat1, p-Stat 2, p-Stat 3, p-Stat 4, p-Stat 5, p-Stat 6 o p38; and at least two of the following modulators: Iak, IL-6, IL-12, IL-2, IL-23, IFNα, IFNγ. In some embodiments, when the kits contain a binding elements specific for p-p38, the kits also contains IFNα and IFNγ as modulators. In some embodiments, the binding elements are antibodies.

In some embodiments, T cell kits directed to measure TGF-β signaling pathway can comprise at least one binding element specific for a cell surface marker CD7, CD3, CD45RA, or CD45RO; and at least one binding element specific for an intracellular marker p-Akt, p-Erk, p-S6, p-mTor, p-38 or SMADS. The kit can optionally comprise one binding element specific for a cell surface marker specific for CD8 T cells or CD4 T cells such as one binding element specific for CD8 or CD4. The kit can optionally comprise one binding element specific for a cell surface marker specific for TH1 such as T-bet; a binding element specific for a cell surface marker specific for TH2 such as GATA3; binding element specific for a cell surface marker specific for TH17 such as RORγt; and/or a binding element specific for a cell surface marker specific for Treg such as FOXP3. The kit can optionally comprise TGF-β as a modulator. In some embodiments, T cells kits directed to measure TGF-β signaling pathway comprise at least one binding element specific for a cell surface marker CD3, CD45RA, or CD45RO; at least three binding elements specific for an intracellular marker p-Akt, p-Erk, p-S6, p-mTor, p-38 or SMADS. In some embodiments, the binding elements are antibodies.

In some embodiments, the kits of the invention are directed to hematologic malignancies, e.g. for diagnosis, prognosis, drug discovery, drug development, and patient stratification of such malignancies. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the kits of the invention include multiple myeloma, amyloidosis and Waldenstrom's macroglobulinemia.

Leukemias that may be evaluated by the kits of the invention include both myeloid and lymphoid leukemias. Myeloid leukemias include AML, CML, and juvenile myelomonocytic leukemia (JMML). Lymphoid leukemias include non-B cell acute lymphocytic leukemia (T-ALL), and B cell acute lymphoblastic leukemia (including pre-B cell) and chronic lymphocytic leukemia (CLL). Other hematologic diseases and disorders that may be evaluated by the kits of this invention include myeloid disorders such as myelodysplastic disorders, myeloproliferative disorders, myelofibroses, polycythemias, and thrombocythemias and others such as B cell immunoproliferations (post transplant lymphoproliferation disorder (PTLD) and non-B atypical immune lymphoproliferations. See Haskell et al, Cancer Treatment, 5th Ed., W.B. Saunders and Co., 2001.

In some embodiments of the invention, the hematologic disease that is evaluated by the kits of the invention is CLL. In some embodiments of the invention, the hematologic disease that is evaluated by the kits of the invention is AML. In some embodiments of the invention, the hematologic disease that is evaluated by the kits of the invention is ALL. In some embodiments of the invention, the hematologic disease that is evaluated by the kits of the invention is CML. In some embodiments of the invention, the hematologic disease that is evaluated by the kits of the invention is follicular lymphoma. In some embodiments of the invention, the hematologic disease that is evaluated by the kits of the invention is mantle cell lymphoma. In some embodiments of the invention, the hematologic disease that is evaluated by the kits of the invention is multiple myeloma. In some embodiments of the invention, the hematologic disease that is evaluated by the kits of the invention is MPN. In some embodiments of the invention, the hematologic disease that is evaluated by the kits of the invention is MDS.

Table 2 illustrates some combinations of reagents to be included into the kits directed to MDS, e.g. for diagnosis, prognosis, drug discovery, drug development, and patient stratification. In this example, the kits of the present invention comprise binding element cocktails to be used in the study of a MDS patient's myeloid cells and nucleated red blood cells. In one embodiment, the kits includes binding elements specific to activatable elements in the JAK/STAT signalling pathway and binding elements specific to the extracellular markers CD33, CD34, and CD45. In some embodiments, the activatable elements in the JAK/STAT signalling pathway are p-STAT1, p-STAT3, and p-STAT5. Thus, in some embodiments, the kits for diagnosis, prognosis, drug discovery, drug development, and patient stratification of MDS comprises binding elements specific for p-STAT1, p-STAT3, and p-STAT5 and binding elements specific to the extracellular markers CD33, CD34, and CD45. In some embodiments, the binding elements are antibodies.

In some embodiments, the invention includes MDS kits to measure intrinsic apoptosis as illustrated in Table 2. The kits include cocktails of binding elements that recognize four extracellular markers—CD34, CD45, CD235a and CD235b—and three intracellular markers—cleaved PARP, p-Chk2, and p-PH2ax. Each binding element is conjugated with a fluorescent label and can be detected by multiparametric flow cytometer to resolve the difference between treated and untreated cells with high precision and specificity. In some embodiments, the binding elements are antibodies.

TABLE 2

MDS Binding Elements and Cocktails Kits

| Target Cell Type | Target pathway | Extracellular marker | Intracellular marker |
|---|---|---|---|
| Myeloid cell/bone marrow | JAK/STAT | CD33-PE CD34-PerCP CD45-Alexa700 | p-STAT1 - Alexa488 p-STAT3 - PacBlue p-STAT5 - Alexa647 |
| Nucleated red blood cell (nRBC) | Intrinsic apoptosis | CD34-PerCP CD45-Alexa700 CD235ab-PE CD71 | Cleaved PARP - Alexa647 p-Chk2 - PacBlue p-H2AX - Alexa488 |

In some embodiments, the invention includes MDS kits to measure signaling pathways in megakaryocytes and their progenitors, which give rise to platelets. Megakaryocytes and their progenitors are present in bone marrow, while platelets will be most prominent in the peripheral blood. The kits can include binding elements that recognize three of the extracellular markers CD41, CD42b, CD61, o CD110 (TPO-R, thrombopoietin-receptor); at least three of the binding elements specific for the intracellular markers p-STAT 3, p-STAT 5, p-Akt or p-42/44 MAPK; and TPO (thrombopoietin) as a modulator.

Table 3 illustrates some combinations of reagents to be included into the kits directed to AML, e.g., for diagnosis, prognosis, drug discovery, drug development, and patient stratification. In this example, the kits of the present invention comprise binding element cocktails to be used in the study of AML patients' myeloid cells. In some embodiments, the kits of the invention include at least two to at least three modulators and least one to at least three binding elements specific for an intracellular element listed in Table 3. In some embodiments, a kit can comprise at least one to at least four modulators and at least two to at least five binding elements that are specific to five of the intracellular markers listed in Table 1. In some embodiments, a kit can comprise at least four to at least six, or at least six to at least eight, or at least nine to at a least thirteen modulators. In some embodiments, a kit can comprise at least four to at least six, or at least six to at least eight, or at least nine to at least 11 binding elements.

In one embodiment, the kits include binding elements specific to the extracellular markers CD34, CD45, CD71, CD235a, CD235b, CD 14, CD 7, FLT3, Kit, SCF receptor or Drug Transporters such as MDR1, BCRP, MRP1. In some embodiments, the kits include binding elements specific to the activatable elements p-STAT1, p-STAT3, p-STAT5, Cleaved PARP, p-Erk, p-Akt, p-S6, p-Chk2, p-pH2ax, Caspase 3, or Cytosolic cytochrome C. In some embodiments, a kit can comprise at least two modulators and at least three binding elements that are specific to three of the intracellular markers listed in either one of the combinations of Table 3. In some embodiments, a kit can comprise at least two modulators and at least five binding elements that are specific to five of the intracellular markers listed in either one of the combinations of Table 3. In some embodiments, a kit can comprise at least one binding elements specific to the extracellular marker CD34, CD45, CD71, CD235a, CD235b, CD 14, or CD 7; at least one binding element of FLT3, Kit, SCF receptor or Drug Transporters such as MDR1, BCRP, MRP1; at least three binding elements of p-STAT1, p-STAT3, p-STAT5, Cleaved PARP, p-Erk, p-Akt, p-S6, p-Chk2, p-H2AX, Caspase 3, or Cytosolic cytochrome C; and at least at least two of the following modulators: FLT3L, SCF, GCSF, GMCSF, IL-6, IL-10, IFN alpha, or IFN gamma.

TABLE 3

AML Binding Elements and Cocktails Kits

| Target Cell Type | Extracellular marker | Modulator | Intracellular marker |
|---|---|---|---|
| Myeloid cell/bone marrow | CD34 | FLT3L | p-STAT1 |
| | CD45 | SCF | p-STAT3 |
| | CD71 | GCSF | p-STAT5 |
| | CD235a | GMCSF | Cleaved PARP |
| | CD14 | IL-27 | p-Erk |
| | CD7 | IL-6 | p-Akt |
| | FLT3 | IL-10 | p-S6 |
| | c-KIT | IFN alpha | p-Chk2 |
| | SCF receptor | IFN gamma | p-H2AX |
| | Drug Transporters (MDR1, BCRP, MRP1) | Staurosporine AraC/daunorubicin Etoposide | Caspase 3 Cytosolic cytochrome C |

TABLE 3-continued

AML Binding Elements and Cocktails Kits

| Target Cell Type | Extracellular marker | Modulator | Intracellular marker |
|---|---|---|---|
| | | Gemtuzumab (such as Gemtuzumab ozogamicin, marketed as Mylotarg) Zolinza | |

In some embodiments, the invention provides kits directed to measuring the JAK/STAT signaling pathway in different cell types, e.g., for diagnosis, prognosis, drug discovery, drug development, and patient stratification. The cell types to be analyzed with the kits may be selected according to the condition being studied. One or more cell types may be analyzed in a given condition for diagnosis, prognosis, drug discovery, drug development, and patient stratification in the condition. For instance, when diagnosing AML the JAK/STAT signaling pathway can be measured using the kits described herein in myeloid cells alone or in combination with other cell types such as B or T lymphocytes in order to make a diagnosis, prognosis, drug discovery, drug development, and patient stratification. Table 4 illustrates some combinations of reagents to be included into the kits directed to measuring the JAK/STAT signaling pathway. In some embodiments, a kit can comprise at least two modulators and at least three binding elements that are specific to three of the intracellular markers listed in either one of the combinations of Table 4. In some embodiments, a kit can comprise at least two modulators and at least five binding elements that are specific to five of the intracellular markers listed in either one of the combinations of Table 4. In some embodiments, the kits of the invention include at least two to at least three modulators; and least one to at least three binding elements specific for an intracellular element listed in either one of the combinations of Table 4. In some embodiments, a kit can comprise at least one to at least three modulators; and at least two to at least five binding elements that are specific to intracellular markers listed in either one of the combinations of Table 4.

The JAK/STAT kits can also include controls such as lyophilized cell lines and protocols. These kits are useful, for example, for testing JAK-STAT inhibitors.

TABLE 4

| Cell Types | Cell Surface Markers | Modulator | Intracellular Markers and Epitopes |
|---|---|---|---|
| T cells | CD3, CD4, CD8, CD45RA, CD45RO | IFN alpha<br>IFN gamma<br>IL-2<br>IL-4<br>IL-6<br>Il-27 | p-STAT1 (pY701; pS727)<br>p-STAT2 (pY690)<br>p-STAT3 (pY705; pS727)<br>p-STAT4 (pY693)<br>p-STAT5 (pY694)<br>p-STAT6 (pY641) |
| Monocytes | CD11b, CD15, CD33, CD34, CD45 | IFN alpha<br>IFN gamma<br>GM-CSF<br>IL-4<br>IL-6<br>IL-27<br>G-CSF | p-STAT1 (pY701; pS727)<br>p-STAT2 (pY690)<br>p-STAT3 (pY705; pS727)<br>p-STAT4 (pY693)<br>p-STAT5 (pY694)<br>p-STAT6 (pY641) |
| Bone Marrow (T Cells, Monocytes, nRBCs, Stem Cells, and Megakaryocytes/Megakaryocyte-precursors) | CD11b, CD15, CD33, CD34, CD41, CD42b CD45, CD61, CD71, CD110, CD235a, CD235b | IFN alpha<br>IFN gamma<br>GM-CSF<br>G-CSF<br>TPO<br>IL-4<br>IL-6<br>IL-27 | p-STAT1 (pY701; pS727)<br>p-STAT2 (pY690)<br>p-STAT3 (pY705; pS727)<br>p-STAT4 (pY693)<br>p-STAT5 (pY694)<br>p-STAT6 (pY641) |
| PBMC | CD11b, CD15, CD33, CD34, CD45 | IFN alpha<br>IFN gamma<br>GM-CSF | p-STAT1 (pY701; pS727)<br>p-STAT2 (pY690)<br>p-STAT3 (pY705; pS727)<br>p-STAT4 (pY693)<br>p-STAT5 (pY694)<br>p-STAT6 (pY641) |
| Stem Cells | CD34, CD117, Lin(—) | IFN alpha<br>IFN gamma<br>FLT3L | p-STAT1 (pY701; pS727)<br>p-STAT2 (pY690)<br>p-STAT3 (pY705; pS727)<br>p-STAT4 (pY693)<br>p-STAT5 (pY694)<br>p-STAT6 (pY641) |
| T cells | CD3, CD4, CD8, CD45RA, CD45RO | IL-6 | p-STAT3 (pY705; pS727)<br>p-STAT1 (pY701; pS727) |
| B cells | CD20, CD19, CD79a, IgM, IgD, CD5, CD3, Kappa light chain, | IL-6 | p-STAT3 (pY705; pS727)<br>p-STAT1 (pY701; pS727) |

TABLE 4-continued

| Cell Types | | Modulator | Intracellular Markers and Epitopes |
|---|---|---|---|
| macrophages | Lambda light chain CD11b, CD15, CD33, CD34, CD45 | IL-10 | p-Stat4 p-Stat3 |
| B cells | CD20, CD19, CD79a, IgM, IgD, CD5, CD3, Kappa light chain and Lambda light chain | IL-4 | p-Stat 6 p-Stat5 |
| TH2 | CD3, CD4, CD8, CD45RA, CD45RO, GATA3 | IL-4 | p-Stat 6 p-Stat5 |
| Bone Marrow | CD34, CD117 | IL-3 | p-Stat1 p-Stat 3 p-Stat5 p-Stat6 |
| | Transcription Factor | | |
| TH2 | GATA3 | IL-4 | p-Stat 6 p-Stat 5 |

In some embodiments, the invention provides kits directed to measuring the PI3K signaling pathway in different cell types, e.g., for diagnosis, prognosis, drug discovery, drug development, and patient stratification. The cell types to be analyzed with the kits may be selected according to the condition being studied. One or more cell types may be analyzed in a given condition for diagnosis, prognosis, drug discovery, drug development, and patient stratification in the condition. Table 5 illustrates some combinations of reagents to be included into the kits directed to measuring the PI3K signaling pathway. In some embodiments, a kit can comprise at least two modulators and at least three binding elements that are specific to three of the intracellular markers listed in either one of the combinations of Table 5. In some embodiments, a kit can comprise at least two modulators and at least five binding elements that are specific to five of the intracellular markers listed in either one of the combinations of Table 5. In some embodiments, the kits of the invention include at least two to at least three modulators; and least one to at least three binding elements specific for an intracellular element listed in either one of the combinations of Table 5. In some embodiments, a kit can comprise at least one to at least four modulators; and at least two to at least five binding elements that are specific to intracellular markers listed in either one of the combinations of Table 5. In some embodiments, a kit can comprise at least four to at least six, or at least six to at least eight modulators. In some embodiments, a kit can comprise at least four to at least six, or at least six to at least nine binding elements.

The PI3K kits can also include controls such as lyophilized cell lines and protocols.

TABLE 5

| PI3K signaling pathway | | | |
|---|---|---|---|
| Cell Types | Cell Surface Markers | Modulator | Intracellular Markers and Epitopes |
| T cells | CD3, CD4, CD8, CD45RA, CD45RO | FLT3L SCF | pAKT (pT308; pS473) |
| Monocytes | CD11b, CD15, CD33, CD34, CD45 | SDF1α GCSE | TSC2 (pS1086/pS1088; |
| Bone Marrow (T Cells, Monocytes, nRBCs, Stem Cells, and Megakaryocytes/Megakaryocyte-precursors) | CD11b, CD15, CD33, CD34, CD41, CD42b CD45, CD61, CD71, CD110, CD235a, CD235b | GM-CSF G-CSF Epo IL-6 IL-27 Solid tumors | pS1798; pS939; pT1422; pY1571) BAD (pS112; pS155; pS75; pS99; pS136) pRAS-40 (T246) 4EBP1 (pT36/pT45; |
| PBMC | CD11b, CD15, CD33, CD34, CD45 | EGF IGF1 | pT69) FOXO1A (pS256; |
| Stem Cells | CD34, CD117 | Met FGF VEGF | pS322) FOXO3a (pS253; pS315; pT32) GSK3β (pS9) pS6 (pS240/244; pS9; pS235/pS236) |

In some embodiments, the invention provides kits directed to measuring metabolism in different cell types, e.g., for diagnosis, prognosis, drug discovery, drug development, and patient stratification. The cell types to be analyzed with the kits may be selected according to the condition being studied. One or more cell types may be analyzed in a given condition for diagnosis, prognosis, drug discovery, drug development, and patient stratification in the condition. Table 6 illustrates some combinations of reagents to be included into the kits directed to measuring the metabolism. In some embodiments, a kit can comprise at least two modulators and at least three binding elements that are specific to three of the intracellular markers listed in either one of the combinations of Table 6. In some embodiments, a kit can comprise at least two modulators and at least five binding elements that are specific to five of the intracellular markers listed in either one of the combinations of Table 6. In some embodiments, the kits of the invention include at least two to at least three modulators; and least one to at least three binding elements specific for an intracellular element listed in either one of the combinations of Table 6. In some embodiments, a kit can comprise at least one to at least four modulators; and at least two to at least five binding elements that are specific to intracellular markers listed in either one of the combinations of Table 6. In some embodiments, a kit can comprise at least four to at least six, or at least seven modulators. In some embodiments, a kit can comprise at least four to at least six, or at least six to at least thirteen binding elements.

The metabolism kits can also include controls such as lyophilized cell lines and protocols.

and patient stratification in the condition. Table 7 illustrates some combinations of reagents to be included into the kits directed to measuring DNA damage. In some embodiments, a kit can comprise at least two modulators and at least three binding elements that are specific to three of the intracellular markers listed in either one of the combinations of Table 7. In some embodiments, a kit can comprise at least two modulators and at least five binding elements that are specific to five of the intracellular markers listed in either one of the combinations of Table 7. In some embodiments, the kits of the invention include at least two to at least three modulators; and least one to at least three binding elements specific for an intracellular element listed in either one of the combinations of Table 7. In some embodiments, a kit can comprise at least one to at least four modulators; and at least two to at least five binding elements that are specific to intracellular markers listed in either one of the combinations of Table 7. In some

TABLE 6

Metabolism

| Cell Types | Cell Surface Markers | Modulator | Intracellular Markers and Epitopes |
| --- | --- | --- | --- |
| T cells | CD3, CD4, CD8, CD45RA, CD45RO | GSK Met | TSC2 (pS1086/pS1088; pS1798; pS939; pT1422; pY1571) |
| Monocytes | CD11b, CD15, CD33, CD34, CD45 | HGF EGF | |
| Bone Marrow (T Cells, Monocytes, nRBCs, Stem Cells, and Megakaryocytes/Megakaryocyte-precursors) | CD11b, CD15, CD33, CD34, CD41, CD42b CD45, CD61, CD71, CD110, CD235a, CD235b | FGR FLT3L SCF Glucose | Pyk2 (pY402) mTOR (pan; pS2448, pS2481; pT2446) pS6 (pS2443; pS235/pS236; pS240; pS2448) |
| PBMC | CD11b, CD15, CD33, CD34, CD45 | | p70S6 kinase (pT389) p-AMPK (T172) |
| Stem Cells | CD34, CD117, CD45 | | p-LKB(S428) p-M2-PK Glut1 Glut 4 Pyruvate determinations Lactate determinations NADPH/NADP ratios |

In some embodiments, the invention provides kits directed to measuring DNA damage in different cell types, e.g., for diagnosis, prognosis, drug discovery, drug development, and patient stratification. The cell types to be analyzed with the kits may be selected according to the condition being studied. One or more cell types may be analyzed in a given condition for diagnosis, prognosis, drug discovery, drug development, embodiments, a kit can comprise at least four to at least six, or at least six to at least eight modulators. In some embodiments, a kit can comprise at least four to at least six, or at least six to at least eight binding elements.

The DNA damage kits can also include controls such as lyophilized cell lines and protocols.

TABLE 7

DNA damage - Hematological Malignancies, e.g., AML, CLL, MPNs and MDS

| Cell Types | Cell Surface Markers | Modulator | Intracellular Markers and Epitopes |
| --- | --- | --- | --- |
| T cells | CD3, CD4, CD8, CD45RA, CD45RO | Etoposide Ara-C | ATM (pS1981) DNA-PKcs (pT2605) |
| Monocytes | CD11b, CD15, CD33, CD34, CD45 | Dauno Azacitidine (marketed as Vidaza) | CHK1 CHK2 (pT63) |
| Bone Marrow (T Cells, Monocytes, nRBCs, Stem Cells, and Megakaryocytes/Megakaryocyte-precursors) | CD11b, CD15, CD33, CD34, CD41, CD42b CD45, CD61, CD71, CD110, CD235a, CD235b | Decitabine (marketed as Dacogen) Vorinostat (marketed as Zolinza) Gemtuzumab (such | pH2AX (pS139) p53 (pS15; pS20) ATR (pT180, pY182) |
| PBMC | CD11b, CD15, | as Gemtuzumab | |

TABLE 7-continued

DNA damage - Hematological Malignancies, e.g., AML, CLL, MPNs and MDS

| Cell Types | Cell Surface Markers | Modulator | Intracellular Markers and Epitopes |
|---|---|---|---|
| Stem Cells | CD33, CD34, CD45 CD34, CD117 | ozogamicin, marketed as Mylotarg) Staurosporine | |

In some embodiments, the invention provides kits directed to measuring G1/S cell cycle in different cell types, e.g., for diagnosis, prognosis, drug discovery, drug development, and patient stratification. The cell types to be analyzed with the kits may be selected according to the condition being studied. One or more cell types may be analyzed in a given condition for diagnosis, prognosis, drug discovery, drug development, and patient stratification in the condition. Table 8 illustrates some combinations of reagents to be included into the kits directed to measuring G1/S cell cycle. In some embodiments, a kit can comprise at least two modulators and at least three binding elements that are specific to three of the intracellular markers listed in either one of the combinations of Table 8. In some embodiments, a kit can comprise at least two modulators and at least five binding elements that are specific to five of the intracellular markers listed in either one of the combinations of Table 8. In some embodiments, the kits of the invention include at least two to at least three modulators; and least one to at least three binding elements specific for an intracellular element listed in either one of the combinations of Table 8. In some embodiments, a kit can comprise at least one to at least four modulators; and at least two to at least five binding elements that are specific to intracellular markers listed in either one of the combinations of Table 8. In some embodiments, a kit can comprise at least four to at least six, or at least six to at least thirteen modulators. In some embodiments, a kit can comprise at least four to at least six, or at least six to at least twelve binding elements.

The G1/S cell cycle kits can also include controls such as lyophilized cell lines and protocols.

TABLE 8

G1/S cell cycle

| Cell Types | Cell Surface Markers | Modulator | Intracellular Markers |
|---|---|---|---|
| Myeloid Bone Marrow/leukemia | CD11b, CD34, CD45, CD33 CD14, CD7 | Staurosporine Etoposide Ara-C | CDK2 CDK4 CDK6 |
| Nucleated Red Blood Cells/Bone Marrow | CD34, CD45, CD71 CD235a, CD235b, CD14, CD7 | Daunorubicin Gemtuzumab (such as Gemtuzumab | CyclinD1 p16 p15 |
| T cells | CD3, CD4, CD8, CD45RA, CD45RO | ozogamicin, marketed as | Rb E2F |
| Monocytes | CD11b, CD15, CD33, CD34, CD45 | Mylotarg) Azacitidine | Cyclin E Cyclin A |
| Bone Marrow (T Cells, Monocytes, nRBCs, Stem Cells, and Megakaryocytes/Megakaryocyte-precursors) | CD11b, CD15, CD33, CD34, CD41, CD42b CD45, CD61, CD71, CD110, CD235a, CD235b | (marketed as Vidaza) Decitabine (marketed as Dacogen) Vorinostat (marketed as Zolinza) Nocodozole | p21 p27 |
| PBMC | CD11b, CD15, CD33, CD34, CD45 | FLT3L SCF | |
| Stem Cells | CD34, CD117, CD45 | SDF1 GCSE GM-CSF Epo IL-6 Solid tumors EGF IGF1 Met FGF GSK Met HGF FGR IFN alpha IFN gamma IL-10 IL-3 IL-4 Clofarabine | |

In some embodiments, the invention provides kits directed to measuring G2/M cell cycle in different cell types, e.g., for diagnosis, prognosis, drug discovery, drug development, and patient stratification. The cell types to be analyzed with the kits may be selected according to the condition being studied. One or more cell types may be analyzed in a given condition for diagnosis, prognosis, drug discovery, drug development, and patient stratification in the condition. Table 9 illustrates some combinations of reagents to be included into the kits directed to measuring G2/M cell cycle. In some embodiments, a kit can comprise at least two modulators and at least three binding elements that are specific to three of the intracellular markers listed in either one of the combinations of Table 9. In some embodiments, a kit can comprise at least two modulators and at least five binding elements that are specific to five of the intracellular markers listed in either one of the combinations of Table 9. In some embodiments, the kits of the invention include at least two to at least three modulators; and least one to at least three binding elements specific for an intracellular element listed in either one of the combinations of Table 9. In some embodiments, a kit can comprise at least one to at least four modulators; and at least two to at least five binding elements that are specific to intracellular markers listed in either one of the combinations of Table 9. In some embodiments, a kit can comprise at least four to at least six, or at least six to at least thirteen modulators. In some embodiments, a kit can comprise at least four to at least six, or at least six to at least nine binding elements.

The G2/M cell cycle kits can also include controls such as lyophilized cell lines and protocols. The G2/M cell cycle kits can also include controls such Nocodozole, taxol and G2/M inhibitors.

TABLE 9

G2/M cell cycle

| Cell Types | Cell Surface Markers | Modulator | Intracellular Markers and Epitopes |
|---|---|---|---|
| Myeloid Bone Marrow/leukemia | CD11b, CD34, CD45, CD33, CD14, CD7 | Staurosporine Etoposide Ara-C | CDK1 (pY15) Cyclin B1 CDC25c |
| Nucleated Red Blood Cells/Bone Marrow | CD34, CD45, CD71, CD235a, CD235b, CD14, CD7 | Daunorubicin Gemtuzumab (such as Gemtuzumab ozogamicin, marketed as Mylotarg) Azacitidine (marketed as Vidaza) Decitabine (marketed as Dacogen) Vorinostat (marketed as Zolinza) Nocodozole FLT3L SCF SDF1 G-CSF GM-CSF Epo IL-6 Solid tumors EGF IGF1 Met FGF GSK Met HGF FGR IFN alpha IFN gamma IL-10 IL-3 IL-4 IL-27 | HistoneH3 (pS28) Aurora A (pT288) Aurora B (pT232) Polo like kinases Wee 1 Myt 1 |
| Monocytes | CD11b, CD15, CD33, CD34, CD45 | | |
| Bone Marrow (T Cells, Monocytes, nRBCs, Stem Cells, and Megakaryocytes/Megakaryocyte-precursors) | CD11b, CD15, CD33, CD34, CD41, CD42b CD45, CD61, CD71, CD110, CD235a, CD235b | | |
| PBMC | CD11b, CD15, CD33, CD34, CD45 | | |
| Stem Cells | CD34, CD117 | | |
| Monocytes | CD11b, CD15, CD33, CD34, CD45 | | |

In some embodiments, the invention includes CLL kits to measure BCR ligand dependent signalling as illustrated in Table 10. In some embodiments, the kits of the invention include at least two to at least three modulators; and least one to at least three binding elements specific for an intracellular element listed in either one of the combinations of Table 10. In some embodiments, a kit can comprise at least one to at least three modulators; and at least two to at least five binding elements that are specific to intracellular markers listed in either one of the combinations of Table 10. In some embodiments, a kit can comprise at least four to at least six, or at least six to at least ten binding elements.

The kits can include at least one binding element specific for cell surface markers CD20, CD19, CD79a, IgM, IgD, CD5, CD3, Kappa light chain or Lambda light chain; and at least one binding element specific for an intracellular marker p-Lyn, p-Syk, P-BLNK, P-PLCg2, p-Akt, p-Erk, p-S6, p-Stat5, cleaved PARP, or Cleaved caspase 3. The kits can optionally comprise at least one modulator of Anti-μ, Anti-γ, Fludarabine (F-Ara-a), or hydrogen peroxide. In some embodiments, the CLL kits to measure BCR ligand dependent signaling comprise at least one binding element specific for cell surface markers CD20, CD19, CD79a, IgM, IgD, CD5, CD3, Kappa light chain or Lambda light chain; at least three binding elements specific for an intracellular marker p-Lyn, p-Syk, P-BLNK, P-PLCg2, p-Akt, p-Erk, p-S6, p-Stat5, cleaved PARP, or Cleaved caspase 3; and at least two of the following modulators: Anti-μ, Anti-γ, or Fludarabine (F-Ara-a). In some embodiments, the CLL kits to measure BCR ligand dependent signaling comprise at least one binding element specific for cell surface markers CD20, CD19, CD79a, IgM, IgD, CD5, CD3, Kappa light chain or Lambda light chain; at least three binding elements specific for an intracellular marker p-Lyn, p-Syk, P-BLNK, P-PLCg2, p-Akt, p-Erk, p-S6, p-Stat5, cleaved PARP, or Cleaved caspase 3; and hydrogen peroxide or Fludarabine (F-Ara-a) as a modulator. In some embodiments, the binding elements are antibodies.

TABLE 10

CLL Kits

| Target Cell Type | Extracellular markers | Target Pathway | Modulator | Intracellular markers |
|---|---|---|---|---|
| B cells | CD20 | BCR ligand dependent signaling | Anti-μ | p-Lyn |
| | CD19 | | Anti-γ | p-Syk |
| | CD79a | | Fludarabine (F-Ara-a) | P-BLNK |
| | IgM | | | P-PLCg2 |
| | IgD | | Bendamustine | p-Akt |
| | CD5 | | | p-Erk |
| | CD3 | | | p-S6 |
| | CD38 | | | p-Stat5 |
| | Kappa light chain | | | p-Stat1 |
| | Lambda light chain | | | p-Stat3 |
| | | | | cleaved PARP |
| | | | | Cleaved caspase 3 |
| B cells | CD20 | BCR ligand independent signaling | Hydrogen peroxide | p-Lyn |
| | CD19 | | | p-Syk |
| | CD79a | | Fludarabine (F-Ara-a) | p-BLNK |
| | IgM | | | p-PLCg |
| | IgD | | Bendamustine | p-Erk |
| | CD5 | | | p-Akt |
| | CD3 | | | p-Stat1 |
| | Kappa light chain | | | p-Stat3 |
| | Lambda light chain | | | p-Stat 5 |
| | CD38 | | | cleaved PARP |
| | | | | Cleaved caspase 3 |

In some embodiments, the invention provides kits directed to the prognosis, diagnosis, patient stratification or selection of treatment for myeloproliferative neoplasms or diseases with activated Jak/Stat signaling. Examples of these kits are depicted in Table 11. The kits can be directed to measure Jak/Stat and Ras/Raf/Erk pathways; and include cocktails of at least one binding element specific for cell surface markers CD14, CD15, or CD45; and binding elements specific for p-Stat5 and p-Erk. The kits can optionally comprise IL-2 and/or GM-CSF as modulator(s). In some embodiments, these kits can be used for drug development of pathway inhibitors. In some embodiments, these kits can be used for drug development of JAK2 specific inhibitors.

TABLE 11

Myeloproliferative Neoplasms or Diseases with Activated Jak/Stat Signaling

| Target Cell Type | Extracellular markers | Target Pathway | Modulator | Intracellular markers |
|---|---|---|---|---|
| Myeloid and T cells | CD14, CD15, CD45 CD3, TCR | Jak/Stat Ras/Raf/Erk | IL-2 GM-CSF IL-15 | p-Stat5 p-Erk p-CREB |

In some embodiment, the invention provides kits directed to the prognosis, diagnosis, patient stratification or selection of treatment of viral infections such as HIV and flu; parasite infections such as helminthes; inflammatory conditions such as allergies, multiple sclerosis and rheumatoid arthritis; and autoimmune conditions such as thyroiditis and lupus. Examples of these kits are depicted in Table 12. In some embodiments, the kits of the invention include at least two to at least three modulators; and least one to at least three binding elements specific for an intracellular element listed in either one of the combinations of Table 12. In some embodiments, a kit can comprise at least one to at least four modulators; and at least two to at least five binding elements that are specific to intracellular markers listed in either one of the combinations of Table 12. In some embodiments, a kit can comprise at least four to at least six, or at least six to at least eight modulators. In some embodiments, a kit can comprise at least four to at least six, or at least six to at least twelve binding elements.

In some embodiments, these kits can be used to test efficacy or drug development of immuno-suppressive reagents.

TABLE 12

Viral Infections, Parasite Infections, Inflammatory Conditions and Autoimmune Conditions

| Target Cell Type | Extracellular markers | Target Pathway | Modulator | Intracellular markers |
|---|---|---|---|---|
| T cells | CD8+ T cells<br>CD3<br>CD45RA<br>CD45RO<br>CD4+ T cells<br>CD3<br>CD45RA<br>CD45RO | T cell Receptor (TCR) signaling | αCD3/αCD28<br>αCD3/αCD137<br>αCD3/αCD44<br>αCD3/αCD134 | ZAP70<br>lck<br>p-65/RelA<br>Erk<br>Akt<br>S6<br>PLCγ1 |
| T cells | CD8+ T cells<br>CD3<br>CD45RA<br>CD45RO<br>CD4+ T cells<br>CD3<br>CD45RA<br>CD45RO<br>Transcription Factor | Cytokine and Growth Factors: Jak/STAT | IL-4, IL-6, IL-12<br>IL-2, IL-23<br>TGF-β<br>IFN-α, IFN-γ | Stat3/4/6<br>Stat1/3/5, p-65/RelA<br>Akt, mTOR, S6, p38<br>Stat1/2, Akt, mTOR, S6, p38 |
| T cells | TH1<br>T-bet<br>TH2<br>GATA3<br>TH17<br>RORγ<br>Regulatory T cells (Treg)<br>FOXP3 | T cell Recptor (TCR) signaling | αCD3/αCD28<br>αCD3/αCD137<br>αCD3/αCD44<br>αCD3/αCD134 | ZAP70<br>lck<br>p-65/RelA<br>Erk<br>Akt<br>S6<br>PLCγ1 |
| T cells | TH1<br>T-bet<br>TH2<br>GATA3<br>TH17<br>RORγt<br>Treg<br>FOXP3 | Cytokine and Growth Factors: Jak/STAT | IL-4, IL-6, IL-12<br>IL-2, IL-23<br>TGF-β<br>IFN-α, IFN-γ | Stat3/4/6<br>Stat1/3/5, p-65/RelA<br>Akt, mTOR, S6, p38<br>Stat1/2, Akt, mTOR, S6, p38 |

In some embodiments, T cell kits are directed to measure TH1 T cells for the prognosis, diagnosis, patient stratification or selection of treatment of viral infections such as HIV and flu. These kits can comprise at least one binding element specific for a cell surface marker CD7, CD3, CD45RA, CD45RO or T-bet; and at least three binding elements specific for an intracellular marker ZAP70, lck, p-65/RelA, Erk, Akt, S6 or PLCγ1. The kits can optionally comprise one binding element specific for a cell surface marker specific for CD8 T cells or CD4 T cells such as one binding element specific for CD8 or CD4. The kits can optionally comprise at least two of the following modulators: αCD3/αCD28, αCD3/αCD137, αCD3/αCD44, and αCD3/αCD134.

In some embodiments, T cell kits are directed to measure TH2 T cells for the prognosis, diagnosis, patient stratification or selection of treatment of parasite infections such as helminthes and/or inflammatory conditions such as allergies, multiple sclerosis and rheumatoid arthritis. These kits can comprise at least one binding element specific for a cell surface marker CD7, CD3, CD45RA, CD45RO or GATA-3; and at least three binding elements specific for an intracellular marker ZAP70, lck, p-65/RelA, Erk, Akt, S6 or PLCγ1. The kits can optionally comprise one binding element specific for a cell surface marker specific for CD8 T cells or CD4 T cells such as one binding element specific for CD8 or CD4. The kits may optionally comprise at least two of the following modulators: αCD3/αCD28, αCD3/αCD137, αCD3/αCD44, or αCD3/αCD134.

In some embodiments, T cell kits are directed to measure TH17 T cells for the prognosis, diagnosis, patient stratification or selection of treatment of autoimmune conditions such as thyroiditis and lupus. These kits can comprise at least one binding element specific for a cell surface marker CD7, CD3, CD45RA, CD45RO or RORγt; and at least three binding elements specific for an intracellular marker ZAP70, lck, p-65/RelA, Erk, Akt, S6 or PLCγ1. The kits can optionally comprise one binding element specific for a cell surface marker specific for CD8 T cells or CD4 T cells such as one binding element specific for CD8 or CD4. The kits can optionally comprise at least two of the following modulators: αCD3/αCD28, αCD3/αCD137, αCD3/αCD44, or αCD3/αCD134.

In some embodiments, T cell kits are directed to measure Treg cells for the prognosis, diagnosis, patient stratification or selection of treatment of cancer and/or autoimmune conditions such as thyroiditis and lupus. These kits can comprise at least one binding element specific for a cell surface marker CD7, CD3, CD45RA, CD45RO or FOXP3; and at least three binding elements specific for an intracellular marker ZAP70, lck, p-65/RelA, Erk, Akt, S6 or PLCγ1. The kits can optionally comprise one binding element specific for a cell surface marker specific for CD8 T cells or CD4 T cells such as one binding element specific for CD8 or CD4. The kits can optionally comprise at least two of the following modulators: αCD3/αCD28, αCD3/αCD137, αCD3/αCD44, or αCD3/αCD134.

In some embodiments, T cell kits are directed to measure TH1 T cells for the prognosis, diagnosis, patient stratification or selection of treatment of viral infections such as HIV and flu. These kits may comprise at least one binding element specific for a cell surface marker CD7, CD3, CD45RA, CD45RO or T-bet; and at least three binding elements specific for an intracellular marker Stat 3, Stat 4 or Stat 6. The kits can optionally comprise one binding element specific for a cell surface marker specific for CD8 T cells or CD4 T cells such as one binding element specific for CD8 or CD4. The kits may optionally comprise at least two of the following modulators: IL-4, IL-6, or IL-12. In some embodiments, these kits can be used to test efficacy of anti-thymocyte globulin.

In some embodiments, T cell kits are directed to measure TH1 T cells for the prognosis, diagnosis, patient stratification or selection of treatment of viral infections such as HIV and flu. These kits can comprise at least one binding element specific for a cell surface CD7, CD3, CD45RA, CD45RO or T-bet; and at least three binding elements specific for an intracellular marker Stat 1, Stat 3, Stat 5, or p-65/RelA. The kits can optionally comprise one binding element specific for a cell surface marker specific for CD8 T cells or CD4 T cells such as one binding element specific for CD8 or CD4. The kits can optionally comprise at least two of the following modulators: IL-2, IL-23, IL-12, IL-6, IFNα, IFNγ, or TGF-β. In some embodiments, these kits can be used to test efficacy of anti-thymocyte globulin.

In some embodiments, T cell kits are directed to measure TH1 T cells for the prognosis, diagnosis, patient stratification or selection of treatment of viral infections such as HIV and flu. These kits can comprise at least one binding element specific for a cell surface marker CD7, CD3, CD45RA, CD45RO or T-bet; and at least three binding elements specific for an intracellular marker Akt, mTOR, S6, or p38. The kits can optionally comprise one binding element specific for a cell surface marker specific for CD8 T cells or CD4 T cells such as one binding element specific for CD8 or CD4. The kits can optionally comprise at TGF-β as a modulator. In some embodiments, these kits can be used to test efficacy of anti-thymocyte globulin.

In some embodiments, T cell kits are directed to measure TH1 T cells for the prognosis, diagnosis, patient stratification or selection of treatment of viral infections such as HIV and flu. These kits can comprise at least one binding element specific for a cell surface marker CD7, CD3, CD45RA, CD45RO or T-bet; and at least three binding elements specific for an intracellular marker Stat 1, Stat 2, Akt, mTOR, S6, or p38. The kits can optionally comprise one binding element specific for a cell surface marker specific for CD8 T cells or CD4 T cells such as one binding element specific for CD8 or CD4. The kits can optionally comprise IFN-α, and IFN-γ as modulators. In some embodiments, these kits can be used to test efficacy of anti-thymocyte globulin.

In some embodiments, T cell kits are directed to measure TH2 T cells for the prognosis, diagnosis, patient stratification or selection of treatment of parasite infections such as helminthes and/or inflammatory conditions such as allergies, multiple sclerosis and rheumatoid arthritis. These kits can comprise at least one binding element specific for a cell surface marker CD7, CD3, CD45RA, CD45RO or GATA-3; and at least three binding elements specific for an intracellular marker Stat 3, Stat 4 or Stat 6. The kits can optionally comprise one binding element specific for a cell surface marker specific for CD8 T cells or CD4 T cells such as one binding element specific for CD8 or CD4. The kits may optionally comprise at least two of the following modulators: IL-4, IL-6, or IL-12. In some embodiments, these kits can be used to test efficacy of anti-thymocyte globulin.

In some embodiments, T cell kits are directed to measure TH2 T cells for the prognosis, diagnosis, patient stratification or selection of treatment of parasite infections such as helminthes and/or inflammatory conditions such as allergies, multiple sclerosis and rheumatoid arthritis. These kits can comprise at least one binding element specific for a cell surface marker CD7, CD3, CD45RA, CD45RO or GATA-3; and at least three binding elements specific for an intracellular marker Stat 1, Stat 3, Stat 5, or p-65/RelA. The kits can optionally comprise one binding element specific for a cell surface marker specific for CD8 T cells or CD4 T cells such as one binding element specific for CD8 or CD4. The kits can optionally comprise at least two of the following modulators: IL-2, IL-23, IL-12, IL-6, IFNα, IFNγ, or TGF-β. In some embodiments, these kits can be used to test efficacy of anti-thymocyte globulin.

In some embodiments, T cell kits are directed to measure TH2 T cells for the prognosis, diagnosis, patient stratification or selection of treatment of parasite infections such as helminthes and/or inflammatory conditions such as allergies, multiple sclerosis and rheumatoid arthritis. These kits can comprise at least one binding element specific for a cell surface marker CD7, CD3, CD45RA, CD45RO or GATA-3; and at least three binding elements specific for an intracellular marker Akt, mTOR, S6, or p38. The kits can optionally comprise one binding element specific for a cell surface marker specific for CD8 T cells or CD4 T cells such as one binding element specific for CD8 or CD4. The kits can optionally comprise at TGF-β as a modulator. In some embodiments, these kits can be used to test efficacy of anti-thymocyte globulin.

In some embodiments, T cell kits are directed to measure TH2 T cells for the prognosis, diagnosis, patient stratification or selection of treatment of parasite infections such as helminthes and/or inflammatory conditions such as allergies, multiple sclerosis and rheumatoid arthritis. These kits can comprise at least one binding element specific for a cell surface marker CD7, CD3, CD45RA, CD45RO o GATA-3; and at least three binding elements specific for an intracellular marker Stat 1, Stat 2, Akt, mTOR, S6, or p38. The kits can optionally comprise one binding element specific for a cell surface marker specific for CD8 T cells or CD4 T cells such as one binding element specific for CD8 or CD4. The kits can optionally comprise IFN-α, and IFN-γ as modulators. In some embodiments, these kits can be used to test efficacy of anti-thymocyte globulin.

In some embodiments, T cell kits are directed to measure TH17 T cells for the prognosis, diagnosis, patient stratification or selection of treatment of autoimmune conditions such as thyroiditis and lupus. These kits can comprise at least one binding element specific for a cell surface marker CD7, CD3, CD45RA, CD45RO or RORγt; and at least three binding elements specific for an intracellular marker Stat 3, Stat 4 or Stat 6. The kits can optionally comprise one binding element specific for a cell surface marker specific for CD8 T cells or CD4 T cells such as one binding element specific for CD8 or CD4. The kits may optionally comprise at least two of the following modulators: IL-4, IL-6, or IL-12. In some embodiments, these kits can be used to test efficacy of anti-thymocyte globulin.

In some embodiments, T cell kits are directed to measure TH17 T cells for the prognosis, diagnosis, patient stratification or selection of treatment of autoimmune conditions such as thyroiditis and lupus. These kits can comprise at least one binding element specific for a cell surface marker CD7, CD3, CD45RA, CD45RO or RORγt; and at least three binding elements specific for an intracellular marker Stat 1, Stat 3, Stat 5, or p-65/RelA. The kits can optionally comprise one binding element specific for a cell surface marker specific for CD8 T cells or CD4 T cells such as one binding element specific for CD8 or CD4. The kits can optionally comprise at least two of the following modulators: IL-2, IL-23, IL-12, IL-6, IFNα, IFNγ, or TGF-β. In some embodiments, these kits can be used to test efficacy of anti-thymocyte globulin.

In some embodiments, T cell kits are directed to measure TH17 T cells for the prognosis, diagnosis, patient stratification or selection of treatment of autoimmune conditions such as thyroiditis and lupus. These kits can comprise at least one binding element specific for a cell surface marker CD7, CD3, CD45RA, CD45RO or RORγt; and at least three binding elements specific for an intracellular marker Akt, mTOR, S6, or p38. The kits can optionally comprise one binding element specific for a cell surface marker specific for CD8 T cells or CD4 T cells such as one binding element specific for CD8 or CD4. The kits can optionally comprise at TGF-β as a modulator. In some embodiments, these kits can be used to test efficacy of anti-thymocyte globulin.

In some embodiments, T cell kits are directed to measure TH17 T cells for the prognosis, diagnosis, patient stratification or selection of treatment of autoimmune conditions such as thyroiditis and lupus. These kits can comprise at least one binding element specific for a cell surface marker CD7, CD3, CD45RA, CD45RO or RORγt; and at least three binding elements specific for an intracellular marker Stat 1, Stat 2, Akt, mTOR, S6, or p38. The kits can optionally comprise one binding element specific for a cell surface marker specific for CD8 T cells or CD4 T cells such as one binding element specific for CD8 or CD4. The kits can optionally comprise IFN-α, and IFN-γ as modulators. In some embodiments, these kits can be used to test efficacy of anti-thymocyte globulin.

In some embodiments, T cell kits are directed to measure Treg cells for the prognosis, diagnosis, patient stratification or selection of treatment of cancer and/or autoimmune conditions such as thyroiditis and lupus. These kits can comprise at least one binding element specific for a cell surface marker CD7, CD3, CD45RA, CD45RO or FOXP3; and at least three binding elements specific for an intracellular marker Stat 3, Stat 4 or Stat 6. The kits can optionally comprise one binding element specific for a cell surface marker for CD8 T cells or CD4 T cells such as one binding element specific for CD8 or CD4. The kits can optionally comprise at least two of the following modulators: IL-4, IL-6, or IL-12. In some embodiments, these kits can be used to test efficacy of anti-thymocyte globulin.

In some embodiments, T cell kits are directed to measure Treg cells for the prognosis, diagnosis, patient stratification or selection of treatment of cancer and/or autoimmune conditions such as thyroiditis and lupus. These kits can comprise at least one binding element specific for a cell surface marker CD7, CD3, CD45RA, CD45RO or FOXP3; and at least three binding elements specific for an intracellular marker Stat 1, Stat 3, Stat 5, or p-65/RelA. The kits can optionally comprise one binding element specific for a cell surface marker specific for CD8 T cells or CD4 T cells such as one binding element specific for CD8 or CD4. The kits can optionally comprise at least two of the following modulators: IL-2, IL-23, IL-12, IL-6, IFNα, IFNγ, or TGF-β. In some embodiments, these kits can be used to test efficacy of anti-thymocyte globulin.

In some embodiments, T cell kits are directed to measure Treg cells for the prognosis, diagnosis, patient stratification or selection of treatment of cancer and/or autoimmune conditions such as thyroiditis and lupus. These kits can comprise at least one binding element specific for a cell surface marker CD7, CD3, CD45RA, CD45RO or FOXP3; and at least three binding elements specific for an intracellular marker Akt, mTOR, S6, or p38. The kits can optionally comprise one binding element specific for a cell surface marker specific for CD8 T cells or CD4 T cells such as one binding element specific for CD8 or CD4. The kits can optionally comprise TGF-β as a modulator. In some embodiments, these kits can be used to test efficacy of anti-thymocyte globulin.

In some embodiments, T cell kits are directed to measure Treg cells for the prognosis, diagnosis, patient stratification or selection of treatment of cancer and/or autoimmune conditions such as thyroiditis and lupus. These kits can comprise at least one binding element specific for a cell surface marker CD7, CD3, CD45RA, CD45RO or FOXP3; and at least three binding elements specific for an intracellular marker Stat 1, Stat 2, Akt, mTOR, S6, or p38. The kits can optionally comprise one binding element specific for a cell surface marker specific for CD8 T cells or CD4 T cells such as one binding element specific for CD8 or CD4. The kits cn optionally comprise IFN-α, and IFN-γ as modulators. In some embodiments, these kits can be used to test efficacy of anti-thymocyte globulin.

In some embodiment, the invention provides kits directed to the prognosis, diagnosis, patient stratification or selection of treatment of MDS, Erythroleukemia and/or any other RBC disorders such as sickle cell anemia. Examples of these kits are depicted in Table 13.

TABLE 13

| | MDS, Erythroleukemia and/or any other RBC disorders | | | |
|---|---|---|---|---|
| Target Cell Type | Extracellular Markers | Target Pathway | Modulator | Intracellular Markers |
| nRBC | CD45, CD34, CD71, CD235a, CD235b | Erythroid development and differentiation Jak/Stat | EPO Lenalidamide Azacitidine (marketed as Vidaza) Decitabine (marketed as Dacogen) Vorinostat (marketed as Zolinza) PMA SCF IFN-γ | Stat1/3/5 pErk/p-Akt/p-S6 |

In some embodiments, nRBC kits can comprise at least one binding element specific for a cell surface marker CD45, CD34, CD71, CD235a, or CD235b; and at least three binding elements specific for an intracellular marker Stat 1, Stat 3, or Stat 5. The kit can optionally comprise at least two of the following modulators: EPO, Lenalidamide, Azacitidine (marketed as Vidaza), Decitabine (marketed as Dacogen), Vorinostat (marketed as Zolinza), PMA, SCF, or IFN-γ. In some embodiments, these kits can be used to test efficacy of Lenalidamide, Azacitidine (marketed as Vidaza), Decitabine (marketed as Dacogen), Vorinostat (marketed as Zolinza), EPO and EPO plus G-CSF.

In some embodiments, nRBC kits can comprise at least one binding element specific for a cell surface marker CD45, CD34, CD71, CD235a, or CD235b; and at least three binding elements specific for an intracellular marker p-Erk, p-Akt or p-S6. The kit can optionally comprise at least two of the following modulators: EPO, Lenalidamide, Azacitidine (marketed as Vidaza), Decitabine (marketed as Dacogen), Vorinostat (marketed as Zolinza), PMA, SCF, or IFN-γ. In some embodiments, these kits can be used to test efficacy of Lenalidamide, Azacitidine (marketed as Vidaza), Decitabine (marketed as Dacogen), Vorinostat (marketed as Zolinza), EPO or EPO plus G-CSF.

In some embodiment, the invention provides Megakaryocytes, Megakaryocyte progenitors, and platelets kits directed to the prognosis, diagnosis, patient stratification or selection of treatment of MDS and/or CLL. Examples of these kits are depicted in Table 14.

In some embodiments, Megakaryocytes, Megakaryocyte progenitors, and platelets kits can comprise at least one binding element specific for a cell surface marker CD45, CD41, CD42b, or CD61; and at least three binding elements specific for an intracellular marker p-Stat 1, p-Stat 3, or p-Stat 5. The kit can optionally comprise at least two of the following modulators: TPO, Lenalidamide, Azacitidine (marketed as Vidaza), Decitabine (marketed as Dacogen), Vorinostat (marketed as Zolinza), PMA, SCF, or IFN-γ. In some embodiments, these kits can be used to test efficacy of Lenalidamide, Azacitidine (marketed as Vidaza), Decitabine (marketed as Dacogen), Vorinostat (marketed as Zolinza), EPO or EPO plus G-CSF.

In some embodiments, Megakaryocytes, Megakaryocyte progenitors, and platelets kits can comprise at least one binding element specific for a cell surface marker CD45, CD41, CD42b, or CD61; and at least three binding elements specific for an intracellular marker p-Erk, p-Akt or p-S6. The kit can optionally comprise at least two of the following modulators: TPO, Lenalidamide, Azacitidine (marketed as Vidaza), Decitabine (marketed as Dacogen), Vorinostat (marketed as Zolinza), PMA, SCF, or IFN-γ. In some embodiments, these kits can be used to test efficacy of Lenalidamide, Azacitidine (marketed as Vidaza), Decitabine (marketed as Dacogen), Vorinostat (marketed as Zolinza), EPO or EPO plus G-CSF.

In some embodiment, the invention provides myeloid kits directed to the prognosis, diagnosis, patient stratification or selection of treatment of autoimmune disorders such as rheumatoid arthritis. Examples of these kits are depicted in Table 15. In some embodiments, these kits can be used to test

TABLE 14

Megakaryocytes, Megakaryocyte progenitors, and platelets kits

| Target Cell Type | Extracellular markers | Target Pathway | Modulator | Intracellular markers |
|---|---|---|---|---|
| Megakaryocytes, Megakaryocyte progenitors, and platelets | CD45, CD41, CD42b, CD61, | Megakaryocyte development and differentiation Jak/Stat | TPO Lenalidamide Azacitidine (marketed as Vidaza) Decitabine (marketed as Dacogen) Vorinostat (marketed as Zolinza) PMA SCF IFN-γ | p-Stat1/3/5 pErk/p-Akt/p-S6 | efficacy or drug development of kinase inhibitors, especially inhibitors of the P38 MAPK pathway.

TABLE 15

Myeloid kits for Autoimmune Disorders

| Target Cell Type | Extracellular Markers | Target Pathway | Modulator | Intracellular Markers |
|---|---|---|---|---|
| Myeloid (monocytes and neutrophils) | CD14, CD11b, CD15, CD33, CD34, CD45 | p-38 MAPK | TNFα LPS TLR Ligands IFNα TLFβ IFNβ GM-CSF | p-p38, pMK2, p-Erk |
| DC, B, Myeloid | CD14, CD11b, CD15, CD33, CD34, CD45, | TLR-9 TLR-7/8 TLR-1 | CpG R848 CL-075 | p-IRAK1, p-IRAK4, p65/RelA, p-Jnk, IRF-7, |

TABLE 15-continued

Myeloid kits for Autoimmune Disorders

| Target Cell Type | Extracellular Markers | Target Pathway | Modulator | Intracellular Markers |
|---|---|---|---|---|
| | CD19, CD3 | TLR-2<br>TLR-4<br>TLR-5<br>MDP | ssRNA<br>FSL 1<br>LPS<br>Flagellin<br>Imiquimod<br>NLRs | MYD88, p-p38,<br>TRAF6 |
| DC, Myeloid | CD14, CD11b,<br>CD15, CD33,<br>CD34, CD45,<br>CD19, CD3 | TLR-3/MAVS | PolyIC, dsRNA | p-IRAK1, p-p-<br>65/RelA, p-p38, p-<br>JnK, IRAK4,<br>MYD88, p65/RelA |

In some embodiments, the myeloid kits comprise at least one binding element specific for a cell surface marker CD14, CD11b, CD15, CD33, CD34, or CD45; and at least three binding elements specific for an intracellular marker p-p38, pMK2, or p-Erk. The kits can optionally comprise at least two of the following modulators: TNFα, LPS, TLR Ligands, IFNα, TLFβ, IFNβ or GM-CSF.

Any of the kits described above can include controls such as cells in a fixed/preserved state. For example when kits have binding elements specific for p-Erk and p-Stat 5, the kit can have as controls one vial of fixed/preserved cells with elevated levels of p-STAT-5 and/or p-ERK; and one vial of fixed/preserved cells with low levels of p-STAT-5 and p-ERK representing a basal state. As another example, when kits have binding elements specific for p-p-38, pMk2 and p-Erk, the kits can have as controls one vial of fixed/preserved cells with elevated levels of p-p38 MAP Kinase, p-MK2, and/or p-Erk; and one vial with low levels of p-p38 MAP Kinase, p-MK2, and/or p-Erk.

The binding elements of the invention can be conjugated to a solid support. In some embodiments, binding elements are immobilized using beads analogous to those known and used for standardization in flow cytometry. Attachment of a multiplicity of binding elements to beads may be done by methods known in the art. Such conjugated beads may be contacted with sample, preferably cell extract, under conditions that allow for a multiplicity analytes, if present, to bind to the multiplicity of immobilized binding elements. Calibration beads may be added to the kits for calibration and performance monitoring of a fluorescence detector. Detailed discussion of the usage of calibration beads disclosed in U.S. Ser. No. 61/176,420 is hereby incorporated by reference in its entity.

Kits of the present invention can also include one or more reagents or supplies that are useful in the invention, such as fixatives, permeabilizing agent, buffers, containers, plates, instructions, and etc.

In certain embodiments, kits of the present invention also comprise fixatives to preserve or "freeze" a cell in a certain state, preferably so that an accurate representation of the structure of the cell is maintained. Cells may be fixed by any of a variety of suitable chemical and physical methods. The commonly used cell fixatives include, but not limited to formaldehyde, paraformaldehyde, glutaraldehyde, acetic acid, picric acid, methanol, ethanol, and acetone. Preferred fixatives comprised 0.756%-0.85% formaldehyde, 25.4-30 mM DNBS, 6.9-6.92% DMSO and 0.086-0.095% TWEEN™ 20 detergent, although many variations are described.

In certain embodiments, kits can comprise wash buffers containing fixatives to fix a cell after stimulation with a modulator. Wash buffers are well known in the art. Prior art examples disclosed in U.S. Pat. No. 7,326,577 and U.S. Pub. No. 2006/0141549 are hereby incorporated by reference in their entireties. One exemplary fixation buffer suitable for whole blood samples is BD™ Phosflow Lyse/Fix Buffer (BD Biosciences, Franklin Lakes, N.J.).

Fixatives have been used for detection of both surface and intracellular antigens. See, Francis C. & Connelly M. C., Rapid single-step method for flow cytometric detection of surface and intracellular antigens using whole blood, Cytometry (1996) 25(1):58-70. Current fixatives revolve primarily around alcohol and formaldehyde/paraformaldehyde, Jacobberger, J W, Flow Cytometric Analysis of Intracellular Protein Epitopes Immunophenotyping (2000) 361-409. The fixative described by Connelly (Pizzolo, G, et al. Detection of membrane and intracellular antigens by flow cytometry following ORTHO PermeaFix fixation. Leukemia. (1994) 8(4):672-76) is the best single step fixative and permeation agent discovered to date (see Metso, T, et al., Identification of intracellular markers in induced sputum and bronchoalveolar lavage samples in patients with respiratory disorders and healthy persons. Respir Med. (2002) 6(11):918-26) stating that "Best results were obtained using a commercial reagent Ortho PermeaFix (OPF) for flow cytometry"). It is called Ortho PERMEAFIX™, although that product has been replaced with a new product called PERMIFLOW™ (INVIRION, INC.™ MI). OPF and its variants are well described in U.S. Pat. No. 5,422,277 and U.S. Pat. No. 5,597,688. Preferred fixatives comprised 0.756%-0.85% formaldehyde, 25.4-30 mM DNBS, 6.9-6.92% DMSO and 0.086-0.095% TWEEN™ 20 detergent, although many variations are described.

In certain embodiment, kits of the present invention can further comprise a permeabilizing agent. Permeabilization is performed to facilitate access to cellular cytoplasm or intracellular molecules, components or structures of a cell. In particular, permeabilization can allow a binding element (such as a phospho-specific antibody) to enter into a cell and reach an intracellular concentration much greater than the concentration in the absence of such permeabilizing treatment.

Permeabilization of the cells can be performed by any suitable method (see, for example, C. A. Goncalves et al., Neurochem. Res. (2000) 25:885-894). These methods include, but are not limited to, exposure to a detergent (such as CHAPS, cholic acid, deoxycholic acid, digitonin, n-dodecyl-β-D-maltoside, lauryl sulfate, glycodeoxycholic acid, n-lauroylsarcosine, saponin, and triton X-100) or to an organic alcohol (such as methanol and ethanol). Other permeabilizing methods comprise the use of certain peptides or toxins that render membranes permeable (see, for example, O. Aguilera et al., FEBS Lett. (1999) 462:273-277; and Bussing A. et al., Cytometry (1999) 37:133-139). Permeabilization may also be performed by addition of an organic alcohol to the cells. Selection of an appropriate permeabilizing agent and optimization of the incubation conditions and time can easily be performed by one of ordinary skill in the art. Cells can be permeabilized in the presence of 90% methanol and incubated on ice for 30 minutes. Following this treatment, the assay plate may be stored at −20° C. for up to one month before being analyzed. Permeabilization can occur concurrently with the fixation step. With for example, BD™ Cytofix/Cytoperm (BD Biosciences, Franklin Lakes, N.J.).

In certain embodiments, some of the components of the kits can be lyophilized or frozen in the multi-well plates as part of the kit. The choice of fluorochrome conjugated binding elements for surface markers and intracellular proteins can be designed for one channel or more than one channel to allow the user some flexibility to add their own stain and to allow some customization of the experiment. Kits may also be designed for specific flow cytometer, for example, one for many channels (LSR II-Becton Dickinson), or one for a small number of channels (FACS Canto II-Becton Dickinson).

The kit can further include, where necessary, other members of the signal-producing system of which system the detectable group is a member (e.g., enzyme substrates), agents for reducing background interference in a test, control reagents, apparatus for conducting a test, and the like. The kit can be packaged in any suitable manner, typically with all elements in a single container along with a sheet of printed instructions for carrying out the test.

Some embodiments of the invention can additionally comprise software on a CD, a removable hard disk drive, USB or flash drive implemented with methods for collection, storage, display and querying information on the relationship between modulators, activated elements, and/or cell type, and may further include further correlations on signaling, e.g. signaling data generated by flow cytometry analysis, such as signaling pathways or signaling levels. Some embodiments of the software comprise a graphical user interface (GUI) for displaying, querying and/or filtering the obtained information.

Such kits can also include information, such as protocols, scientific literature references, package insert materials, clinical trial results, and/or summaries of these and the like, which indicate or establish the activities and/or advantages of the composition, and/or which describe optimal concentration, dosing, administration, side effects, drug interactions, or other information useful to the health care provider. Such information can be based on the results of various studies, for example, studies using experimental animals involving in vivo models and studies based on human clinical trials.

In some embodiments, a kit of the present invention can additionally comprise controls and assay preparation protocols.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A kit comprising:
   (i) at least one antibody specific for a cell surface marker, wherein said cell surface marker is: CD45;
   (ii) at least three antibodies specific for three of the following intracellular markers: Cyclin B1, p-Histone H3, and p-21; and
   (iii) at least two of the following modulators: Azacitidine and Decitabine.

2. The kit of claim 1 further comprising at least one dye of Annexin-V, Yo-Pro, or propidium iodide (PI).

3. The kit of claim 1 further comprising a control cell and/or a control compound.

4. The kit of claim 1 further comprising a protocol.

5. The kit of claim 1 further comprising software for data analysis.

6. The kit of claim 1 wherein said kit is used in diagnosis or prognosis of a condition, or drug discovery, drug development or patient stratification for a condition.

7. The kit of claim 6, wherein said condition is one of non-Hodgkin's lymphoma, Hodgkin's lymphoma, non-B cell lymphomas, other lymphomas, acute or chronic leukemias, polycythemias, thrombocythemias, myelodysplastic disorders, myeloproliferative disorders, myelofibroses, atypical immune lymphoproliferations or a plasma cell disorder.

8. The kit of claim 7, wherein said plasma cell disorder is multiple myeloma, amyloidosis or Waldenstrom's macroglobulinemia.

9. The kit of claim 7, wherein said one of acute or chronic leukemias is a myeloid leukemia or a lymphoid leukemia.

10. The kit of claim 9, wherein said myeloid leukemia is acute myeloid leukemia (AML), chronic myelogenous leukemia (CML), or juvenile myelomonocytic leukemia (JMML).

11. The kit of claim 9, wherein said lymphoid leukemia is non-B cell acute lymphocytic leukemia (T-ALL), B cell acute lymphoblastic leukemia, or chronic lymphocytic leukemia (CLL).

12. The kit of claim 6 wherein said condition is a hematologic disease or disorder selected from the group consisting of, myelodysplastic disorders, myeloproliferative disorders, myelofibroses, polycythemias, thrombocythemias, B cell immunoproliferations, post transplant lymphoproliferation disorder (PTLD), and non-B atypical immune lymphoproliferations.

13. The kit of claim 6, wherein said condition is CLL.

14. The kit of claim 6, wherein said condition is AML.

15. The kit of claim 6, wherein said condition is acute lymphocytic leukemia (ALL).

16. The kit of claim 6, wherein said condition is CML.

17. The kit of claim 6, wherein said condition is a myelodysplastic syndrome (MDS).

* * * * *